US012329377B2

(12) United States Patent
Shelton, IV et al.

(10) Patent No.: US 12,329,377 B2
(45) Date of Patent: *Jun. 17, 2025

(54) TISSUE INGROWTH MATERIALS AND METHOD OF USING THE SAME

(71) Applicant: Cilag GmbH International, Zug (CH)

(72) Inventors: Frederick E. Shelton, IV, Hillsboro, OH (US); Tamara S. V. Widenhouse, Clarksville, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/507,240

(22) Filed: Nov. 13, 2023

(65) Prior Publication Data

US 2024/0081819 A1  Mar. 14, 2024

Related U.S. Application Data

(63) Continuation of application No. 17/181,266, filed on Feb. 22, 2021, now Pat. No. 11,812,953, which is a
(Continued)

(51) Int. Cl.
*A61B 17/072* (2006.01)
*A61B 17/068* (2006.01)
(Continued)

(52) U.S. Cl.
CPC .......... *A61B 17/068* (2013.01); *A61B 17/072* (2013.01); *A61B 17/07207* (2013.01);
(Continued)

(58) Field of Classification Search
CPC ................ A61B 17/068; A61B 17/072; A61B 17/07207; A61B 17/115; A61B 17/00234;
(Continued)

(56) References Cited

U.S. PATENT DOCUMENTS

| 5,698,213 A | 12/1997 | Jamiolkowski et al. |
| 5,700,583 A | 12/1997 | Jamiolkowski et al. |

(Continued)

FOREIGN PATENT DOCUMENTS

| CN | 101332110 A | 12/2008 |
| CN | 101518458 A | 9/2009 |

(Continued)

OTHER PUBLICATIONS

U.S. Appl. No. 14/075,459, filed Nov. 8, 2013, Tissue Ingrowth Materials and Method of Using the Same.
(Continued)

*Primary Examiner* — Scott A Smith
(74) *Attorney, Agent, or Firm* — TROUTMAN PEPPER LOCKE LLP

(57) ABSTRACT

Implantable materials for use with end effectors like surgical stapling devices, and methods for using the same, are generally provided. In some embodiments, adjunct materials for use with surgical staplers are provided. For example, a kit for stapling tissue is provided that can include a surgical stapler having an end effector. The end effector can have first and second jaws. The kit can include an adjunct material having hydrophobic surface regions and hydrophilic surface regions and the adjunct material can be configured to mate to at least one of the jaws of the end effector. Other implants, devices, and methods for surgical stapling are also provided.

20 Claims, 34 Drawing Sheets

Related U.S. Application Data continuation of application No. 16/296,977, filed on Mar. 8, 2019, now Pat. No. 11,219,451, which is a continuation of application No. 15/645,293, filed on Jul. 10, 2017, now Pat. No. 10,285,691, which is a continuation of application No. 14/075,459, filed on Nov. 8, 2013, now Pat. No. 9,700,311.

(51) Int. Cl.
*A61B 17/00* (2006.01)
*A61B 17/115* (2006.01)

(52) U.S. Cl.
CPC ............ *A61B 17/07292* (2013.01); *A61B 2017/00004* (2013.01); *A61B 2017/0046* (2013.01); *A61B 2017/00893* (2013.01); *A61B 2017/00898* (2013.01); *A61B 2017/00938* (2013.01); *A61B 2017/00942* (2013.01); *A61B 2017/07214* (2013.01); *A61B 17/115* (2013.01)

(58) Field of Classification Search
CPC .... A61B 17/07292; A61B 2017/00004; A61B 2017/07214; A61B 2017/0046; A61B 2017/07271; A61B 2017/00893; A61B 2017/00898
USPC ..... 227/19, 175.1, 176.1, 180.1; 606/1, 139, 606/151, 154, 219, 230; 424/423, 424, 424/426, 486, 488
See application file for complete search history.

(56) References Cited

U.S. PATENT DOCUMENTS

| | | | |
|---|---|---|---|
| 6,203,564 B1 | 3/2001 | Hutton et al. | |
| 6,235,869 B1 | 5/2001 | Roby et al. | |
| 6,273,897 B1 | 8/2001 | Dalessandro et al. | |
| 6,309,423 B2 | 10/2001 | Hayes | |
| 6,325,810 B1 | 12/2001 | Hamilton et al. | |
| 6,596,304 B1 | 7/2003 | Bayon et al. | |
| 6,704,210 B1 | 3/2004 | Myers | |
| 7,143,924 B2 | 12/2006 | Scirica et al. | |
| 7,143,925 B2 | 12/2006 | Shelton, IV et al. | |
| 7,665,646 B2 | 2/2010 | Prommersberger | |
| 7,772,352 B2 | 8/2010 | Bezwada | |
| 8,062,330 B2 | 11/2011 | Prommersberger et al. | |
| 8,317,070 B2 | 11/2012 | Hueil et al. | |
| 8,393,514 B2 | 3/2013 | Shelton, IV et al. | |
| 8,413,871 B2 | 4/2013 | Racenet et al. | |
| 8,551,058 B2 | 10/2013 | Measamer et al. | |
| 8,848,345 B2 | 9/2014 | Sologuren-Sanchez et al. | |
| 9,204,880 B2 | 12/2015 | Baxter, III et al. | |
| 9,445,808 B2 | 9/2016 | Woodard et al. | |
| 9,615,826 B2 | 4/2017 | Shelton, IV et al. | |
| 9,700,311 B2 | 7/2017 | Shelton, IV et al. | |
| 9,848,871 B2 | 12/2017 | Harris et al. | |
| 9,913,646 B2 | 3/2018 | Shelton, IV | |
| 9,936,950 B2 | 4/2018 | Shelton, IV et al. | |
| 9,936,954 B2 | 4/2018 | Shelton, IV et al. | |
| 9,974,538 B2 | 5/2018 | Baxter, III et al. | |
| 10,172,611 B2 | 1/2019 | Shelton, IV et al. | |
| 10,206,686 B2 | 2/2019 | Swayze et al. | |
| 10,213,520 B2 | 2/2019 | Shelton, IV et al. | |
| 10,285,691 B2 | 5/2019 | Shelton, IV et al. | |
| 10,456,129 B2 | 10/2019 | Shelton, IV et al. | |
| 10,610,226 B2 | 4/2020 | Shelton, IV et al. | |
| 10,667,808 B2 | 6/2020 | Baxter, III et al. | |
| 10,932,779 B2 | 3/2021 | Vendely et al. | |
| 11,219,451 B2 | 1/2022 | Shelton, IV et al. | |
| 11,553,916 B2 | 1/2023 | Vendely et al. | |
| 11,564,680 B2 | 1/2023 | Shelton, IV et al. | |
| 11,812,953 B2 | 11/2023 | Shelton, IV et al. | |
| 11,937,809 B2 | 3/2024 | Shelton, IV et al. | |
| D1,028,233 S * | 5/2024 | Shelton, IV | A61B 17/07292 D24/145 |
| D1,029,255 S * | 5/2024 | Harris | D24/145 |
| 12,035,913 B2 * | 7/2024 | Shelton, IV | A61B 17/07207 |
| 12,059,153 B2 * | 8/2024 | Shelton, IV | A61B 17/07292 |
| 12,070,213 B2 * | 8/2024 | Chen | A61B 17/07292 |
| 2002/0165563 A1 | 11/2002 | Grant et al. | |
| 2003/0023316 A1 | 1/2003 | Brown et al. | |
| 2004/0175408 A1 | 9/2004 | Chun et al. | |
| 2005/0059996 A1 | 3/2005 | Bauman et al. | |
| 2006/0257458 A1 | 11/2006 | Gorman et al. | |
| 2007/0179528 A1 | 8/2007 | Soltz et al. | |
| 2008/0110959 A1 | 5/2008 | Orban et al. | |
| 2008/0114385 A1 | 5/2008 | Byrum et al. | |
| 2008/0125812 A1 | 5/2008 | Zubik et al. | |
| 2008/0140115 A1 | 6/2008 | Stopek | |
| 2008/0161831 A1 | 7/2008 | Bauman et al. | |
| 2008/0188766 A1 | 8/2008 | Gertner | |
| 2008/0314960 A1 | 12/2008 | Marczyk et al. | |
| 2009/0001122 A1 | 1/2009 | Prommersberger et al. | |
| 2009/0005808 A1 | 1/2009 | Hess et al. | |
| 2009/0234193 A1 | 9/2009 | Weisenburgh et al. | |
| 2009/0270686 A1 | 10/2009 | Duke et al. | |
| 2010/0016888 A1 | 1/2010 | Calabrese et al. | |
| 2010/0331880 A1 | 12/2010 | Stopek | |
| 2011/0192882 A1 | 8/2011 | Hess et al. | |
| 2012/0024934 A1 | 2/2012 | Shelton, IV et al. | |
| 2012/0031950 A1 | 2/2012 | Prommersberger et al. | |
| 2012/0080335 A1 | 4/2012 | Shelton, IV et al. | |
| 2012/0083835 A1 | 4/2012 | Shelton, IV et al. | |
| 2012/0241491 A1 | 9/2012 | Aldridge et al. | |
| 2012/0241496 A1 | 9/2012 | Mandakolathur et al. | |
| 2012/0241498 A1 | 9/2012 | Gonzalez et al. | |
| 2012/0241502 A1 | 9/2012 | Aldridge et al. | |
| 2013/0006172 A1 | 1/2013 | Desai | |
| 2013/0112733 A1 | 5/2013 | Aranyi et al. | |
| 2013/0123816 A1 | 5/2013 | Hodgkinson et al. | |
| 2013/0146642 A1 | 6/2013 | Shelton, IV et al. | |
| 2013/0153641 A1 | 6/2013 | Shelton, IV et al. | |
| 2013/0161374 A1 | 6/2013 | Swayze et al. | |
| 2013/0209659 A1 | 8/2013 | Racenet et al. | |
| 2013/0256365 A1 | 10/2013 | Shelton, IV et al. | |
| 2013/0256372 A1 | 10/2013 | Baxter, III et al. | |
| 2013/0256376 A1 | 10/2013 | Barton et al. | |
| 2013/0256377 A1 | 10/2013 | Schmid et al. | |
| 2014/0081296 A1 | 3/2014 | Palmer et al. | |
| 2014/0158741 A1 | 6/2014 | Woodard et al. | |
| 2015/0129634 A1 | 5/2015 | Shelton, IV et al. | |
| 2015/0133995 A1 | 5/2015 | Shelton, IV et al. | |
| 2015/0134076 A1 | 5/2015 | Shelton, IV et al. | |
| 2015/0134077 A1 | 5/2015 | Shelton, IV et al. | |
| 2015/0173756 A1 | 6/2015 | Baxter, III et al. | |
| 2015/0272575 A1 | 10/2015 | Leimbach et al. | |
| 2015/0351730 A1 | 12/2015 | Stokes et al. | |
| 2015/0351753 A1 | 12/2015 | Shelton, IV et al. | |
| 2015/0351757 A1 | 12/2015 | Harris et al. | |
| 2015/0351760 A1 | 12/2015 | Vendely et al. | |
| 2015/0351762 A1 | 12/2015 | Vendely et al. | |
| 2017/0367694 A1 | 12/2017 | Shelton, IV et al. | |
| 2019/0200978 A1 | 7/2019 | Shelton, IV et al. | |
| 2021/0045738 A1 | 2/2021 | Shelton, IV et al. | |
| 2021/0169472 A1 | 6/2021 | Shelton, IV et al. | |
| 2022/0287710 A1 | 9/2022 | Shelton, IV et al. | |

FOREIGN PATENT DOCUMENTS

| | | |
|---|---|---|
| CN | 101534720 A | 9/2009 |
| CN | 101873834 A | 10/2010 |
| CN | 103209716 A | 7/2013 |
| EP | 1442757 A1 | 8/2004 |
| JP | 2007505708 A | 3/2007 |
| JP | 2011078763 A | 4/2011 |
| JP | 2012065699 A | 4/2012 |
| RU | 2161450 C1 | 1/2001 |
| RU | 61122 U1 | 2/2007 |
| WO | 2006023578 A2 | 3/2006 |
| WO | 2013119365 A1 | 8/2013 |
| WO | 2013148773 A1 | 10/2013 |
| WO | 2013148820 A2 | 10/2013 |

(56) References Cited

FOREIGN PATENT DOCUMENTS

WO    2013148836 A2    10/2013
WO    2014016819 A1    1/2014

OTHER PUBLICATIONS

U.S. Appl. No. 15/645,293, filed Jul. 10, 2017, Tissue Ingrowth Materials and Method of Using the Same.
U.S. Appl. No. 16/296,977, filed Mar. 8, 2019, Tissue Ingrowth Materials and Method of Using the Same.
U.S. Appl. No. 17/081,222, filed Oct. 27, 2020, Tissue Ingrowth Materials and Method of Using the Same.
U.S. Appl. No. 17/181,266, filed Feb. 22, 2021, Tissue Ingrowth Materials and Method of Using the Same.
U.S. Appl. No. 17/828,261, filed May 31, 2022, Tissue Ingrowth Materials and Method of Using the Same.
Extended European Search Report received for European Application No. 14192311.0, mailed on Apr. 21, 2015, 6 pages.
Chen et al., "Elastomeric Biomaterials for Tissue Engineering", Progress in Polymer Science, 2013, vol. 38, (No. 3-4), pp. 584-671.
Lim et al., "Fabrication and Evaluation of Poly(epsilon-Caprolactone)/Silk Fibroin Blend Nanofibrous Scaffold", Biopolymers, May 2012, vol. 97, (No. 5), pp. 265-275.
Zhao et al., "Biodegradable Fibrous Scaffolds Composed of Gelatin Coated Poly(ϵ-caprolactone) Prepared by Coaxial Electrospinning", Journal of Biomedical Materials Research, Nov. 2007, vol. 83, (No. 2), pp. 372-382.

\* cited by examiner

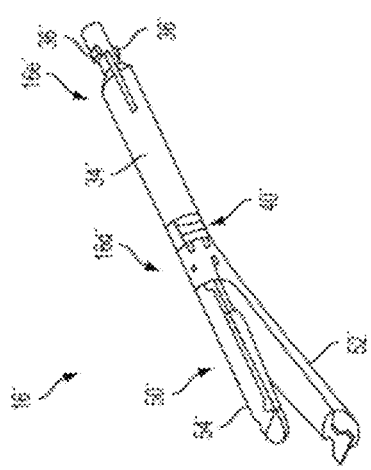
FIG. 9
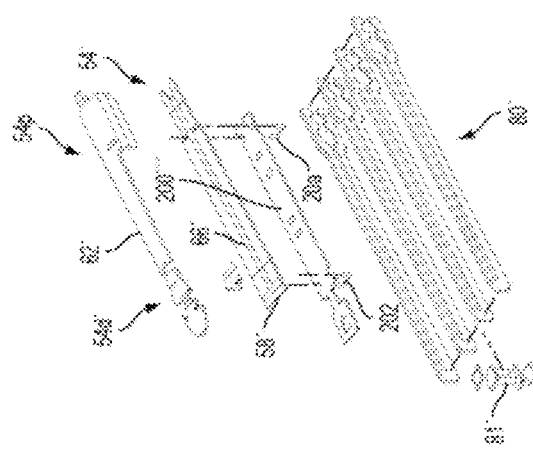
FIG. 10
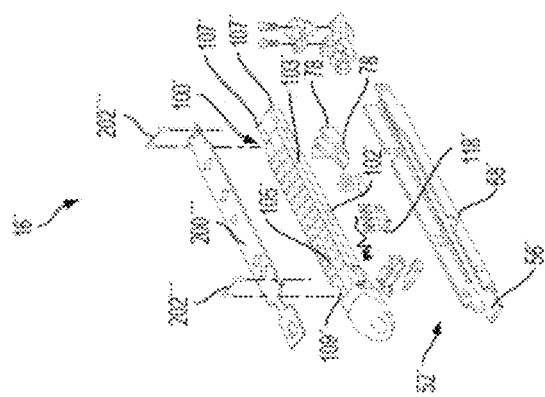

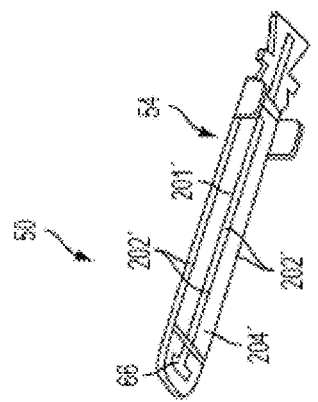
FIG. 12
FIG. 13
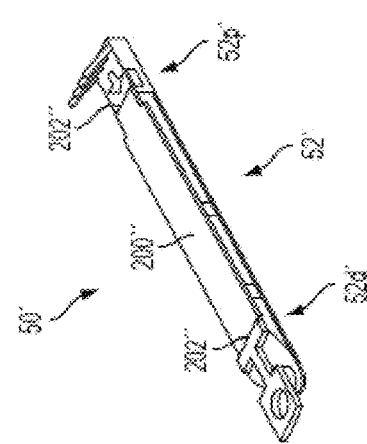
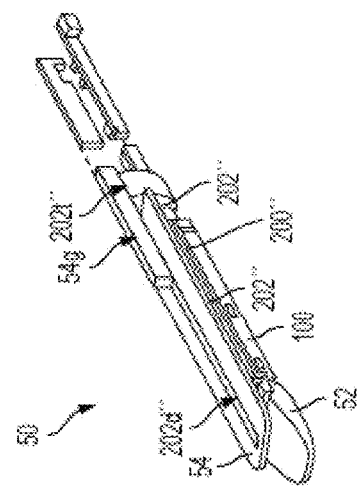
FIG. 14
FIG. 15

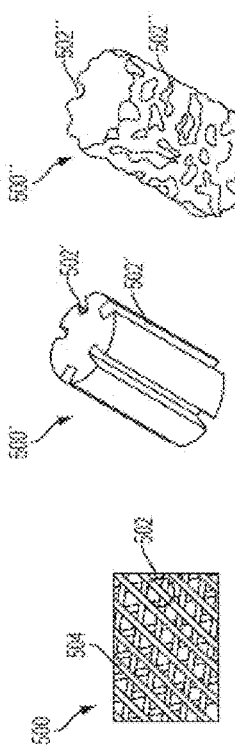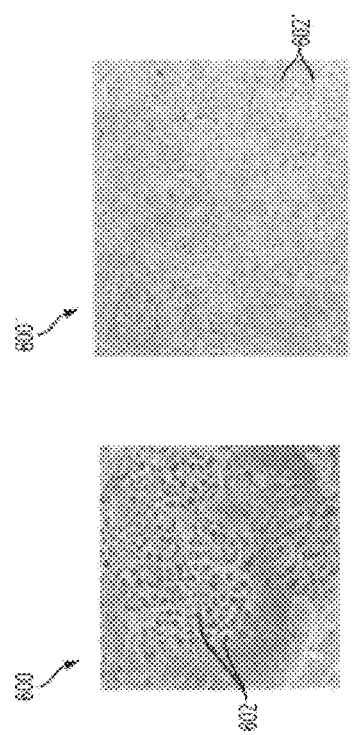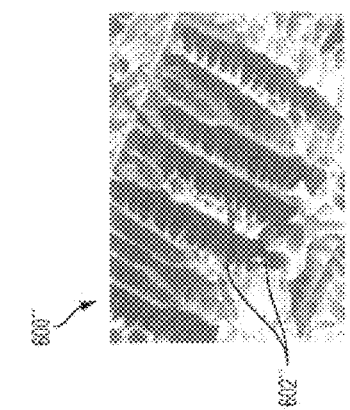

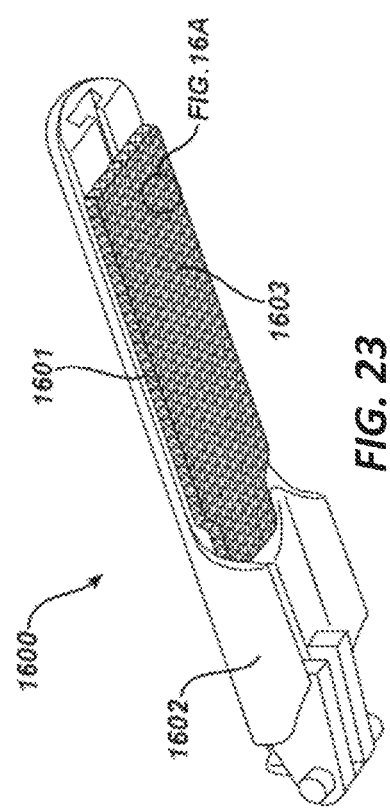
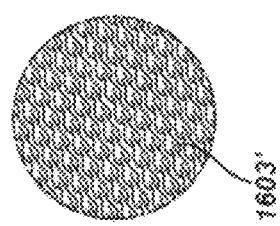
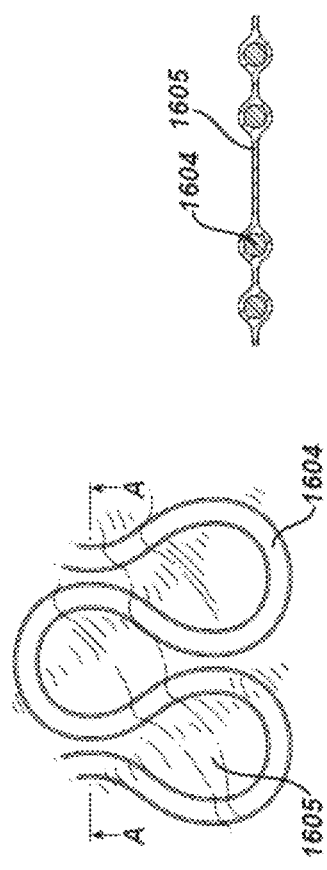
FIG. 23
FIG. 23A
FIG. 23B
FIG. 23C

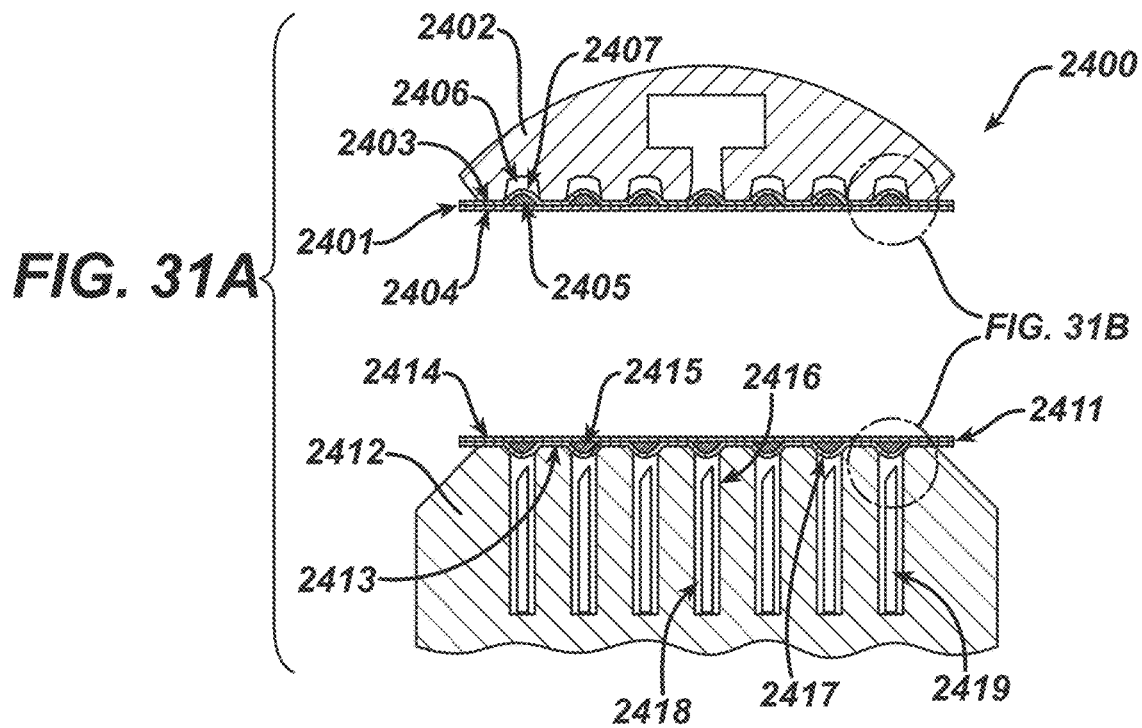
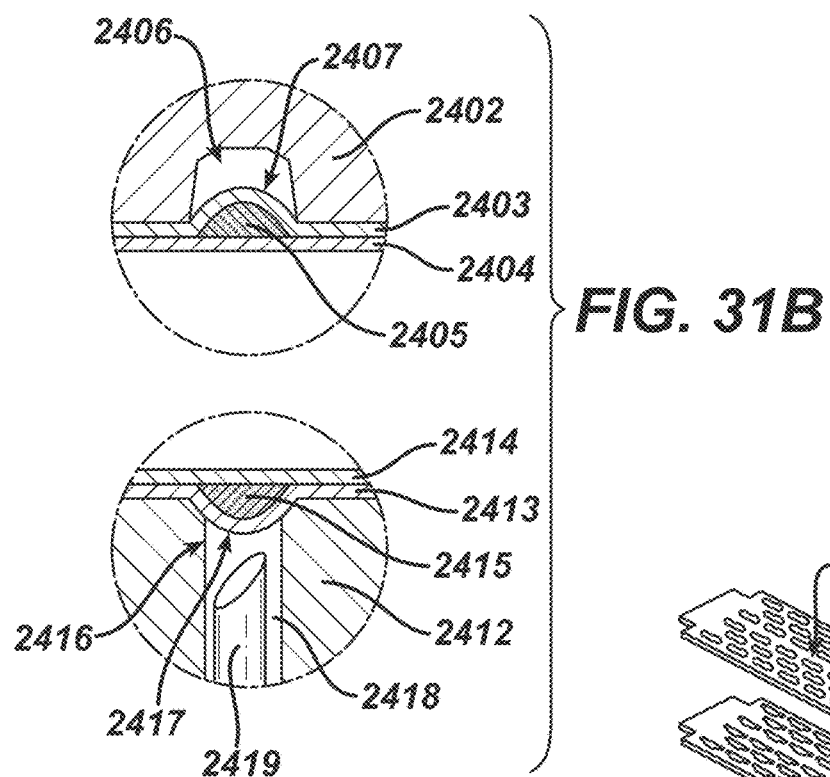
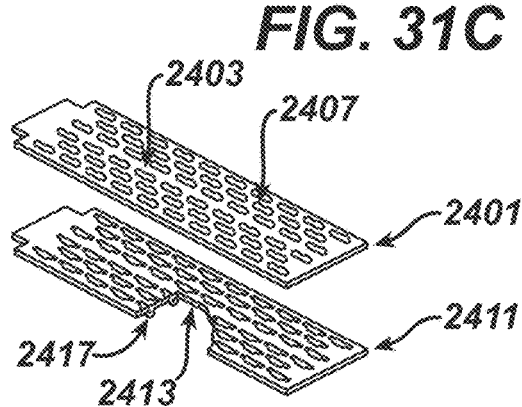

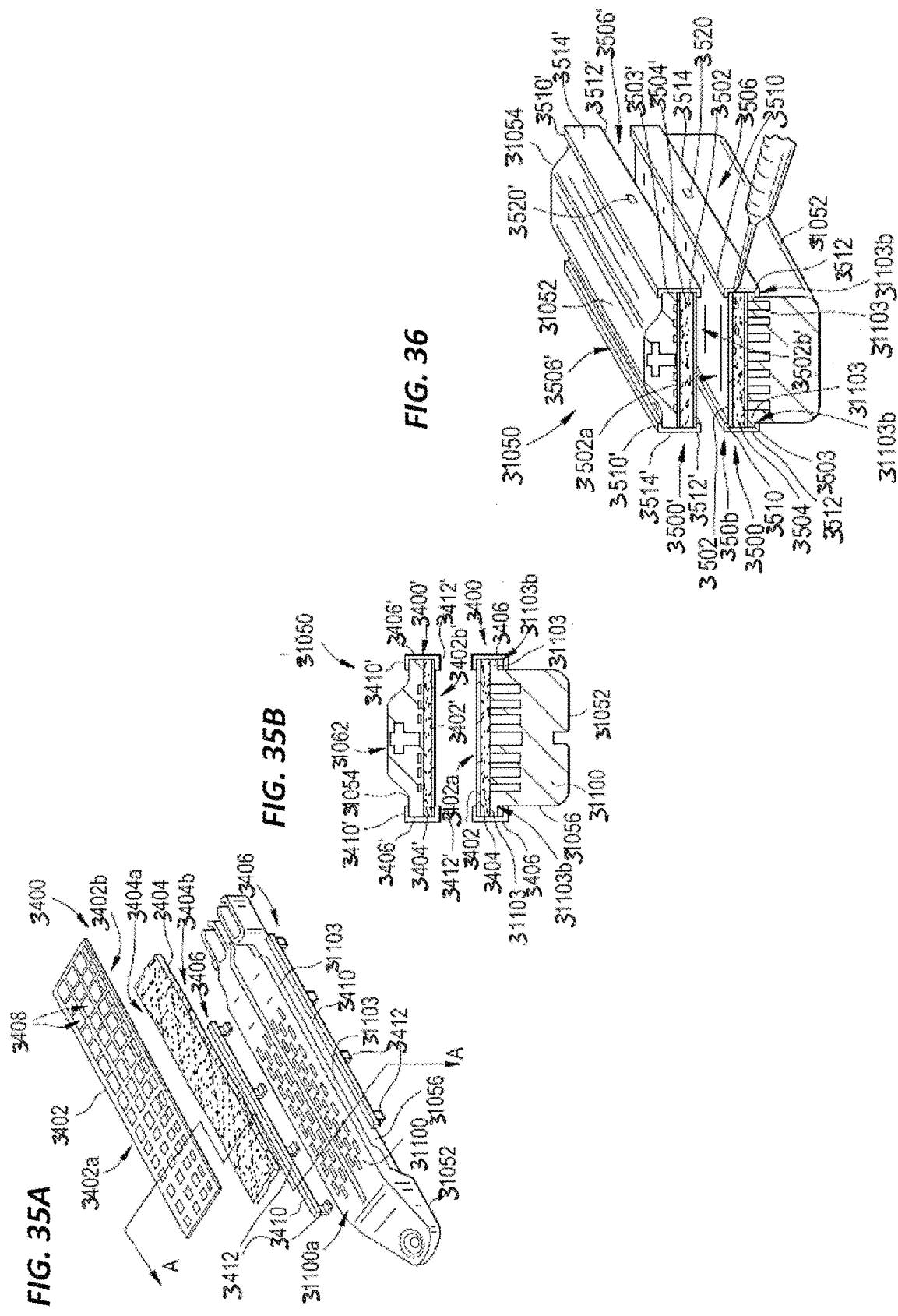

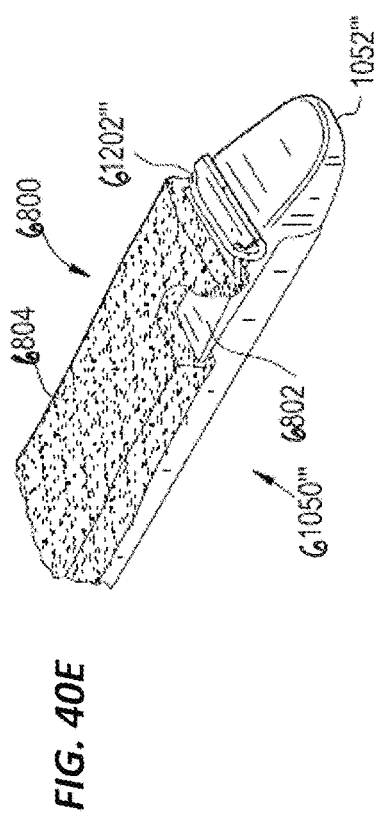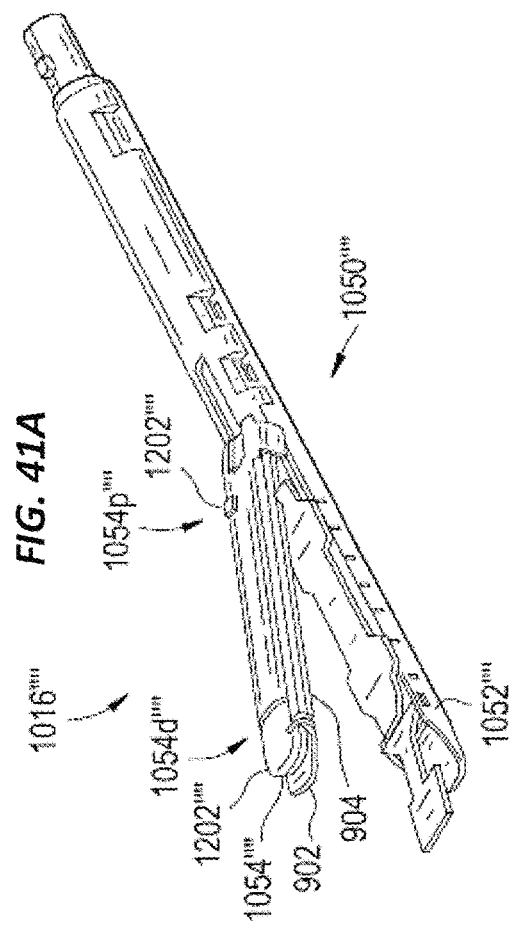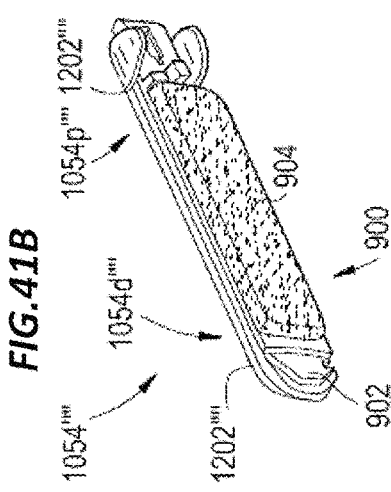

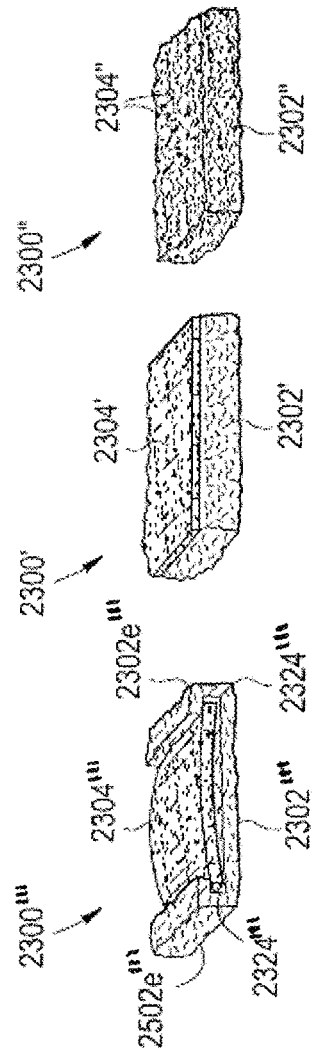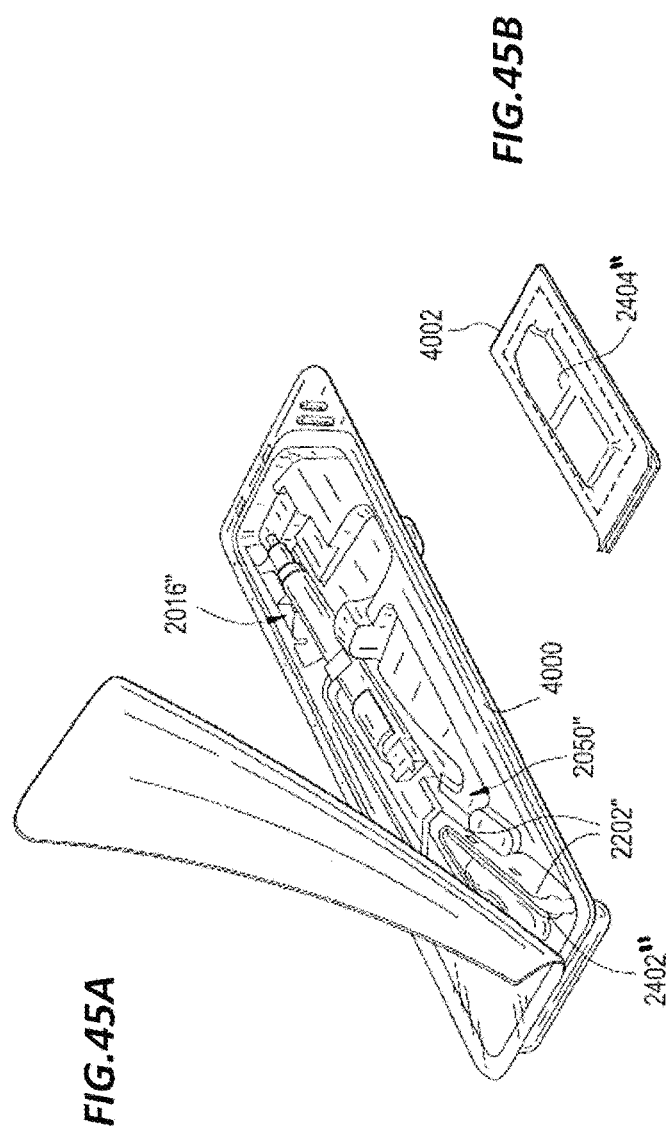

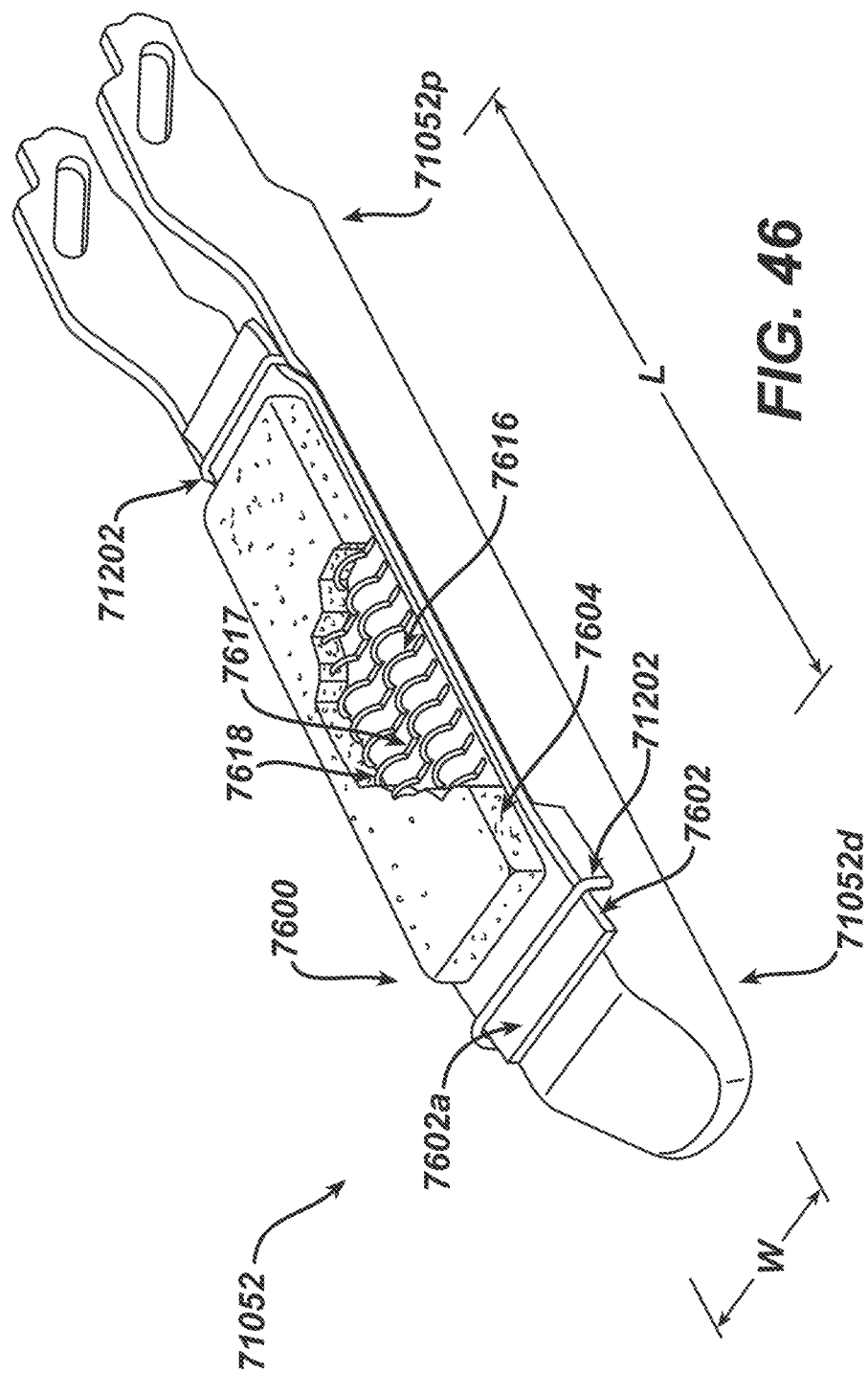

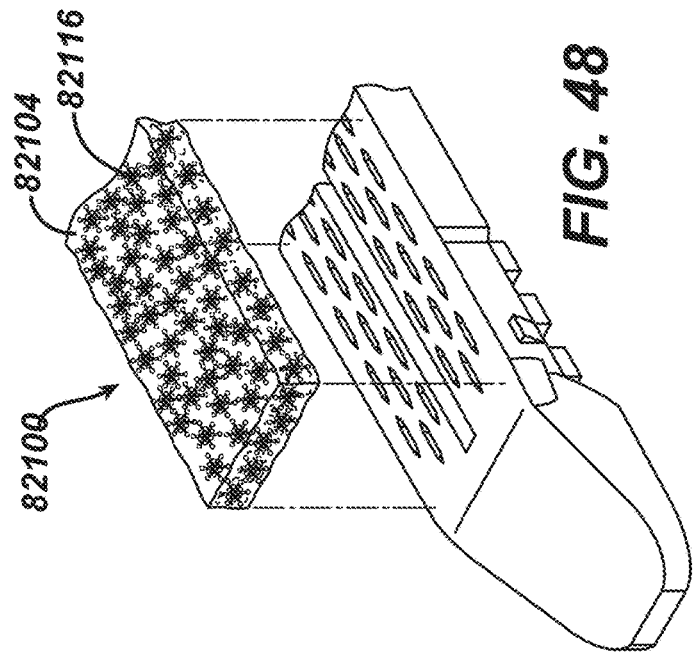
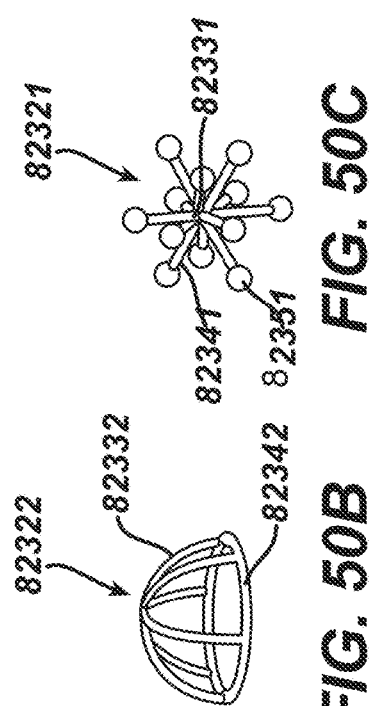
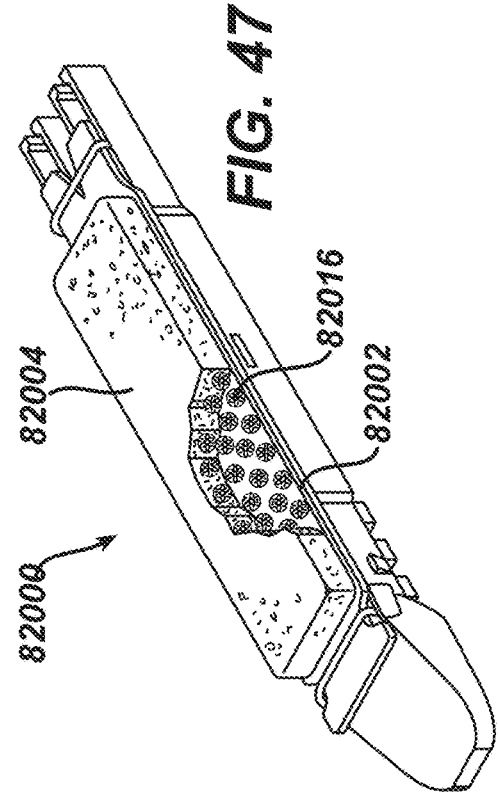
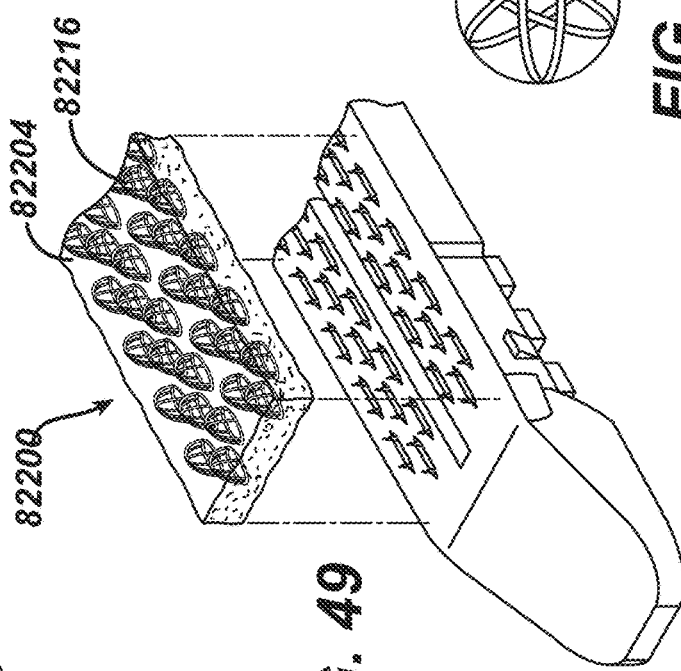
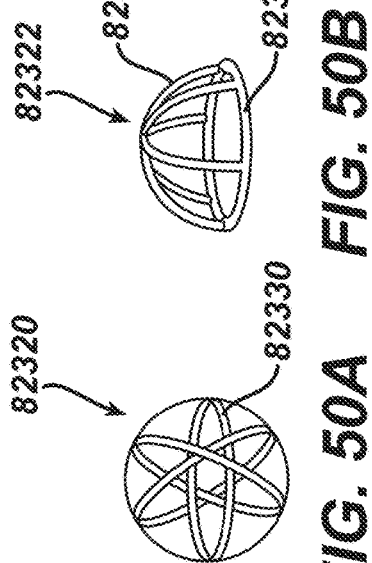
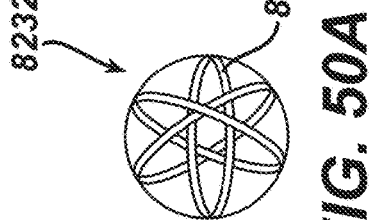

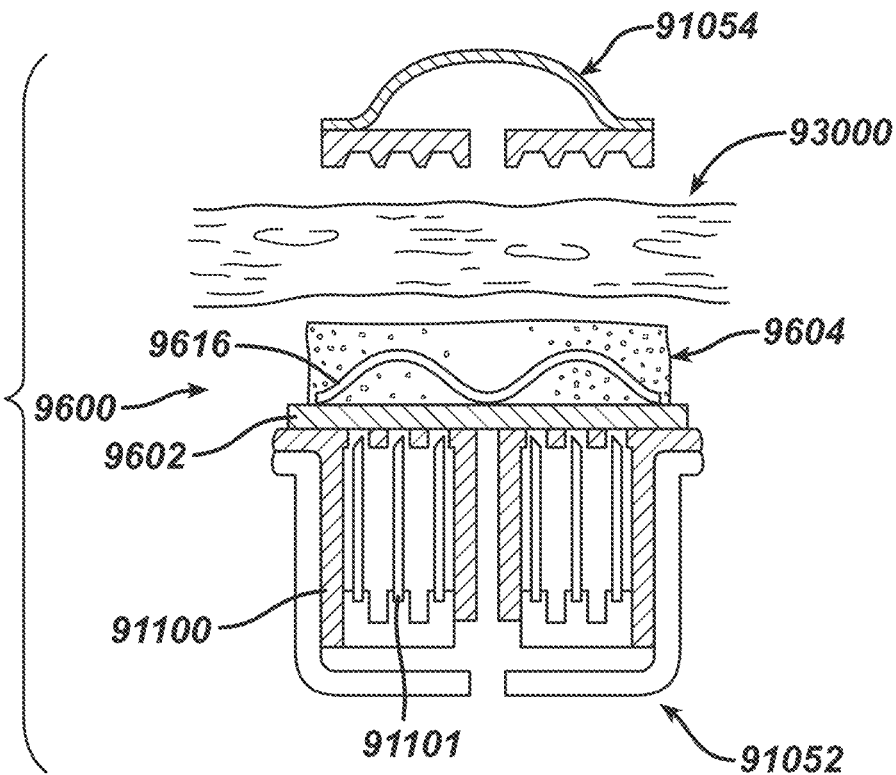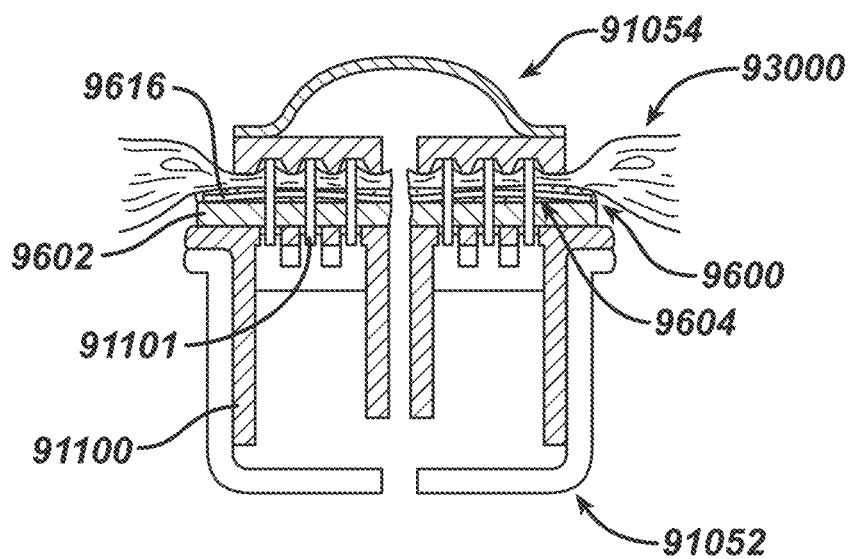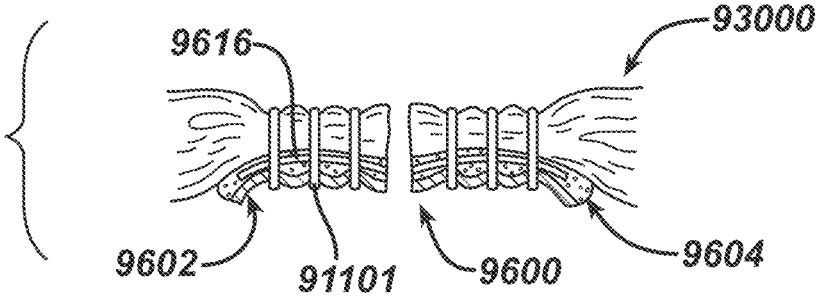

TISSUE INGROWTH MATERIALS AND METHOD OF USING THE SAME

CROSS-REFERENCE TO RELATED APPLICATIONS

This application is a continuation of U.S. patent application Ser. No. 17/181,266 (now U.S. Pat. No. 11,812,953), filed Feb. 22, 2021 and entitled "TISSUE INGROWTH MATERIALS AND METHOD OF USING THE SAME," which is a continuation of U.S. patent application Ser. No. 16/296,977 (now U.S. Pat. No. 11,219,451) filed Mar. 8, 2019, entitled "Tissue Ingrowth Materials and Method of Using the Same," which is a continuation of U.S. patent application Ser. No. 15/645,293 (now U.S. Pat. No. 10,285,691), filed Jul. 10, 2017, entitled "Tissue Ingrowth Materials and Method of Using the Same," which is a continuation of U.S. patent application Ser. No. 14/075,459 (now U.S. Pat. No. 9,700,311), filed Nov. 8, 2013, and entitled "Tissue Ingrowth Materials and Method of Using the Same," which are hereby incorporated by reference herein in their entireties.

FIELD

The present invention relates to surgical instruments, and in particular to methods, devices, and components thereof for cutting and stapling tissue.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

In some instances, biologic materials have been used in conjunction with tissue stapling. However, the use of biologic materials can present a number of problems. For example, biologics can lack desired mechanical properties such as the ability to seal around fastener components (e.g., surgical staples) inserted therethrough. Biologics can also lack the ability to sufficiently reinforce tissue at a surgical site and/or address bleeding or fluid at a surgical site.

Additionally, it can be difficult to maintain a location of the biologic material with respect to jaws of the stapler prior to and during staple ejection. It can also be difficult to keep the biologic material at a desired location at the surgical site after stapling is completed. Further, it can be difficult to manufacture the biologic material to a desired shape and thickness. Common plastic and molding manufacturing techniques are not generally conducive to the manufacture of thin biologic layers for use in conjunction with surgical staplers. The fragile nature of many biologic materials also makes them difficult to use with surgical staplers because they lack structural support.

Further, in some instances, biologic materials have been used in conjunction with tissue stapling. However, the use of biologic materials has presented a number of problems. For example, biologics can lack desired mechanical properties such as springiness or elasticity (i.e., they do not recover, or spring back, after being compressed). Biologics can lack the ability to sufficiently reinforce tissue at a surgical site. Further, it can sometimes be difficult or even impossible to manufacture biologic materials to an exact required shape and/or thickness (e.g., to compensate for variations in tissue thickness, which might only be known at the time of surgery).

Accordingly, there remains a need for improved devices and methods for stapling tissue, blood vessels, ducts, shunts, or other objects or body parts such that leaking and inflammation is minimized while substantially maintaining the natural characteristics of the treatment region. There further remains a need for improved implantable materials that include biologics.

SUMMARY

Implantable materials for use with end effectors like surgical stapling devices, and methods for using the same, are generally provided. In some embodiments, adjunct materials for use with surgical staplers are provided. For example, a kit for stapling tissue is provided that can include a surgical stapler having an end effector. The end effector can have first and second jaws. The kit can include an adjunct material having hydrophobic surface regions and hydrophilic surface regions and the adjunct material can be configured to mate to at least one of the jaws of the end effector.

In some embodiments, the adjunct material can be formed from a hydrophobic polymer and/or copolymer that is treated with a hydrophilic polymer. The adjunct material can also be formed from a hydrophobic polymer and/or copolymer that is treated with an acid or base. In some embodiments, the adjunct material can be formed from a hydrophobic polymer that is treated by covalently bonding hydrophilic moieties onto at least a portion of the hydrophobic polymer. The hydrophilic surface region can be laminated to the hydrophobic surface region. The adjunct material can include an absorbable polymer. In some embodiments, the adjunct material can include a copolymer selected from the group consisting of polyglycolic acid/ polycaprolactone and polylactic acid/polycaprolactone. Also, the adjunct material can include a foam.

In some exemplary embodiments a staple cartridge assembly for use with a surgical stapler, can include a cartridge body having a plurality of staples disposed therein and an adjunct material configured to be coupled to the cartridge and configured to be securely attached to tissue by staples in the cartridge. The adjunct material can have a hydrophobic surface region and an opposite hydrophilic surface region. In some embodiments, the adjunct material can be formed from a hydrophobic polymer and/or copolymer that is treated with a hydrophilic polymer. The adjunct material can also be formed from a hydrophobic polymer and/or copolymer that is treated with an acid or base. In some embodiments, the adjunct material can be formed from a hydrophobic polymer that is treated by covalently bonding hydrophilic moieties onto at least a portion of the hydrophobic polymer. In some embodiments, the hydrophilic surface region can be configured to directly contact tissue when secured to tissue by the staples such that tissue ingrowth is encouraged. The adjunct material can include a copolymer selected from the group consisting of polyglycolic acid/polycaprolactone and polylactic acid/polycaprolactone. In some embodiments, the adjunct material include a polyglycolic acid/polycaprolactone copolymer having polyethylene glycol and/or poloxamer repeat units. The adjunct material can include at least one of a biologic material, an electrically charged material, and an internal support structure. Also, the adjunct material can include a foam.

In other aspects, a method for stapling tissue is provided. The method can include attaching an adjunct material to an end effector on a surgical stapling device such that a hydrophobic surface on the adjunct material directly contacts the end effector. The method can also include engaging tissue between the jaws of the end effector such that a hydrophilic surface on the adjunct material directly contacts the tissue, and actuating the end effector to eject at least one staple from the end effector into the tissue. The at least one staple can extend through the adjunct material to attach the adjunct material to the tissue. In some embodiments, the adjunct material can include a polyglycolic acid/polycaprolactone copolymer having polyethylene glycol and/or poloxamer repeat units. Also, the hydrophilic surface can include a first layer of material and the hydrophobic surface can be a coating that is laminated to the first layer of material.

BRIEF DESCRIPTION OF THE DRAWINGS

The invention will be more fully understood from the following detailed description taken in conjunction with the accompanying drawings, in which:

FIG. 9 is a perspective view of another exemplary embodiment of an attachment portion for use a surgical instrument;

FIG. 10 is an exploded perspective view of an end effector of the attachment portion of FIG. 9;

FIG. 12 is a perspective view of a lower jaw of the end effector of FIG. 3;

FIG. 13 is a perspective view of an upper jaw of the end effector of FIG. 3, the upper jaw having an adjunct material associated therewith;

FIG. 14 is a perspective view of portions of the end effector of FIG. 2 including a retention member configured to releasably retain an adjunct material;

FIG. 15 is a perspective view of a lower jaw of the end effector of FIG. 10;

FIG. 19A is a perspective view of an exemplary adjunct material having surface features;

FIG. 19B is a perspective view of another exemplary adjunct material having surface features;

FIG. 19C is a perspective view of yet another exemplary adjunct material having surface features;

FIG. 20A is a scanning electron microscope image of an exemplary adjunct material having surface features;

FIG. 20B is a scanning electron microscope image of another exemplary adjunct material having surface features;

FIG. 20C is a scanning electron microscope image of yet another exemplary adjunct material having surface features;

FIG. 23 illustrates an end effector having a tissue reinforcement material with a plurality of fibers in a loop structure arrangement;

FIG. 23A is a detail view of a portion of the tissue reinforcement material of FIG. 23.

FIG. 23B is a schematic view of a portion of a strand of fiber used to form the tissue reinforcement material of FIG. 23;

FIG. 23C is a sectional view of the strand of fiber of FIG. 23B at section AA;

FIG. 31A is a sectional view of opposed jaws of an end effector having another alternative exemplary tissue reinforcement material;

FIG. 31B is a detailed view of portions of the tissue reinforcement material on the jaws of the end effector of FIG. 31A;

FIG. 31C is a perspective view of two layers of the tissue reinforcement material shown in FIGS. 31A and 31B;

FIG. 35A is a perspective exploded view of one exemplary embodiment of a hybrid adjunct material and a lower jaw of an end effector;

FIG. 35B is a front cross-sectional view of the hybrid adjunct material of FIG. 35A in a non-exploded configuration and taken along line A-A, and further illustrating a second hybrid adjunct material coupled to an upper jaw of the end effector;

FIG. 36 is a perspective cross-sectional view of another exemplary embodiment of a first hybrid adjunct material coupled to a lower jaw of an end effector and a second hybrid adjunct material coupled to an upper jaw of the end effector;

FIG. 40E is a perspective view of the lower jaw of FIG. 40A with the biologic layer fully coupled to the synthetic layer and a portion of the biologic layer removed for illustrative purposes;

FIG. 41A is a perspective view of another exemplary embodiment of an attachment portion of a surgical instrument having a hybrid adjunct material coupled to an upper jaw thereof;

FIG. 41B is a perspective view of the upper jaw of FIG. 41A;

FIG. 44A is a perspective view of one exemplary embodiment of a hybrid adjunct material having a snap-fit configuration between a biologic layer and a synthetic layer thereof;

FIG. 44B is a perspective view of another exemplary embodiment of a hybrid adjunct material having biologic layer laminated to a synthetic layer;

FIG. 44C is a perspective view of still another exemplary embodiment of a hybrid adjunct material having biologic materials imbibed in a synthetic layer;

FIG. 45A is a perspective view of one exemplary embodiment of packaging for a surgical instrument having a synthetic layer of a hybrid adjunct material associated therewith;

FIG. 45B is a perspective view of one exemplary embodiment of packaging for a biologic layer, the biologic layer being configured to mate with the synthetic layer of FIG. 45A;

FIG. 46 is a perspective view of an exemplary staple cartridge having a hybrid adjunct material in accordance with the present invention;

FIGS. 47-49 are perspective views illustrating exemplary attachments of biological tissue reinforcement membranes to cartridge bodies, and exemplary compressible elastic members;

FIG. 50A-50C is an exploded view of variations of the compressible elastic members illustrated in FIGS. 47-49; and FIGS. 51-53 are cross sectional views illustrating the operation of the exemplary staple cartridge of FIG. 46.

DETAILED DESCRIPTION

Figure 1:
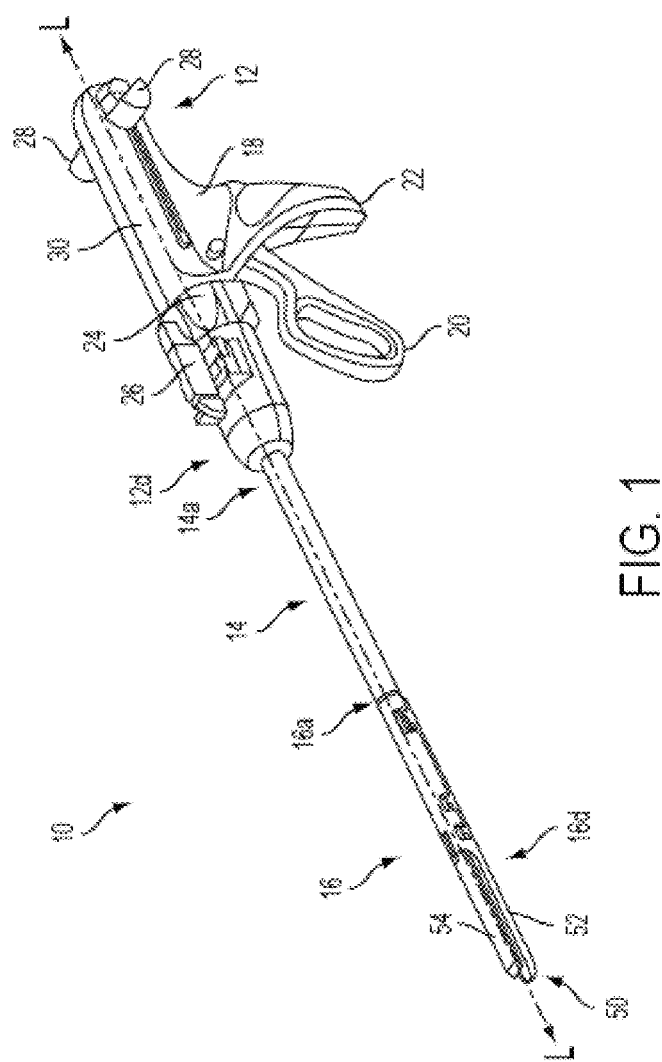
FIG. 1 is a perspective view of one exemplary embodiment of a surgical instrument having an attachment portion attached to a distal end thereof.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the various embodiments generally have similar features when those components are of a similar nature and/or serve a similar purpose.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, collectively referred to herein as "adjunct materials," in conjunction with surgical instruments to help improve surgical procedures. A person skilled in the art may refer to these types of materials as buttress materials as well as adjunct materials. While a variety of different end effectors can benefit from the use of adjunct materials, in some exemplary embodiments the end effector can be a surgical stapler. When used in conjunction with a surgical stapler, the adjunct material(s) can be disposed between and/or on jaws of the stapler, incorporated into a staple cartridge disposed in the jaws, or otherwise placed in proximity to the staples. When staples are deployed, the adjunct material(s) can remain at the treatment site with the staples, in turn providing a number of benefits. In some instances, the material(s) can be used to help seal holes formed by staples as they are implanted into tissue, blood vessels, and various other objects or body parts. Further, the materials can be used to provide tissue reinforcement at the treatment site. Still further, the materials can help reduce inflammation, promote cell growth, and otherwise improve healing.

Some configurations of adjunct materials include both synthetic and biologic materials. The combination of both types of materials can result in the formation of a hybrid adjunct material. Hybrid adjunct materials, when properly designed and/or selected, can combine beneficial features of synthetic material(s) and beneficial features of biologic material(s) in a single hybrid adjunct material. Thus, while an otherwise desirable biologic material may lack an also desirable mechanical (or other) property, combining the biologic material with a synthetic material providing that mechanical (or other) property can provide a hybrid adjunct material having both desirable properties. For example, a hybrid adjunct material can be designed to combine benefits of biologic material (such as improved healing and tissue growth at a surgical site) with desirable mechanical properties of synthetic material (such as an ability to compress and form a seal around a fastener component).

Further, while often biologic material can be difficult to shape into a desired shape and then held in that desired configuration, by using synthetic material in conjunction with the biologic material, the synthetic material can serve as a support structure for the biologic material. Accordingly, the benefits of biologic material, such as improved healing and tissue growth at the surgical site, can be provided with the stability afforded by synthetic material.

As another example, For example, a hybrid adjunct material can be designed to combine benefits of biologic material (such as improved healing and tissue growth at a surgical site) with desirable mechanical properties of synthetic material (such as springiness or elasticity in the resulting hybrid adjunct material).

Surgical Stapling Instrument

Figure 2:
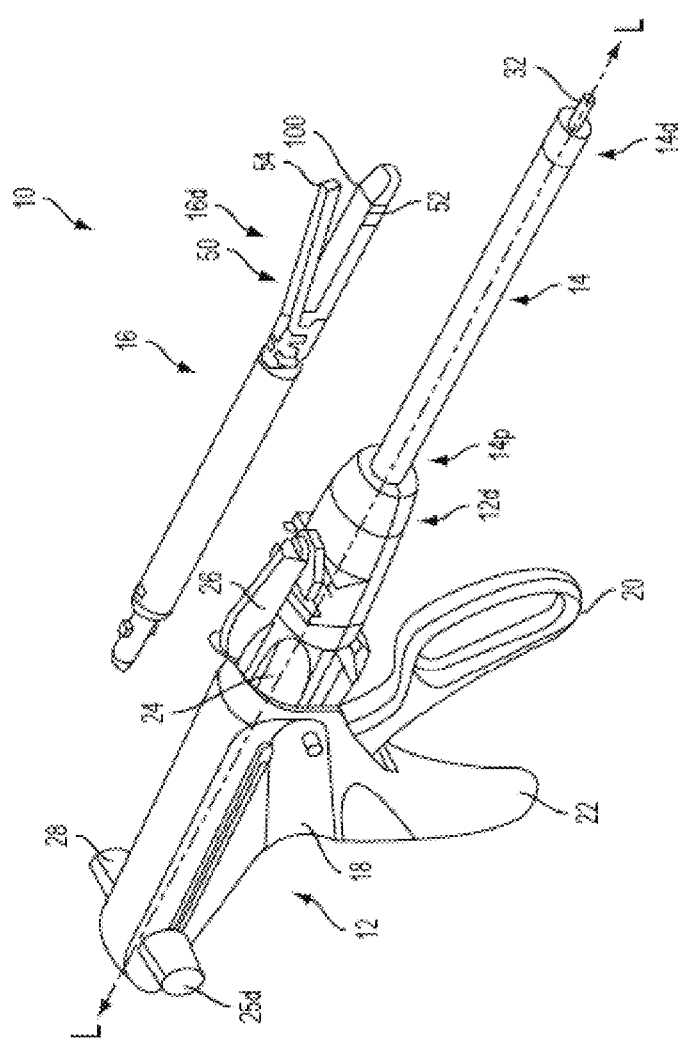
FIG. 2 is a perspective view of the surgical instrument of FIG. 1 with the attachment portion detached from a shaft of the instrument.

While a variety of surgical instruments can be used in conjunction with the adjunct materials disclosed herein, FIGS. 1 and 2 illustrate one, non-limiting exemplary embodiment of a surgical stapler 10 suitable for use with one or more adjunct materials. As shown the instrument 10 includes a handle assembly 12, a shaft 14 extending distally from a distal end 12d of the handle assembly 12, and an attachment portion 16 removably coupled to a distal end 14d of the shaft 14. Because the illustrated embodiment is a surgical stapler, a distal end 16d of the attachment portion 16 includes an end effector 50 having jaws 52, 54, although other types of end effectors can be used with the shaft 14, handle assembly 12, and components associated with the same. As shown, the surgical stapler includes opposed first and second jaws 52, 54 with the first, lower jaw 52 including an elongate channel 56 (FIG. 4) configured to support a staple cartridge 100, and the second, upper jaw 54 having an inner surface 58 (FIGS. 3, 4, and 6) that faces the lower jaw 52 and that is configured to operate as an anvil to help deploy staples of a staple cartridge. The jaws 52, 54 are configured to move relative to one another to clamp tissue or other objects disposed therebetween, and an axial drive assembly 80 (FIG. 11) can be configured to pass through at least a portion of the end effector 50 to eject the staples into the clamped tissue. In various embodiments a knife blade 81 can be associated with the axial drive assembly 80 to cut tissue during the stapling procedure.

Operation of the end effector 50 and drive assembly 80 can begin with input from a clinician at the handle assembly 12. The handle assembly 12 can have many different configurations designed to manipulate and operate the end effector associated therewith. In the illustrated embodiment, the handle assembly 12 has a pistol-grip type housing 18 with a variety of mechanical components disposed therein to operate various features of the instrument. For example, the handle assembly 12 can include mechanical components as part of a firing system actuated by a trigger 20. The trigger 20 can be biased to an open position with respect to a stationary handle 22, for instance by a torsion spring, and movement of the trigger 20 toward the stationary handle 22 can actuate the firing system to cause the axial drive assembly 80 to pass through at least a portion of the end effector 50 and eject staples from a staple cartridge disposed therein. A person skilled in the art will recognize various configurations of components for a firing system, mechanical or otherwise, that can be used to eject staples and/or cut tissue, and thus a detailed explanation of the same is unnecessary.

Other non-limiting examples of features that can be incorporated into the handle assembly 22 that affect manipulation and operation of an end effector associated therewith include a rotatable knob 24, an articulation lever 26, and retraction knobs 28. As shown, the rotatable knob 24 can be mounted on a forward end of a barrel portion 30 of the handle assembly 12 to facilitate rotation of the shaft 14 (or the attachment portion 16) with respect to the handle assembly 12 around a longitudinal axis L of the shaft 14. The actuation lever 26 can also be mounted on a forward end of the barrel portion 30, approximately adjacent to the rotatable knob 24. The lever 26 can be manipulated from side-to-side along a surface of the barrel portion 30 to facilitate reciprocal articulation of the end effector 50. One or more retraction knobs 28 can be movably positioned along the barrel portion 30 to return the drive assembly 80 to a retracted position, for example after the firing system has completed a firing stroke. As shown, the retraction knobs 28 move proximally toward a back end of the barrel portion 30 to retract components of the firing system, including the drive assembly 80.

Still other non-limiting examples of features that can be incorporated into the handle assembly 22 that affect manipulation and operation of an end effector associated therewith can include a firing lockout assembly, an anti-reverse clutch mechanism, and an emergency return button. A firing lockout assembly can be configured to prevent the firing system from being actuated at an undesirable time, such as when an end effector is not fully coupled to the instrument. An anti-reverse clutch mechanism can be configured to prevent components of the firing system from moving backwards when such backwards movement is undesirable, such as when the firing stroke has only been partially completed but temporarily stopped. An emergency return button can be configured to permit components of a firing system to be retracted before a firing stroke is completed, for instance in a case where completing the firing stroke may cause tissue to be undesirably cut. Although features such as a firing lockout assembly, an anti-reverse clutch mechanism, and an emergency return button are not explicitly illustrated in the instrument 10, a person skilled in the art will recognize a variety of configurations for each feature that can be incorporated into a handle assembly and/or other portions of a surgical stapler without departing from the spirit of the present disclosure. Additionally, some exemplary embodiments of features that can be incorporated into the handle assembly 12 are provided for in patents and patent applications incorporated by reference elsewhere in the present application.

The shaft 14 can be removably coupled to the distal end 12d of the handle assembly 12 at a proximal end 14p of the shaft 14, and a distal end 14d of the shaft 14 can be configured to receive the attachment portion 16. As shown, the shaft 14 is generally cylindrical and elongate, although any number of shapes and configurations can be used for the shaft, depending, at least in part, on the configurations of the other instrument components with which it is used and the type of procedure in which the instrument is used. For example, in some embodiments, a distal end of one shaft can have a particular configuration for receiving certain types of end effectors, while a distal end of another shaft can have a different configuration for receiving certain other types of end effectors. Components of the firing system, such as a control rod 32 (FIG. 2), can be disposed in the shaft 14 so that the components can reach the end effector 50 and drive assembly 80 to provide actuation of the same. For example, when the trigger 20 operates the firing system, the control rod 32 can be advanced distally through at least a portion of the shaft 14 to cause the jaws 52, 54 to collapse towards each other and/or to drive the drive assembly 80 distally through at least a portion of the end effector 50.

The shaft 14 can also include one or more sensors (not shown) and related components, such as electronic components to help operate and use the sensors (not shown). The sensors and related components can be configured to communicate to a clinician the type of end effector associated with the distal end 14d of the shaft 14, among other parameters. Likewise, the handle assembly 12 can include one or more sensors and related components configured to communicate to a clinician the type of end effector and/or shaft associated with the distal end 12d of the handle assembly 12. Accordingly, because a variety of shafts can be interchangeably coupled with the handle assembly 12 and a variety of end effectors having different configurations can be interchangeably coupled with various shafts, the sensors can help a clinician know which shaft and end effector are being used. Additionally, the information from the sensors can help a monitoring or control system associated with the instrument know which operation and measurement parameters are relevant to a clinician based on the type of shaft and end effector coupled to the handle assembly. For example, when the end effector is a stapler, information about the number of times the drive assembly 80 is fired may be relevant, and when the end effector is another type of end effector, such as a cutting device, the distance the cutting portion traveled may be relevant. The system can convey the appropriate information to the clinician based on the end effector that is sensed.

A person skilled in the art will recognize that various configurations of monitoring and control systems can be used in conjunction with the surgical instruments provided herein. For example, sensors associated with any of the end effector 50, the attachment portion 16, the shaft 14, and the handle assembly 12 can be configured to monitor other system parameters, and a monitoring or control system can communicate to a clinician the relevant other parameters based on the type of shaft or attachment portion associated with the handle assembly. Further details about sensors and related components, as well as monitoring and control systems, can be found in patents and patent applications incorporated by reference elsewhere in the present application.

Figure 3:
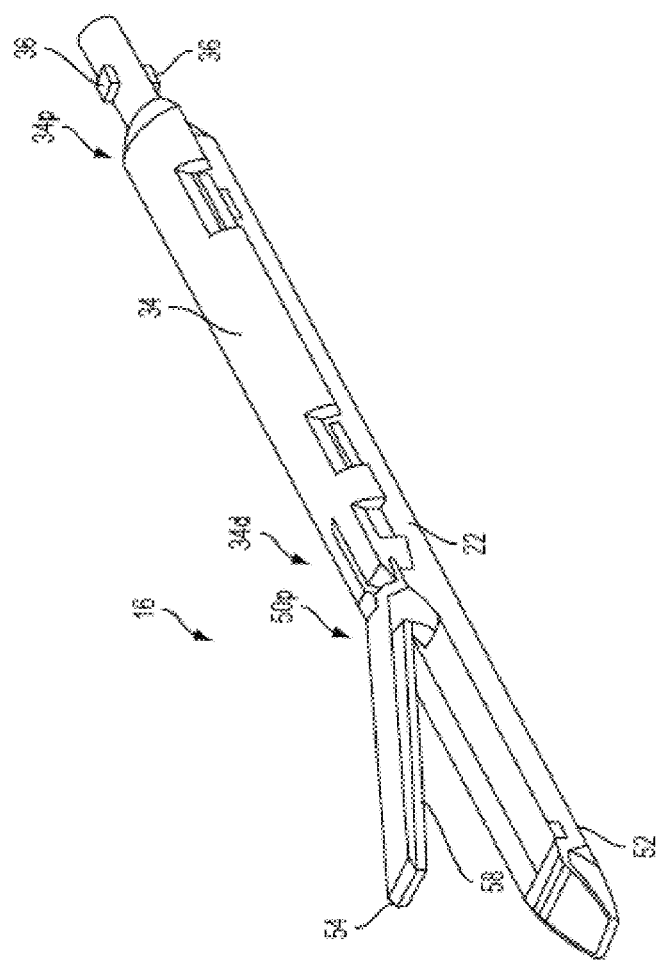
FIG. 3 is a perspective view of the attachment portion of FIG. 2 including at least one piece of adjunct material.

As shown in FIG. 3, the attachment portion 16 can include a proximal housing portion 34 at a proximal end 16p thereof and an end effector or tool 50 at a distal end 16d thereof. In the illustrated embodiment, the proximal housing portion 34 includes on a proximal end 34p thereof engagement nubs 36 for releasably engaging the shaft 14. The nubs 36 form a bayonet type coupling with the distal end 14d of the shaft 14. Besides nubs 36, any number of other complementary mating features can be used to allow the attachment portion 16 to be removably coupled to the shaft 14.

Figure 4:
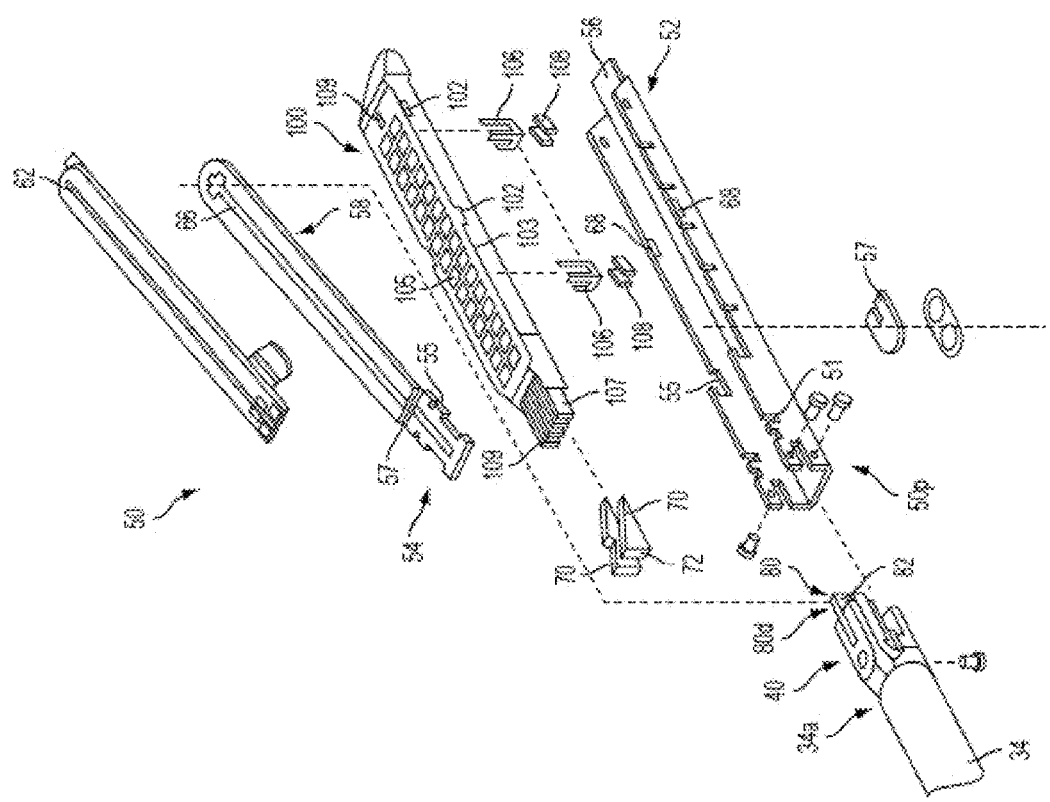
FIG. 4 is an exploded perspective view of the end effector of FIG. 3 with the adjunct material removed.

A distal end 34d of the proximal housing portion 34 can include a mounting assembly 40 pivotally secured thereto. As shown in FIG. 4, the mounting assembly 40 can be configured to receive a proximal end 50p of the end effector 50 such that pivotal movement of the mounting assembly 40 about an axis perpendicular to the longitudinal axis of the housing portion 34 effects articulation of the end effector 50 about a pivot member or pin 42. This pivotal movement can be controlled by the actuation lever 26 of the handle assembly 28, with components being disposed between the lever 26 and the mounting assembly 40 to allow for movement of the lever 26 to articulate the mounting assembly 40, and thereby the end effector 50. Similar to the firing system of the instrument 10, a person skilled in the art will recognize various configurations of components for effecting articulation, mechanical or otherwise, and thus a detailed explanation of the same is unnecessary. Some exemplary embodiments of components for effecting articulation that are suitable for use with the disclosures herein are provided for in patents and patent applications incorporated by reference elsewhere in the present application.

Figure 6:
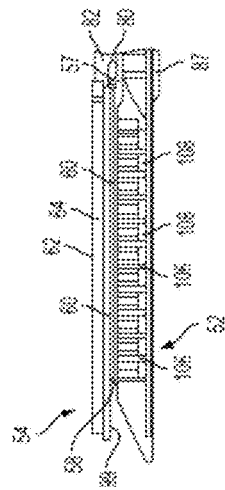
FIG. 6 is a side cross-sectional view taken along the section line indicated in FIG. 5.

The end effector 50 of the illustrated embodiment is a surgical stapling tool having a first, lower jaw 52 that serves as a cartridge assembly or carrier and an opposed second, upper jaw 54 that serves as an anvil. As shown in FIG. 6, an inner surface 58 of the second jaw 54, sometimes referred to as an anvil portion, can include a plurality of staple deforming cavities 60 and a cover plate 62 secured to a top surface 59 of the jaw 54 to define a cavity 64 therebetween. The cover plate 62 can help to prevent pinching of tissue during clamping and firing of the surgical stapler. The cavity 64 can be dimensioned to receive a distal end 80d of the axial drive assembly 80. A longitudinal slot 66 can extend through the anvil portion 58 to facilitate passage of a retention flange 82 of the axial drive assembly 80 into the anvil cavity 64. A camming surface 57 formed on the anvil portion 58 can be positioned to engage the axial drive assembly 80 to facilitate clamping of tissue 99. A pair of pivot members 53 formed on the anvil portion 54 can be positioned within slots 51 formed in the carrier 52 to guide the anvil portion between the open and clamped positions. A pair of stabilizing members can engage a respective shoulder 55 formed on the carrier 52 to prevent the anvil portion 54 from sliding axially relative to the staple cartridge 100 as the camming surface 57 is deformed. In other embodiments, the carrier 52 and staple cartridge 100 can be pivoted between open and clamped positions while the anvil portion 54 remains substantially stationary.

Figure 5:
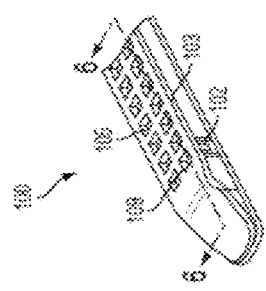
FIG. 5 is a detailed perspective view of a distal end of a staple cartridge for use with the end effector of FIG. 4.
Figure 8:
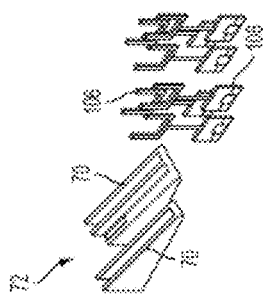
FIG. 8 is an exploded perspective view of an actuation sled, pushers, and fasteners of the surgical instrument of FIG. 4.
Figure 7:
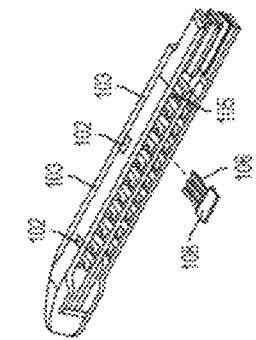
FIG. 7 is a bottom perspective view of the staple cartridge of FIG. 5.

The elongated support channel 56 of the first jaw 52 can be dimensioned and configured to receive a staple cartridge 100, as shown in FIGS. 4, 5, and 7. Corresponding tabs 102 and slots 68 formed along the staple cartridge 100 and the elongated support channel 56, respectively, function to retain the staple cartridge 100 within the support channel 56. A pair of support struts 103 formed on the staple cartridge 100 can be positioned to rest on sidewalls of the carrier 52 to further stabilize the staple cartridge 100 within the support channel 56. The staple cartridge 100 can also include retention slots 105 for receiving a plurality of fasteners 106 and pushers 108. A plurality of spaced apart longitudinal slots 107 can extend through the staple cartridge 100 to accommodate upstanding cam wedges 70 of an actuation sled 72 of a firing system (FIGS. 4 and 8). A central longitudinal slot 109 can extend along the length of the staple cartridge 100 to facilitate passage of a knife blade 81 associated with the axial drive assembly 80. During operation of the surgical stapler, the actuation sled 72 translates through longitudinal slots 107 of the staple cartridge 100 to advance cam wedges 70 into sequential contact with pushers 108, thereby causing the pushers 108 to translate vertically within the retention slots 105 and urge the fasteners 106 from the slots 105 into the staple deforming cavities 60 of the anvil portion 54.

An alternative embodiment of an attachment portion 16' is shown in FIGS. 9 and 10. The attachment portion 16' can include a proximal housing portion 34' at a proximal end 16p' thereof and an end effector or tool 50' at a distal end 16d' thereof. Nubs 36' can be provided to removably couple the attachment portion 16' to a shaft of a surgical instrument, and a mounting assembly 40' can be provided to removably and/or pivotally couple an end effector or tool 50' to the proximal housing portion 34'. The end effector 50' can include a first, lower jaw 52' that serves as a cartridge assembly, and a second, upper jaw 54' that serves as an anvil portion. The first jaw 52' can have many of the same features as the first jaw 52 of FIGS. 3, 4, and 6, and thus can include an elongated support channel 56' that is dimensioned and configured to receive a staple cartridge 100', and slots 68' configured to correspond with tabs 102' of the staple cartridge 100' to retain the cartridge 100' within the channel 56'. Likewise, the cartridge 100' can include support struts 103' to rest on sidewalls of the jaw 52', retention slots 105' for receiving a plurality of fasteners 106' and pushers 108', a plurality of spaced apart longitudinal slots 107' to accommodate upstanding cam wedges 70' of an actuation sled 72' of a firing system, and a central longitudinal slot 109' to facilitate passage of a knife blade 81' associated with an axial drive assembly 80'.

Similar to the second jaw 54 of FIGS. 3, 4, and 6, the second jaw 54' can include a cover plate 62' secured to a top surface of the jaws to define a cavity therebetween. An anvil plate 58' can serve as the inner surface of the jaw 54', and can include a longitudinal slot 66' for receiving a distal end of the axial drive assembly 80', and a plurality of staple deforming pockets or cavities (not shown) to form staples ejected from the cartridge 100'. In this embodiment, however, the lower jaw 52' containing the cartridge 100' is configured to pivot toward the upper jaw 54' while the upper jaw 54' remains substantially stationary upon actuation by a handle assembly and related components.

Figure 11:
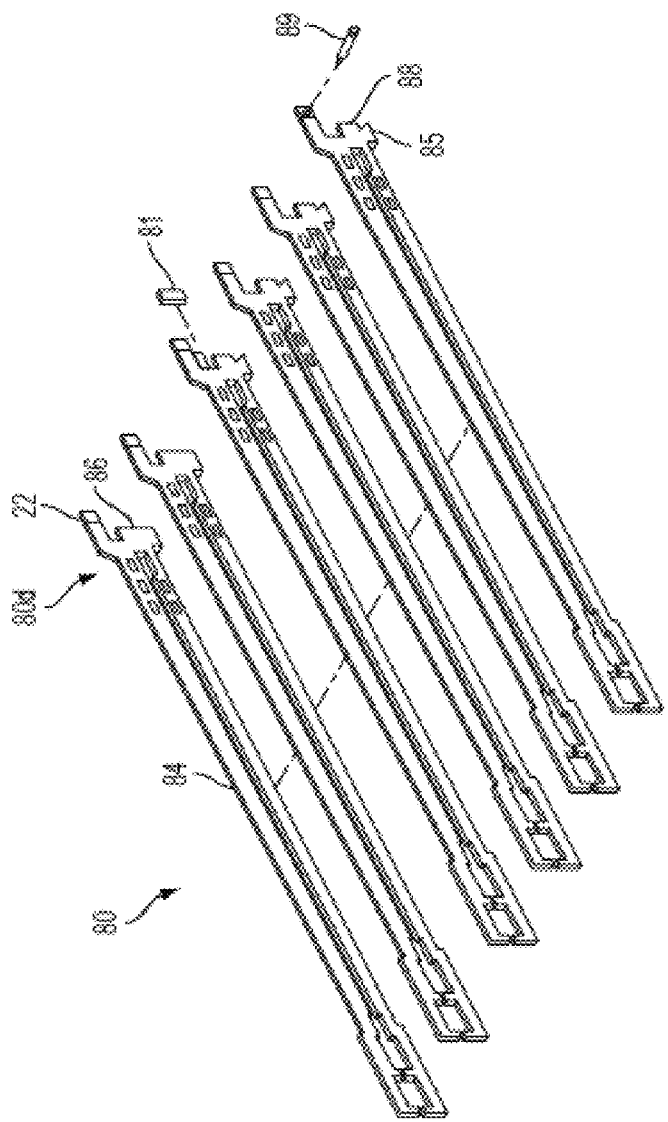
FIG. 11 is an exploded view of a drive assembly for use with the end effector of FIG. 4.

The end effector and staple cartridge disposed therein is configured to receive an axial drive assembly. One non-limiting exemplary embodiment of the axial drive assembly 80 is illustrated in FIG. 11. As shown, a distal end of a drive beam 84 can be defined by a vertical support strut 86 that supports the knife blade 81, and an abutment surface 88 configured to engage the central portion of the actuation sled 72 during a stapling procedure. Bottom surface 85 at the base of the abutment surface 88 can be configured to receive a support member 87 slidably positioned along the bottom of the staple cartridge 100 (FIGS. 4 and 6). The knife blade 81 can be positioned to translate slightly behind the actuation sled 72 through the central longitudinal slot 109 in the staple cartridge 100 to form an incision between rows of stapled body tissue. The retention flange 82 can project distally from the vertical strut 86 and can support a cylindrical cam roller 89 at its distal end. The cam roller 89 can be dimensioned and configured to engage the camming surface 57 on the anvil portion 58 to clamp the anvil portion 58 against body tissue. A person skilled in the art will recognize that a drive assembly for use in conjunction with surgical staplers or other surgical instruments can have many other configurations than the one illustrated in FIG. 11, some of which are described in patents and patent applications incorporated by reference elsewhere in the present application. By way of non-limiting example, the drive assembly 80 can include a single drive beam, or any other number of drive beams, and the distal end of the drive beam(s) can have any number of shapes that are configured for use in the end effector through which the drive assembly is configured to travel.

In use, the surgical stapler can be disposed in a cannula or port and disposed at a surgical site. A tissue to be cut and stapled can be placed between the jaws 52, 54 of the surgical stapler 10. Features of the stapler 10, such as the rotating knob 24 and the actuation lever 26, can be maneuvered as desired by the clinician to achieve a desired location of the jaws 52, 54 at the surgical site and the tissue with respect to the jaws 52, 54. After appropriate positioning has been achieved, the trigger 20 can be pulled toward the stationary handle 22 to actuate the firing system. The trigger 20 can cause components of the firing system to operate such that the control rod 32 advances distally through at least a portion of the shaft 14 to cause at least one of the jaws 52, 54 to collapse towards the other to clamp the tissue disposed therebetween and/or to drive the drive assembly 80 distally through at least a portion of the end effector 50.

In some embodiments, a first firing of the trigger 20 can cause the jaws 52, 54 to clamp the tissue, while subsequent firings of the trigger 20 can cause the drive assembly 80 to be advanced distally through at least a portion of the end effector 50. A single, subsequent firing can fully advance the drive assembly 80 through the staple cartridge 100 to eject the staples in the row, or alternatively, the components in the handle assembly 12 can be configured such that multiple, subsequent firings are required to fully advance the drive assembly 80 through the staple cartridge 100 to eject the staples in the row. Any number of subsequent firings can be required, but in some exemplary embodiments anywhere from two to five firings can fully advance the drive assembly 80 through the staple cartridge 100. In embodiments in which the drive assembly 80 includes the knife 81 to cut the tissue being stapled, the knife 81 cuts tissue as the drive assembly advances distally through the end effector 50, and thus the staple cartridge 100 disposed therein. In other exemplary embodiments, a motor disposed within the handle assembly 12 and associated with a firing trigger can actuate the drive assembly 80 automatically in response to activation of the firing trigger.

After the drive assembly 80 has been advanced distally through the staple cartridge 100, the retraction knobs 28 can be advanced proximally to retract the drive assembly 80 back towards its initial position. In some configurations, the retraction knobs 28 can be used to retract the drive assembly 80 prior to fully advancing the assembly 80 through the cartridge 100. In other embodiments retraction of the drive assembly 80 can be automated to occur after a predetermined action. For example, once the drive assembly 80 has distally advanced to its desired location, the subsequent return of the trigger 80 back to a biased open position can cause the drive assembly 80 to automatically retract. A motor and associated components, rather than retraction knobs 28 and associated components, can be used to retract the drive assembly 80. Further, as discussed above, other features, such as a firing lockout mechanism, an anti-reverse clutch mechanism, and an emergency return button, can be relied upon during operation of the surgical stapler 10, as would be understood by those skilled in the art.

The illustrated embodiment of a surgical stapling instrument 10 provides one of many different configurations, and associated methods of use, that can be used in conjunction with the disclosures provided herein. Additional exemplary embodiments of surgical staplers, components thereof, and their related methods of use, that can be used in accordance with the present disclosure include those devices, components, and methods provided for in U.S. Patent Application Publication No. 2012/0083835 and U.S. Patent Application Publication No. 2013/0161374, each of which is incorporated by reference herein in its entirety.

Implantable Materials

Regardless of the configuration of the surgical instrument, the present disclosure provides for the use of implantable materials, e.g., biologic materials and/or synthetic materials, collectively "adjunct materials," in conjunction with instrument operations. As shown in FIGS. 12 and 13, the end effector 50 can include at least one piece of adjunct material 200, 200' positioned intermediate the first and second jaw members 52, 54 and it can be releasably retained to one of the support channel 56 and/or the anvil portion 58. In the illustrated embodiment, the releasable retention is provided by retention members 202, 202', which are described in further detail below. In at least one embodiment, a surface on the adjunct material 200, 200' can be configured to contact tissue as the tissue is clamped between the first and second jaw members 52, 54. In such an embodiment, the adjunct material can be used to distribute the compressive clamping force over the tissue, remove excess fluid from the tissue, and/or improve the purchase of the staples. In various embodiments, one or more pieces of adjunct material can be positioned within the end effector 50. In at least one embodiment, one piece of adjunct material 200 can be attached to the staple cartridge 100 (FIG. 12) and one piece of adjunct material 200' can be attached to the anvil portion 58 (FIG. 13). In at least one other embodiment, two pieces of adjunct material 200 can be positioned on the support channel 56 and one piece of adjunct material 200' can be positioned on the anvil portion 58, for example. Any suitable number of adjunct materials can be situated within the end effector 50.

Adjunct material used in conjunction with the disclosures provided for herein can have any number of configurations and properties. Generally, they can be formed from of a bioabsorbable material, a biofragmentable material, and/or a material otherwise capable of being broken down, for example, such that the adjunct material can be absorbed, fragmented, and/or broken down during the healing process. In at least one embodiment, the adjunct material can include a therapeutic drug that can be configured to be released over time to aid the tissue in healing, for example. In further various embodiments, the adjunct materials can include a non-absorbable and/or a material not capable of being broken down, for example. Similarly, the connection or retention members can be at least partially formed from at least one of a bioabsorbable material, a biofragmentable material, and a material capable of being broken down such that the connection or retention members can be absorbed, fragmented, and/or broken down within the body. In various embodiments, the connection or retention members can include a therapeutic drug that can be configured to be released over time to aid the tissue in healing, for example. In further various embodiments, the connection or retention members can include a non-absorbable and/or a material not capable of being broken down, for example, such as a plastic.

More particularly, some exemplary, non-limiting examples of synthetic materials that can be used in conjunction with the disclosures provided for herein include biodegradable synthetic absorbable polymer such as a polydioxanone film sold under the trademark PDS® or with a Polyglycerol sebacate (PGS) film or other biodegradable films formed from PGA (Polyglycolic acid, marketed under the trade mark Vicryl), PCL (Polycaprolactone), PLA or PLLA (Polylactic acid), PHA (polyhydroxyalkanoate), PGCL (poliglecaprone 25, sold under the trademark Monocryl), PANACRYL (Ethicon, Inc., Somerville, N.J.), Polyglactin910, Poly glyconate, PGA/TMC (polyglycolide-trimethylene carbonate sold under the trademark Biosyn), polyhydroxybutyrate (PHB), poly(vinylpyrrolidone) (PVP), poly(vinyl alcohol) (PVA), or a blend of copolymerization of the PGA, PCL, PLA, PDS monomers. In use, the synthetic material can be broken down by exposure to water such that the water attacks the linkage of a polymer of the synthetic material. As a result, the mechanical strength can become diminished, and a construct of the material can be broken down into a mushy or fractured scaffold. As further breakdown occurs such that the material breaks into carbohydrates and acid constituents, a patient's body can metabolize and expel the broken down materials.

Some exemplary, non-limiting examples of biologic derived materials that can be used in conjunction with the disclosures provided for herein include platelet poor plasma (PPP), platelet rich plasma (PRP), starch, chitosan, alginate, fibrin, thrombin, polysaccharide, cellulose, collagen, bovine collagen, bovine pericardium, gelatin-resorcin-formalin adhesive, oxidized cellulose, mussel-based adhesive, poly (amino acid), agarose, polyetheretherketones, amylose, hyaluronan, hyaluronic acid, whey protein, cellulose gum, starch, gelatin, silk, or other material suitable to be mixed with biological material and introduced to a wound or defect site, including combinations of materials, or any material apparent to those skilled in the art in view of the disclosures provided for herein. Biologic materials can be derived from a number of sources, including from the patient in which the biologic material is to be implanted, a person that is not the patient in which the biologic material is to be implanted, or other animals.

Additional disclosures pertaining to synthetic or polymer materials and biologic materials that can be used in conjunction with the disclosures provided herein can be found in U.S. Patent Application Publication No. 2012/0080335, U.S. Patent Application Publication No. 2012/0083835, U.S. patent application Ser. No. 13/433,115, entitled "Tissue Thickness Compensator Comprising Capsules Defining a Low Pressure Environment," and filed on Mar. 28, 2012, U.S. patent application Ser. No. 13/433,118, entitled "Tissue Thickness Compensator Comprised of a Plurality of Materials," and filed on Mar. 28, 2012, U.S. patent application Ser. No. 13/532,825, entitled "Tissue Thickness Compensator Having Improved Visibility," and filed on Jun. 26, 2012, U.S. patent application Ser. No. 13/710,931, entitled "Electrosurgical End Effector with Tissue Tacking Features," and filed on Dec. 11, 2012, and U.S. patent application Ser. No. 13/763,192, entitled "Multiple Thickness Implantable Layers for Surgical Stapling Devices," and filed on Feb. 8, 2013, each of which is incorporated by reference herein in its entirety.

In use, the adjunct material can come pre-loaded onto the device and/or the staple cartridge, while in other instances the adjunct material can be packaged separately. In instances in which the adjunct material comes pre-loaded onto the device and/or the staple cartridge, the stapling procedure can be carried out as known to those skilled in the art. For example, in some instances the firing of the device can be enough to disassociate the adjunct material from the device and/or the staple cartridge, thereby requiring no further action by the clinician. In other instances any remaining connection or retention member associating the adjunct material with the device and/or the staple cartridge can be removed prior to removing the instrument from the surgical site, thereby leaving the adjunct material at the surgical site. In instances in which the adjunct material is packaged separately, the material can be releasably coupled to at least one of a component of the end effector and the staple cartridge prior to firing the device. The adjunct material may be refrigerated, and thus removed from the refrigerator and the related packaging, and then coupled to the device using a connection or retention member as described herein or otherwise known to those skilled in the art. The stapling procedure can then be carried out as known to those skilled in the art, and if necessary, the adjunct material can be disassociated with the device as described above.

Retention Members

Connection or retention members can be used to secure, at least temporarily, one or more pieces of adjunct material onto an end effector and/or staple cartridge. These retention members can come in a variety of forms and configurations, such as one or more sutures, adhesive materials, staples, brackets, snap-on or other coupling or mating elements, etc. For example, the retention members can be positioned proximate to one or more sides and/or ends of the adjunct material, which can help prevent the adjunct material from peeling away from the staple cartridge and/or the anvil face when the end effector is inserted through a trocar or engaged with tissue. In still other embodiments, the retention members can be used with or in the form of an adhesive suitable to releasably retain the adjunct material to the end effector, such as cyanoacrylate. In at least one embodiment, the adhesive can be applied to the retention members prior to the retention members being engaged with the adjunct material, staple cartridge, and/or anvil portion. Generally, once firing is completed, the retention member(s) can be detached from the adjunct material and/or the end effector so that the adjunct material can stay at the surgical site when the end effector is removed. Some exemplary, non-limiting embodiments of retention members are described herein with respect to FIGS. 12-15.

FIG. 12 illustrates one exemplary embodiment of a connection or retention member 202 associated with the adjunct material 200 to secure the material 200 at a temporary location with respect to the lower jaw 52 of the end effector 50. As shown, the adjunct material 200 is disposed over the staple cartridge 100 located in the elongate channel 56 of the lower jaw 52, and the retention member 202 extends therethrough. In the embodiment, the retention member 202 is in the form of a single suture stitched through multiple locations of the adjunct material 200, or it can be multiple sutures disposed at one or more locations on the adjunct material 200. As shown, the sutures are positioned at locations around a perimeter of the adjunct material 200, and are also adjacent to a central longitudinal channel 201 formed in the adjunct material 200. The channel 201 can make it easier for a knife passing through the adjunct material 200 to cut the material 200 into two or more separate strips. In some embodiments, for instance when the retention member 202 is a single suture threaded through multiple locations of the adjunct material 200, a knife passing through the lower jaw 52 can cut the retention member 202 at one or more locations, thereby allowing the retention member 202 to be disassociated from the adjunct material 200 and removed from the surgical site while the adjunct material 200 remains held at the surgical site by one or more staples ejected from the cartridge 100.

FIG. 13 illustrates another embodiment of a connection or retention member 202' associated with the adjunct material 200' to secure the material 200' at a temporary location on the end effector 50. The retention member 202' has the same configuration as the retention member 202 in FIG. 12, however, in this embodiment it is used to secure the material to the anvil or upper jaw 54, rather than the cartridge or lower jaw 52.

FIG. 14 illustrates another, non-limiting embodiment of a connection or retention member 202" used to releasably retain an adjunct material 200" to at least one of the upper jaw 54 and the lower jaw 52. In this embodiment, the retention member 202" is a single suture that extends through a distal portion 200d" of the adjunct material 200" and is coupled to a proximal end 54p of the upper jaw 54. Terminal ends 202t" of the retention member 202" can be used to move the retention member 202" with respect to the jaws 54, 52. In its extended position, which is illustrated in FIG. 14, the retention member 202" can hold the adjunct material 200" in position as the end effector 50 is inserted into a surgical site. Thereafter, the jaws 52, 54 of the end effector 50 can be closed onto tissue, for example, and staples from the staple cartridge 100 can be deployed through the adjunct material 200" and into the tissue. The retention member 202" can be moved into its retracted position such that the retention member 202" can be operably disengaged from the adjunct material 200". Alternatively, the retention member 202" can be retracted prior to the staples being deployed. In any event, as a result of the above, the end effector 50 can be opened and withdrawn from the surgical site leaving behind the adjunct material 200" and tissue.

FIG. 15 illustrates yet another, non-limiting embodiment of a connection or retention member 202'" for securing a location of adjunct material 200'" to an end effector. In particular, the adjunct material 200'" and retention member 202'" are used in conjunction with the end effector 50' of FIGS. 9 and 10. In this embodiment, the retention member 202'" is in the form of a suture that is used to tie the adjunct material 200'" to the first, lower jaw 52' at proximal and distal ends thereof 52p', 52d'. Similarly, as shown in FIGS. 9 and 10, the adjunct material 200'" can also be secured to the second, upper jaw 54' at proximal and distal ends thereof 54p', 54d'. Optionally, recesses can be formed in either or both of the jaws 52', 54', and either or both of the adjunct materials 200'", which can protect the retention members 202'" against unintended cutting by an outside object. In use, the knife blade 81' on the driver assembly 80' can incise the retention members 202'" as it passes through the end effector 50' to release the adjunct material 200'".

A person skilled in the art will recognize a variety of other ways by which the adjunct material can be temporarily retained with respect to the end effector. In various embodiments a connection or retention member can be configured to be released from an end effector and deployed along with a piece of adjunct material. In at least one embodiment, head portions of retention members can be configured to be separated from body portions of retention members such that the head portions can be deployed with the adjunct material while the body portions remain attached to the end effector. In other various embodiments, the entirety of the retention members can remain engaged with the end effector when the adjunct material is detached from the end effector.

Tissue Ingrowth Materials

As indicated above, various adjunct materials are provided for use with a surgical stapler. While in some instances the adjunct materials can be a synthetic material and/or a biologic material, in some exemplary embodiments the adjunct material can be especially configured to facilitate tissue ingrowth into the materials. While this can be achieved using various techniques, in one embodiment the adjunct material can include both hydrophilic portions and hydrophobic portions to form a hydrophilic-hydrophobic adjunct material. The resulting combination can advantageously have surfaces or portions that attract cells and encourage cell ingrowth (hydrophilic) and surfaces or portions that do not attract cells or otherwise encourage cell ingrowth (hydrophobic). In use, the hydrophobic portions can be placed in contact with the tissue, while the hydrophobic portions can be oriented away from the tissue surface.

In certain embodiments, synthetic polymers used to form adjunct materials can be hydrophobic, such as polycaprolactone (PCL) and polylactic acid (PLLA). It is noted that "polymers" as used herein can include copolymers. Synthetic adjunct materials, however, can be treated or otherwise produced to be hydrophilic, as will be discussed herein. To form the adjunct material, any method of creating a synthetic material having a hydrophilic portion and a hydrophobic portion can be used. In some embodiments, a surface of (or only half of) a hydrophobic adjunct material is treated with an acid or base which can cause the formation of pockets or pits in the surface. Alternatively, the adjunct material can be formed by bonding a hydrophilic layer to a hydrophobic layer. For example, an adjunct material can be treated such that the entire adjunct material becomes hydrophilic. Then this hydrophilic layer can be bound, such as by laminating, to a second hydrophobic adjunct material layer creating a material that is hydrophobic and hydrophilic. Various approaches can be used to create an adjunct material or matrix where a tissue contacting portion encourages cellular ingrowth while a non-tissue contacting portion discourages cellular ingrowth.

Any adjunct material, such as those described above, can be made hydrophilic and/or hydrophobic. Additionally, a person skilled in the art will appreciate that any form of adjunct material can be made to be hydrophilic and/or hydrophobic, for example a film type adjunct material and/or a foam type adjunct material. In one exemplary embodiment, a film or foam can be made hydrophilic using any suitable technique, such as surface grafting techniques and coating techniques, depending upon the physical or chemical characteristics of the film or foam.

Surface grafting techniques can be employed, for example, if the film or foam has reactive chemical sites or functionalities such as amino, hydroxyl or carboxyl groups. If this is the case, the film or foam can be made hydrophilic by covalently binding hydrophilic moieties or surfactants onto the film or foam. These hydrophilic moieties can include, but are not limited to, polyethylene glycol (PEG) and poloxamers (available under the trade names Pluronic® available from BASF, Synperonic® available from Sigma Aldrich, and Kolliphor available from BASF).

Coating techniques can be used, for example, if the film or foam does not have any reactive sites as it will generally not be possible to impart the hydrophilic characteristics using surface grating techniques. Various levels of coating with a hydrophilic polymer will impart varying degrees of hydrophilicity to the foam or film. However, care needs to be taken in the case of porous foam since coating can result in closing of the open pores and may result in conversion of open cell or reticulated foam to closed cell foam.

In one embodiment, hydrophilic 65:35 PGA/PCL polymers can be prepared by copolymerizing PEG/Pluronic with PCL/PGA. Introduction of PEG or poloxamer repeat units in the copolymer backbone can render the backbone hydrophilic resulting in swelling upon contact with body fluids including blood. The hydrophilicity of the polymer can be controlled by using various molecular weights of PEG and poloxamers and the ratio of PEG/poloxamer to PCL/PGA. For example, higher content of PEG/poloxamer is expected to result in higher swelling and higher hydrophilicity.

Figure 16:
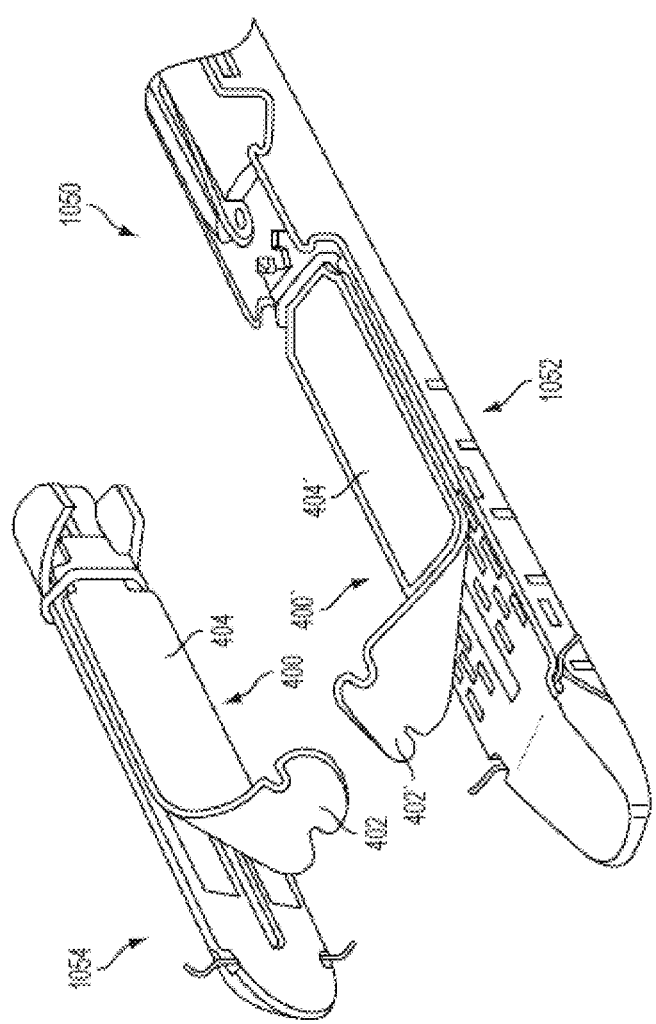
FIG. 16 is a perspective view of portions of an end effector having an adjunct material associated therewith.

An adjunct material can be selectively attached to either or both jaws of an end effector. As shown in FIG. 16, an adjunct material 400, 400' can be attached to both lower and upper jaws 1052, 1054 of an end effector 1050. The adjunct material 400, 400' can have a first side 402, 402' that is hydrophobic and a second side 404, 404' that is hydrophilic. The first, hydrophobic side 402, 402' can be configured to face and directly contact the upper and lower jaws 1052, 1054, while the second, hydrophilic side 404, 404' can be oriented away from the upper and/or lower jaws 1052, 1054. In this configuration, the second hydrophilic side 404, 404' will face and directly contact the tissue being treated (i.e., grasped by the end effector 1050) once the end effector 1052 is actuated, and the first, hydrophobic side 402, 402' will be on an opposite side facing away from the tissue being treated or grasped. This configuration is illustrated in FIGS. 18A and 18B, as will be discussed in detail below.

Figure 17A:
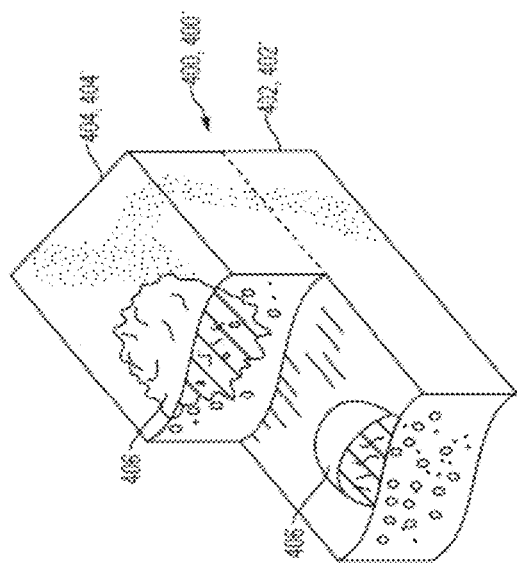
FIG. 17A is a partial cutaway view of an exemplary adjunct material having a drop of water disposed thereon.
Figure 17C:
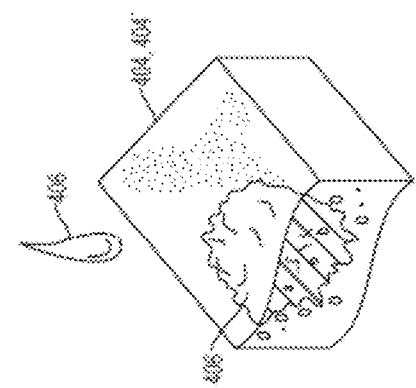
FIG. 17C is a cross-sectional view of an exemplary hydrophilic adjunct material having a drop of water disposed thereon.
Figure 17B:
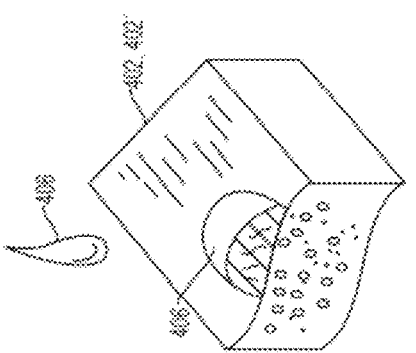
FIG. 17B is a partial cutaway view of an exemplary hydrophobic adjunct material having a drop of water disposed thereon.

FIGS. 17A-17C illustrate the adjunct material 400, 400' when wetted by a drop of water 406. As shown, the hydrophilic side 404, 404' absorbs the water 406 and disperses the water 406 through the layer 404, 404'. In contrast, the hydrophobic side 402, 402' repels the water 406, which remains substantially on the surface of the hydrophobic layer 402, 402'.

Figure 18A:
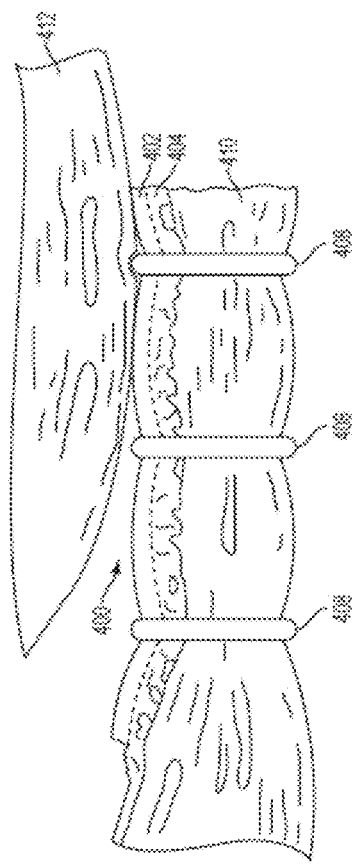
FIG. 18A is a side view of an adjunct material maintained adjacent a tissue to be treated and an adjacent organ by staples.
Figure 18B:
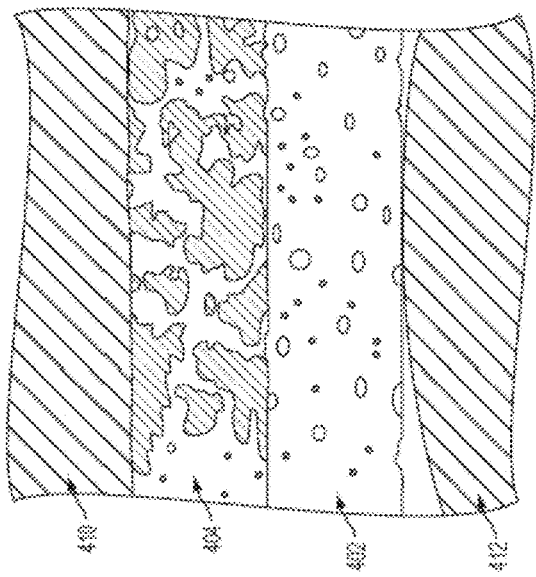
FIG. 18B is a cross-sectional view of an exemplary adjunct material disposed between a tissue to be treated and an adjacent organ.

In use, the adjunct material 400 can be positioned in a body, such as is shown in FIGS. 18A and 18B. As shown in FIG. 18A, the adjunct material 400 is implanted at a treatment site using staples 408 such that the hydrophilic side 404 of the adjunct material 400 is directly contacting the tissue to be treated 410 and the hydrophobic side 402 on an opposite side and is exposed to an adjacent tissue 412, such as an organ where tissue ingrowth is not desired. In this configuration, the hydrophilic side 404 enhances cellular ingrowth into the grasped tissue 410 and the hydrophobic side 402 discourages cellular ingrowth and therefore prevents the hydrophobic side from attaching to adjacent tissue 412. FIG. 18B illustrates this further as the hydrophilic side 404 is in contact with the tissue to be treated 410, but not the adjacent tissue 412 and the hydrophobic side is in contact with the adjacent tissue 412, but not the tissue to be treated 410.

Biologically Coated Synthetic Materials

As mentioned above, typically synthetic absorbable materials are hydrophobic and at best do not inhibit healing and at worst are treated like foreign bodies during healing. It is possible, however, to take a hydrophobic matrix, like PGA/PCL, and micro-etch or pit the surface of the polymer to make the material more hydrophilic. Once etched or pitted, it is further possible to deposit or coat the synthetic absorbable material with a biologic material, such as collagen or fibrin, so as to form an synthetic absorbable material that has a biologic coating, which enhances healing as a biologic but retains the structural properties of the synthetic absorbable material.

FIGS. 19A-19C illustrate various synthetic absorbable materials having surface features and characteristics, such as nanofeatures, that create a macro-structure that has the effect of creating a hydrophilic surface thus allowing for biologic coating. FIG. 19A depicts an adjunct material that is woven 500. The woven material creates surface features 502, i.e., pockets, that can entrap a biologic. Additionally, the woven adjunct material 500 can be formed of fibers 504 that are either hydrophilic or hydrophobic, or combinations thereof, which allow the woven material to be an hydrophilic-hydrophobic material, as well as enables it to have a biologic coating. FIG. 19B depicts a synthetic absorbable material 500' that has micro-etched surface features 502' that are produced using a laser etching technique. These surface features 502' similarly provide hydrophilic surface features on the synthetic absorbable material. FIG. 19C illustrates a synthetic absorbable material 500" that has been treated with a surface hydrolysis technique. This surface hydrolysis can be done through introduction of a strong acid or base that is then washed off or freeze dried away before it destroys the entire matrix. This surface hydrolysis results in surface pitting forming a macro-structure that creates a hydrophilic surface and thus encourages cellular ingrowth. Likewise weaving, laser etching, surface coating, plasma treatment, surface grafting, and/or blending can be done to improve the hydrophilic properties of the synthetic absorbable material. These surface etching and pitting techniques can not only make the adjunct material (or scaffold) hydrophilic, it can leave pitted surfaces that retain fluids once they are encourage to move into the structure.

Figure 21C:
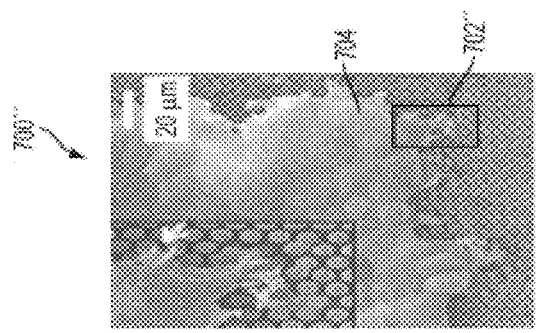
FIG. 21C is a scanning electron image of yet an exemplary adjunct material having surface features.
Figure 21B:
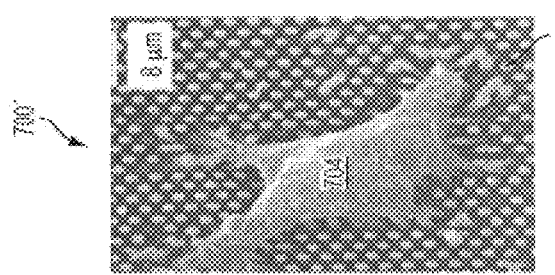
FIG. 21B is a scanning electron image of another exemplary adjunct material having surface features.
Figure 21A:
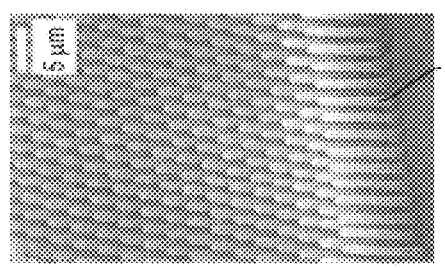
FIG. 21A is a scanning electron microscope image of an exemplary adjunct material having surface features.
Figure 22C:
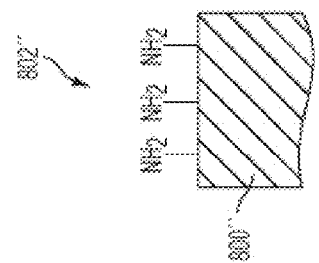
FIG. 22C is a perspective view of yet another exemplary adjunct material having surface features.
Figure 22B:
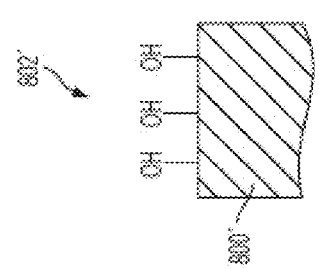
FIG. 22B is a perspective view of another exemplary adjunct material having surface features.
Figure 22A:
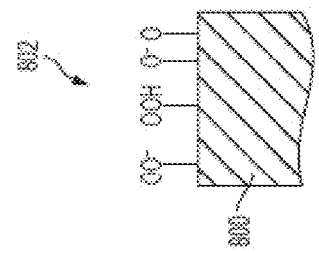
FIG. 22A is a perspective view of an exemplary adjunct material having surface features.

FIGS. 20A-20C are scanning electron microscope images of synthetic absorbable materials 600, 600', 600" having surface pitting 602, 602', 602". FIGS. 21A-21C are scanning electron microscope images of synthetic absorbable materials 700, 700', 700" having micro-etched nanofeatures 702, 702', 702" on their surface. As shown in FIGS. 21B and 21C, cells 704 adhere or attach to the nanofeatures 702', 702" and thus encourage cellular ingrowth. FIGS. 22A-22C illustrate additional surface features, i.e., function groups, 802, 802', 802" that can be formed on synthetic absorbable material 800, 800', 800" using plasma etching and/or polymer etching techniques. FIG. 22A shows the result of plasma etching and/or polymer grafting that occurs when oxidation in air occurs, FIG. 22B shows that hydroxyl groups 802' are formed when an aldehyde is used, and FIG. 22C shows that amine groups 802" are formed when diamines and blending are used.

Coating the micro-etched or pitted synthetic absorbable material can be achieved by any suitable method. For example, once the pitted or etched surface is formed, it can be saturated with a liquified collagen, fibrin, or other biologic material. Following saturation, the saturated synthetic absorbable adjunct material or scaffold can then be freeze dried or lyophilized to create a biologic surface coating that will be retained in the pits even after hydrating the adjunct material or scaffold. This biologically coated synthetic material can act like a biologic to in growing cells while still retaining desired synthetic properties, as discussed above.

Tissue Reinforcement Materials with Sealing Properties

The tissue reinforcement materials described herein can be embodied in a variety of different materials, including adjunct materials. While in various instances adjunct materials can be either a synthetic material or a biologic material, in various embodiments the adjunct material includes both synthetic material and biologic material (i.e., it is a hybrid adjunct material). The resulting combination can advantageously exhibit beneficial features from both types of materials in a single hybrid material. For example, a hybrid adjunct material can be designed to combine benefits of biologic material (such as improved healing and tissue growth) with desirable mechanical properties of synthetic material (such as elasticity or the ability to provide compression). In various embodiments, a synthetic material can also provide structure and support for a biologic material (e.g., add strength and/or shear resistance to fibrous biologic material), while still allowing the biologic material to contact a surgical site and support and/or promote healing. Further, hybrid adjunct materials can be configured to help reduce inflammation, promote cell growth, and/or otherwise improve healing. In various embodiments, adjunct material can be bioimplantable and/or bioabsorbable.

FIGS. 23-23C illustrate several views of an exemplary tissue reinforcement material having a plurality of fibers in a loop structure arrangement.

FIGS. 23 and 23A, show one exemplary tissue reinforcement material 1601 in accordance with the present disclosure. Here, the tissue reinforcement material 1601 is releasably retained on a portion of a surgical stapler end effector (see, e.g., FIGS. 1 and 10), shown in part by an anvil or upper jaw 1602, for delivery to tissue upon deployment of staples. The tissue reinforcement material 1601 includes a plurality of fibers 1603 having an arrangement configured to compress and seal around a fastener component (e.g., a surgical staple) inserted therethrough. One skilled in the art will appreciate that such compression and sealing properties can be beneficial in that they can prevent fluid (e.g., blood) leakage from around a staple leg. In this example, the arrangement is a loop structure of fibers, shown in further detail in magnified fibers 1603'. The fibers 1603, 1603' form the loop structure through the intertwining of the fibers 1603, 1603'.

FIG. 23C illustrates a single strand of fiber 1604 in a loop structure. In this example, the fiber 1604 was contacted with a liquid or gel and dried to form a membrane 1605 extending around the fiber 1604 and between loops in the fiber 1604. FIG. 23C illustrates a cross section AA taken along the plane AA in FIG. 23B, where the fiber 1604 is embedded in the membrane 1605. The fiber 1604 can be intertwined or woven with other fibers, or another portion of the same fiber 1604, to achieve the desired sealing properties.

While FIGS. 23 and 23A illustrate a particular loop structure of fibers 1603, 1603', and FIGS. 23B and 23C illustrate a particular single strand, a person skilled in the art will appreciate that a plurality of fibers can be arranged in number of alternative structures having an arrangement configured to compress and seal around a fastener component inserted therethrough (which may also be a function of other features or components of the tissue reinforcement material). Examples of alternative structures include weaves, interlocking and interconnecting patterns, as well as different loop structures. Exemplary patterns can in include two or more loop or weave structures. Likewise, patterns can include two or more types of fibers. Arrangements can be configured to allow the material to stretch and recover in response to penetration by a fastener component. Similarly, the plurality of fibers can be elastic. In various embodiments, the arrangement can advantageously provide a biologic material (e.g., woven biologic) with a desirable mechanical properties of a synthetic material.

Figure 24A:
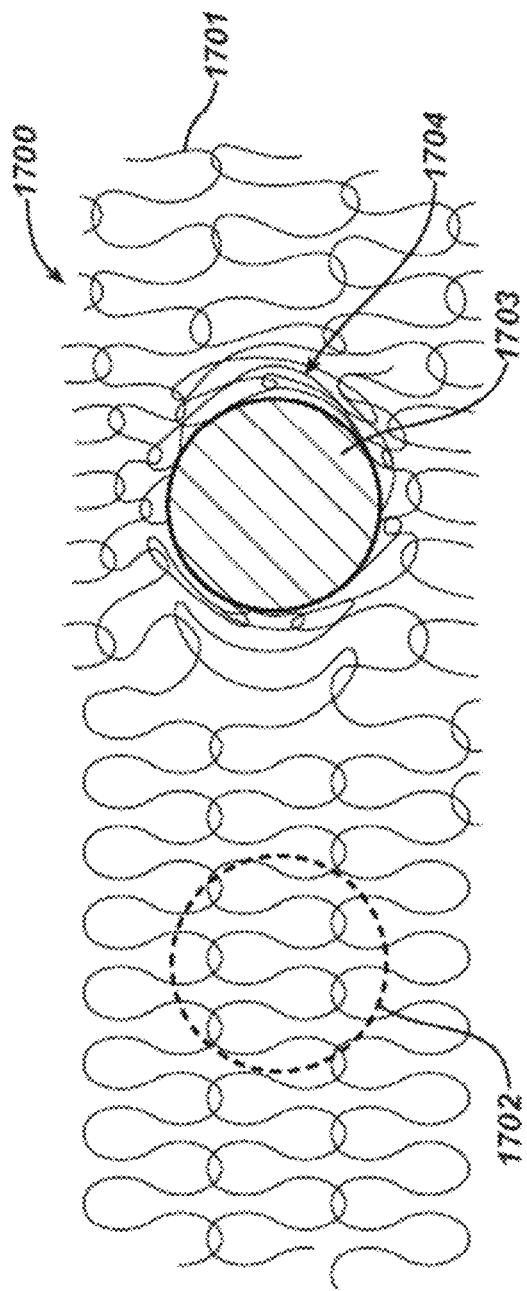
FIGS. 24A and B illustrate exploded views of an exemplary tissue reinforcement material having a plurality of fibers in a loop structure arrangement shown compressing and sealing around a fastener component.
Figure 24B:
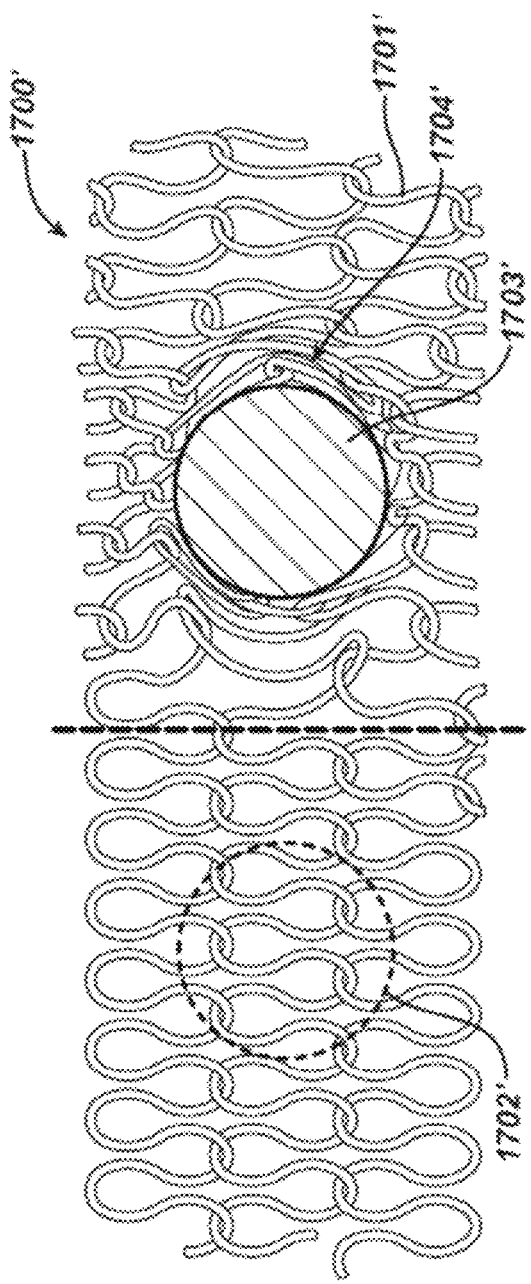

FIGS. 24A and 24B illustrate exemplary fiber arrangements configured to compress and seal around a fastener component (e.g., surgical staple) inserted therethrough. In these examples, the woven material 1700, 1700' includes a plurality of fibers 1701, 1701' having an intertwined loop structure arrangement. Dashed circle 1702, 1702' indicates a region of the woven material 1700, 1700' through which a fastener component (e.g., surgical staple) will be inserted. A person skilled in the art will recognize that while woven material 1700, 1700' has an essentially uniform arrangement, alternative materials having different patterns (e.g., a denser weave at a region through which a fastener component will be inserted) are encompassed by the present disclosure. As illustrated when a fastener component such as a staple leg 1703, 1703' is inserted through the woven material 1700, 1700', the weave in the region 1704, 1704' adjacent to the staple leg 1703, 1703' is distorted, for example through tightening and/or swelling, thereby sealing around the staple leg 1703, 1703'.

FIGS. 24A and 24B also illustrate that different types of fibers (e.g., in addition to different types of arrangements) can be employed to achieve the desired mechanical properties. For example, FIG. 24A shows a narrower, filamentous fiber 1701 as compared to FIG. 24B, which shows a thicker, textured fiber 1701'. As a result, the region 1704' adjacent to the staple leg 1703' in FIG. 24B exhibits greater tightening and/or swelling than region 1704 adjacent to the staple leg 1703 in FIG. 24A.

A person skilled in the art will recognize that the fiber arrangements shown in FIGS. 24A and 24B are non-limiting examples, and that alternative materials having different fiber types and combinations are also encompassed by the present disclosure. In various embodiments, the plurality of fibers include a biologic material. Further, in various embodiments, the plurality of fibers include a synthetic material. In some embodiments, the plurality of fibers includes both a biologic material and a synthetic material. The fiber can be a woven, spun, cast, or extruded fiber.

Figure 25:
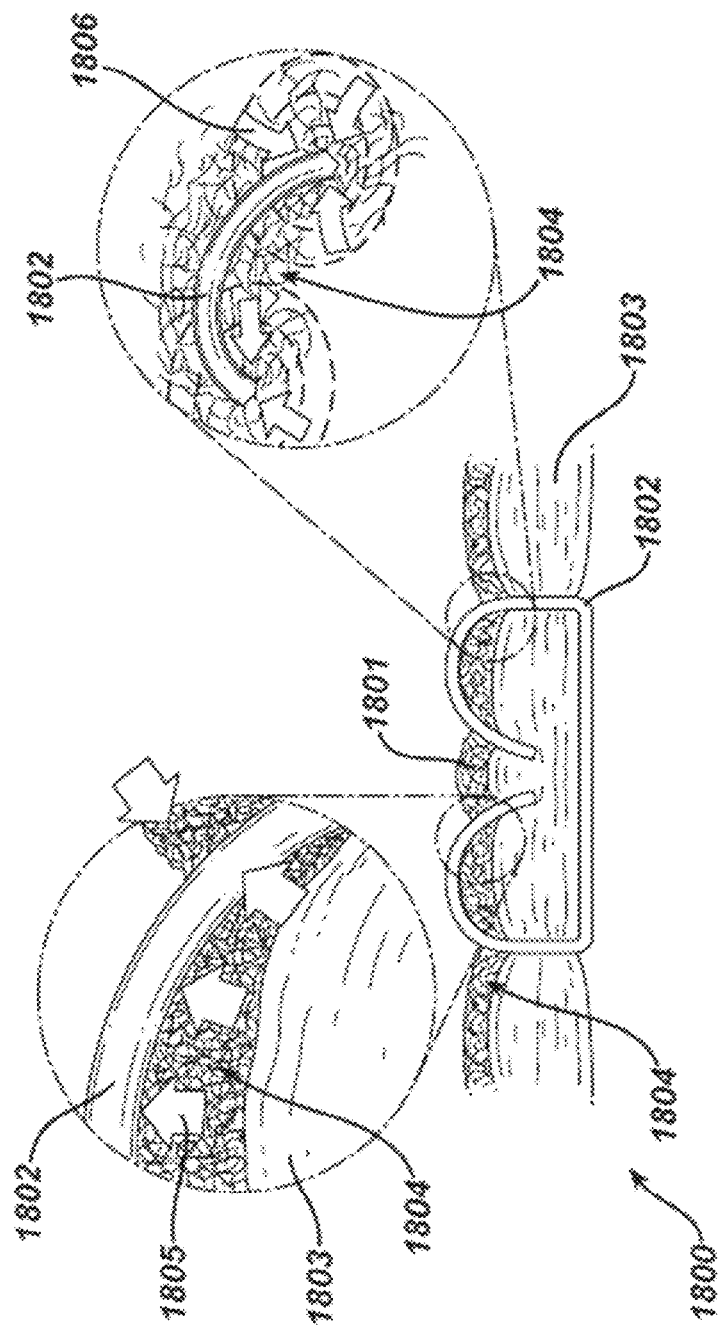
FIG. 25 illustrates another exemplary embodiment of a tissue reinforcement material having vertical and radial springiness.

FIG. 25 illustrates another exemplary embodiment 1800 of a tissue reinforcement material 1801 having vertical and radial springiness, which seals around a fastener 1802 inserted through the material 1801 and tissue 1803 (e.g., biologic tissue at a surgical site). As shown in FIG. 25 the tissue reinforcement material 1801 has been released from a portion of a surgical stapler end effector (not shown) and delivered to the tissue 1803 upon deployment of a staple 1802 from a surgical stapler (not shown). As shown, the tissue reinforcement material 1801 includes a plurality of fibers 1804 having an arrangement configured to compress and seal around the fastener 1802 inserted therethrough.

In contrast to the loop structure of fibers 1603, 1603', 1604, 1701, 1701' shown in FIGS. 23A-C and 24A-B, which seal around a fastener component largely through deformation, tightening, and/or swelling of the loop structure around the fastener component, the plurality of fibers 1804 shown in FIG. 25 have a three dimensional network pattern that has vertical springiness 1805 and radial springiness 1806, which seal around a fastener component 1802 largely through an elastic and/or spring force exerted by the fibers 1804 on the fastener component 1802. The vertical springiness 1805 and radial springiness 1806 of the plurality of fibers 1804 can be a result of the arrangement of fibers, the fiber material, or a combination thereof. A person skilled in the art will appreciate that other arrangement of fibers that can exert an elastic and/or spring force on the fastener component are possible, and are not limited to the exemplary embodiments of FIG. 25. Fibers of different materials and/or arrangements can be used to provide springiness. For example, springiness can be achieved in a tissue reinforcement material using vertical standing loops made of a relatively hard or resilient material like polyglactin 910 (available as VICRYL™ manufactured by Ethicon, Inc.), and the rest of the tissue reinforcement material can be made of a biologic or a relatively softer material, like poliglecaprone 25 (available as MONOCRYL™ manufactured by Ethicon, Inc.). The base of each standing loop can be knotted to an interwoven substrate providing an anchor and therefore more column force or springiness. In one embodiment, the standing fibers can also be woven in a reversing pattern where every other fiber is at an opposite angle (e.g., plus and minus 30 degrees from vertical). In such a pattern, alternating fibers can cancel out each other's off angle, which allows them to lay down and therefore support an upper woven structure from a lower structure in a truss format that provides vertical springiness.

Fibers can be selected based upon other physical properties. For example, in various embodiments, the material swells around the fastener component when the fastener component is inserted therethrough, to form a seal around the fastener component. In various embodiments, the material swells around the fastener component when the second material is wetted, to form a seal around the fastener component. In some embodiments, the material swells around the fastener component when the fastener component is inserted therethrough and when the material is wetted, to form a seal around the fastener component. Furthermore, in various embodiments, the material engages the fastener component when the fastener component is inserted therethrough to mitigate movement of the material and tissue adjacent the fastener component, relative to the fastener component. Fibers and arrangements thereof can also provide tissue reinforcement materials with other properties such as flexibility, an ability to stretch and recover, and/or an ability to release or elute one or more biologically active agents (e.g., drugs). Fibers can be, or include, biologic fibers. A person skilled in the art will recognize that the properties of the material (e.g., with respect to sealing) can be affected by components of the material in addition to the fibers.

In various embodiments, the tissue reinforcement material includes a biologic material. Likewise, the tissue reinforcement material can include a synthetic material. In various embodiments, the tissue reinforcement material can be formed in a single layer. For example, like the embodiment illustrated in FIG. 23, the material can have a single layer including the plurality of fibers. A single layer can include a biologic material and a plurality of fibers. In various embodiments, the tissue reinforcement material can be formed in two or more layers, e.g., as illustrated in FIGS. 30 and 31. For example, the material can have a first layer including a biologic material and a second layer including the plurality of fibers. In various embodiments, the material is a hybrid adjunct material including a biologic material and a synthetic material. It is understood that the biologic material if present, can be in the form of a fiber or in another form, such as a membrane.

Tissue reinforcement materials can be made from essentially any biologic and/or synthetic material having the desired mechanical (e.g., sealing) and biologic (e.g., bioimplantable and bioabsorbable) properties. Representative examples are discussed in the IMPLANTABLE MATERIALS section above. A person skilled in the art will appreciate that the shape of tissue reinforcement materials (and/or layers thereof) are not limited to the parallelepiped or rhombohedron like forms shown in the illustrated examples. In various embodiments, hybrid adjunct materials (and layers thereof) are not necessarily symmetrical as shown in FIGS. 23 and 25 and can, for example, vary in thickness or have irregularly shaped portions.

As discussed above, FIG. 23 illustrates the tissue reinforcement material 1601 in the context of a staple cartridge assembly 1600 for use with a surgical stapler, which is another embodiment encompassed by the present disclosure. The assembly 1600 includes a tissue reinforcement material 1601 and a cartridge body having a plurality of staple cavities configured to seat staples therein (see, e.g., FIGS. 4 and 10). As discussed above, the tissue reinforcement material 1601 is releasably retained on a portion of a surgical stapler end effector (see, e.g., FIGS. 1 and 10), in this example shown in part by an anvil or upper jaw 1602, for delivery to tissue upon deployment of staples. The tissue reinforcement material 1601 includes a plurality of fibers 1603 having an arrangement (in this example, a loop structure) configured to compress and seal around a fastener component inserted therethrough.

Here, the cartridge body and staples are encased by lower jaw of an end effector of a surgical instrument (see, e.g., FIGS. 1 and 10). The tissue reinforcement material 1601 is releasably retained on the anvil or upper jaw 1602 and configured to be delivered to tissue by deployment of the staples from the cartridge body (discussed below). As will be understood by a person skilled in the art, numerous configurations beyond the example of FIG. 23 are possible. For example, tissue reinforcement material can be releasably retained on a staple cartridge, both a staple cartridge and an upper jaw of an end effector, a lower jaw of an end effector, or on both upper and lower jaws of an end effector (see, e.g., FIGS. 31A-C).

A tissue reinforcement material can be releasably retained on a portion of a surgical stapler by retention members, which can come in a variety of forms and configurations such as one or more sutures, adhesive materials, staples, brackets, snap-on or other coupling or mating elements, and the like. Retention members are discussed in further detail in the RETENTION MEMBERS section above. In various embodiments, the assembly includes at least one retention member configured to couple the material to the cartridge body. The at least one retention member, which can include a suture, can be coupled to an outer edge of the cartridge body and an outer edge of at least one of the biologic tissue membrane and the synthetic substrate layer.

Figure 26:
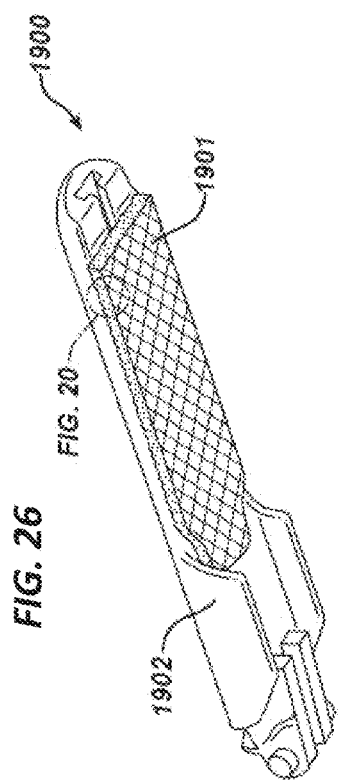
FIG. 26 illustrates a perspective view of an end effector having an alternative exemplary tissue reinforcement material with a collagen matrix that can seal around a fastener component.

In other aspects and embodiments, the disclosure also provides for tissue reinforcement materials that are releasably retained on a portion of a surgical stapler end effector for delivery to tissue upon deployment of staples, where the tissue reinforcement material has an arrangement (other than a loop structure of fibers) configured to compress and seal around a fastener component inserted therethrough. FIG. 26 illustrates a perspective view of one such alternative end effector component 1900, in which the tissue reinforcement material 1901 includes a collagen matrix. Like the embodiment of FIG. 23, the tissue reinforcement material 1901 in FIG. 26 is releasably retained on an upper jaw 1902 of an end effector. However, as will be understood by a person skilled in the art, numerous configurations beyond the example of FIG. 26 are possible. For example, tissue reinforcement material can be releasably retained on a staple cartridge, both a staple cartridge and an upper jaw of an end effector, a lower jaw of an end effector, or on both upper and lower jaws of an end effector (see, e.g., FIGS. 31A-C).

Figure 27:
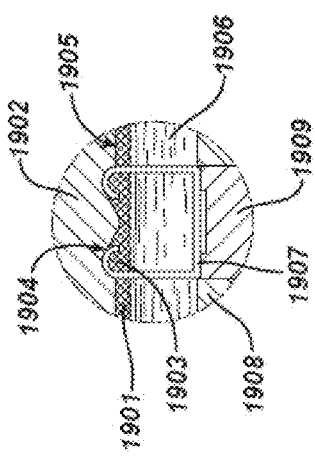
FIGS. 27 and 28 illustrate an exploded cross sectional views of an exemplary fastener inserted through tissue and the tissue reinforcement material of FIG. 26.

As illustrated in FIG. 26, the tissue reinforcement material 1901 includes a collagen matrix formed by molding, and then solidifying, aqueous collagen. For example, a collagen purification and refinement process can suspend collagen in an aqueous state. In this state, fats and other impurities can be skimmed off, and the aqueous collagen can be poured into a mold. As shown in FIG. 26, as well as the detailed cross sectional view of FIG. 27, the mold (not shown) has inverse pockets allowing for the formation of a solid collagen matrix 1901 having a basic anvil pocket shape 1903 on a face 1905 of the matrix, which mates to corresponding pockets 1904 on the upper jaw 1902 of the end effector. The temperature and surface conditions of the mold can be tuned in order to create a density variant around these inverse pocket shapes 1903, and once solidified the inverse pocket shapes 1903 can be keyed into corresponding pockets 1904 on the anvil or upper jaw 1902 of a staple cartridge. Alternatively, a similar method can be used to from a tissue reinforcement material from a thin film of 65/35 PGA/PCL, which in a thin film can act as a semi-adhesive. The amount of PGA/PCL left on the collagen after firing can be minimal.

When tissue reinforcement material 1901, or a similar material, is compressed against tissue 1906 during clamping (i.e., between the upper jaw 1902 and lower jaw 1908 of an end effector) the main collagen body 1901 and the pockets 1903 can be crushed, creating a layer that can easily be penetrated by staples 1907 (e.g., from staple cartridge 1909) but can exclude tissue 1906 from the staple forming area (e.g., pocket 1903), thereby minimizing staple damage to the tissue 1906 (e.g., a blood vessel) and therefore bleeding after stapling.

Figure 28:
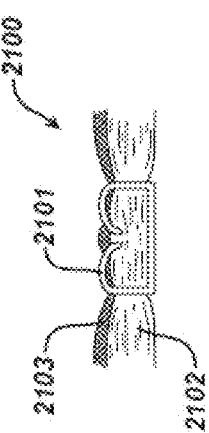

FIG. 28 illustrates a section 2100 of deployed tissue reinforcement material, where materials and methods such as those illustrated in FIGS. 23-27, can be modified by including a substance that swells in the presence of liquids (e.g., hydrogel, oxidized regenerated cellulose (ORC), alginate, and the like). Swelling can aid in sealing around a staple leg 2101 inserted through tissue 2102 and a tissue reinforcement material 2103, and in minimizing tissue damage. A person skilled in the art will appreciate that such swelling materials can include, or be combined with, other features and properties disclosed and discussed herein.

Figure 29:
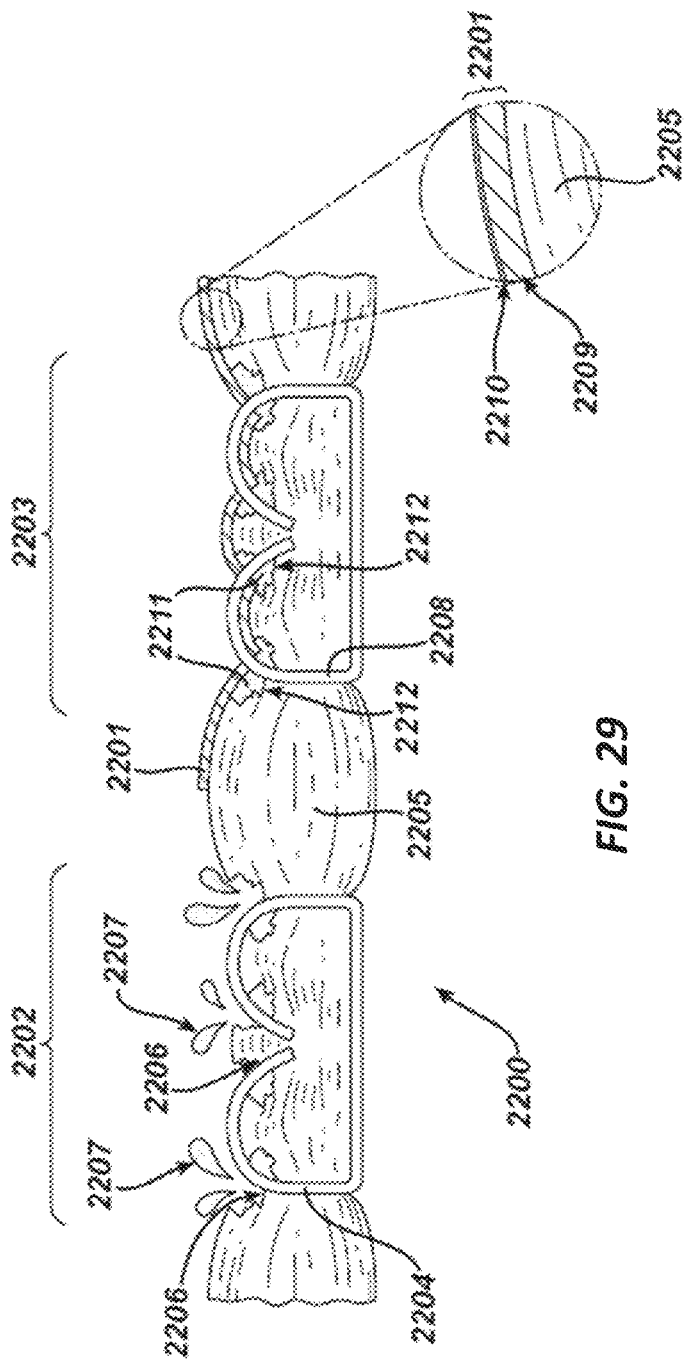
FIG. 29 illustrates a portion of tissue having a stapled section and a section with an exemplary hybrid adjunct tissue reinforcement material after deployment in tissue.

FIG. 29 illustrates an exemplary hybrid adjunct tissue reinforcement material 2201 implanted at a surgical site 2200. Hybrid adjunct materials such as material 2201 can advantageously combine benefits of biologic materials and synthetic materials. For example, biologic adjunct matrices can create less inflammation response (i.e., in comparison to synthetic matrices), while retaining biologic growth factors, chemical compounds, and/or hormones that can facilitate healing. At a micro level however, biologic matrices, whether wet or dry, can be fibrous structures incapable of providing sufficient mechanical sealing (e.g., in demanding applications such as large vessel transection). Hybrid adjunct materials such as material 2201 can, for example, reduce leaking or bleeding (e.g., in a transected and stapled vessel) because hybrid adjunct materials can have the mechanical strength to keep the tissue out of the pocket staple forming area (e.g., as described in connection with FIG. 27) as well as the ability to cinch around the staple legs, to restrict bleeding up the staple legs through the holes made by the staple legs.

In order to illustrate the mechanical properties of the hybrid adjunct material 2201, the surgical site 2200 is shown with a first stapled region 2202 lacking a tissue reinforcement material and a second stapled region 2203 having a hybrid adjunct material 2201. At the first stapled region 2202, a first staple 2204 has been inserted through tissue 2205, thus creating holes 2206 through tissue 2205. As a result, blood loss 2207 can occur through the staple 2204 legs and through the holes 2206 made by the staple 2204 legs.

In contrast, at the second stapled region 2203, a second staple 2208 has been inserted through tissue 2205 as well as the hybrid adjunct material 2201. As illustrated, the hybrid adjunct material 2201 includes a biologic outer tissue contacting layer 2209 that can be thin, resilient, and more elastic than a purely biologic fibrous matrix. The hybrid adjunct material 2201 also includes a synthetic second layer 2210 that is selected not necessarily for strength, spring back, or other gross mechanical reasons, but rather for micro staple interface reasons. In order to maintain the benefit of the biologic layer 2209, the thin synthetic layer 2210 includes a mesh or variable thickness layer that minimizes its interference in contact between the tissue 2205 and the biologic layer 2209. The synthetic layer 2210 forms a seal around the leg of the second staple 2208, and prevents or mitigates blood 2211 from leaking up the second staple 2208 legs through the holes 2212 made by the second staple 2208 legs. In various embodiments the sealing properties of the hybrid adjunct materials can result from a weave of loop structure, a spring or compressive force, swelling, and the like. A person skilled in the art will appreciate that alternative hybrid materials and hybrid adjunct materials can also be used in accordance with the present disclosure. For example, the synthetic layer 2210 could be substituted for a biologic material providing the tissue reinforcement material with the desired mechanical properties.

Figure 30A:
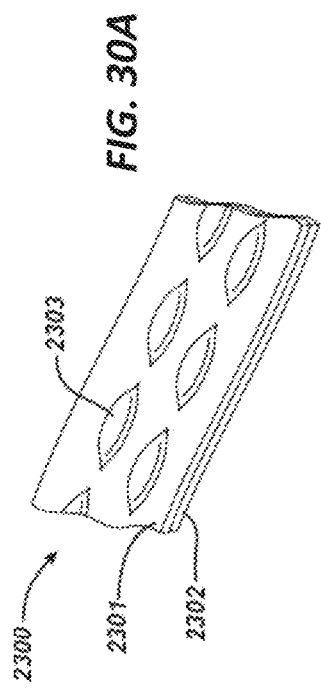
FIG. 30A is an isometric view of an alternative exemplary tissue reinforcement material including a surgical adhesive that seals around a fastener component.
Figure 30B:
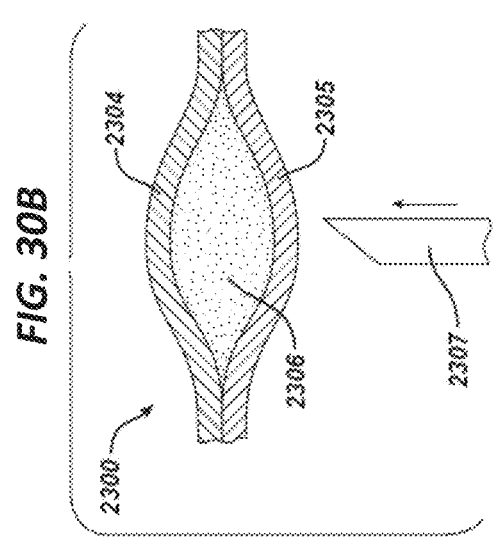
FIG. 30B is a side view of the tissue reinforcement material of FIG. 30A before penetration by a surgical staple.
Figure 30C:
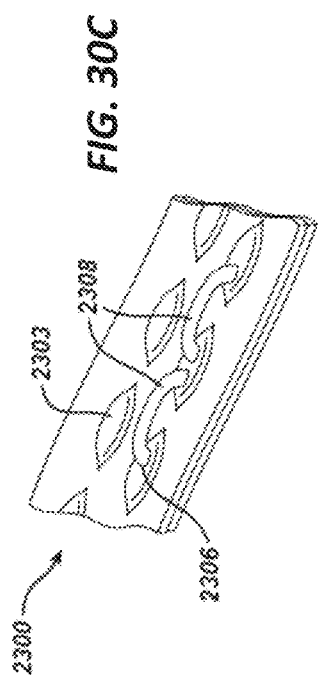
FIG. 30C is an isometric view of the tissue reinforcement material of FIG. 30B after penetration by a surgical staple.

FIGS. 30A-C illustrate different perspective views of an alternative exemplary tissue reinforcement material 2300. Like the tissue reinforcement materials discussed and exemplified above, the tissue reinforcement material 2300 can be releasably retained on a portion of a surgical stapler end effector for delivery to tissue upon deployment of staples and can seal around a fastener component inserted therethrough. Likewise, the tissue reinforcement material 2300 can be part of a staple cartridge assembly.

With reference to FIG. 30A, the tissue reinforcement material 2300 includes a top layer 2301, a bottom layer 2302, and one or more buttresses 2303 having a surgical adhesive therein. The buttresses 2303 can be arranged in a pattern, for example to complement a cartridge body having a plurality of staple cavities configured to seat staples therein. That is, the buttresses 2303 can be aligned with the staple cavities, so that the staples are deployed through and puncture the buttress, and the surgical adhesive seals around the staples and punctures. Although buttresses are used in the embodiment of FIG. 30, other arrangements for providing surgical adhesive can be used. For example, a surgical adhesive can be uniformly sandwiched between top and bottom layers or within layer, or can be disposed within capsules (e.g., similar to FIGS. 31A-C) on the surface of the top or bottom layer. Although the exemplary material illustrated in FIG. 30 uses a surgical adhesive, it is understood that various other materials/fluids/gels having suitable properties can be used in addition or alternatively.

FIG. 30B shows a side view of the tissue reinforcement material 2300 at a buttress 2303, including a top layer of a buttress 2304, a bottom layer of a buttress 2305, and a surgical adhesive 2306 disposed therebetween. FIG. 30B shows a leg of a surgical staple 2307, which is positioned to be deployed and puncture the buttress 2303. The fluid/gel properties of a surgical adhesive can be preserved when sealed between a top layer of a buttress 2304 and a bottom layer of a buttress 2305. Similarly, the top and bottom layers 2304, 2305 can allow the surgical adhesive to flow and achieve desired sealing effect after stapling. FIG. 30C is an isometric view of the tissue reinforcement material 2300 after deployment of staples 2308 that puncture the buttress 2303. As shown, the surgical adhesive 2306 seals around the staples 2308 and punctures in the buttress.

The top layer 2301 and bottom layer 2302 can comprise essentially any of the biologic and synthetic layers, absorbable polymer/polymer blends, gelatins, membranes, and matrices disclosed and described herein, as well adjunct and hybrid adjunct materials. In various embodiments, the surgical adhesive provides acts as a mechanical structure that seals around the fastener component (e.g., staple leg), and prevents leaks (e.g., of blood, air, GI fluids, and the like) at the surgical site. Furthermore, the tissue reinforcement material 2300 can provide reinforcement and/or additional strength to tissue at a surgical site.

Examples of suitable materials for top and/or bottom layers include, but are not limited to, PLLA, PLGA, PCL, PGA, TMC, and associated copolymerizations. Examples of suitable materials/fluids/gels or surgical adhesives include, but are not limited to biologically actives (e.g., freeze dried fibrin/thrombin powder, freeze dried fibrin/thrombin on a short fiber vicryl filament and/or ORC matrix), inertly actives (e.g., ORC fibers in a PCL/PGA liquid), viscous absorbables (e.g., 65/35 PCL/PGA, 50/50 PCL/PGA, 50/50 PLLA/PCL, and the like), viscous urethane gels, and gelatinous absorbables (e.g., blends of copolymers or isomers). Examples of suitable film materials include, but are not limited to PLLA, PLGA, PCL, PGA, TMC, associated copolymerizations, and the like.

FIGS. 31A-C illustrate another alternative exemplary a tissue reinforcement material including a surgical adhesive that seals around a fastener component.

With reference to FIG. 31A, a first tissue reinforcement material 2401 is releasably retained on an anvil 2402 portion of a surgical stapler end effector 2400 for delivery to tissue upon deployment of staples, to seal around a fastener component inserted therethrough. The first tissue reinforcement material 2401 includes a first top layer 2403, a first bottom layer 2404, and a first surgical adhesive 2405 disposed therebetween. The anvil 2402 defines a plurality of pockets 2406, which correspond to a first plurality of mating pocket shaped features 2407 defined by the first tissue reinforcement material 2401 and encapsulating the first surgical adhesive 2405. In various embodiments, the plurality of pockets 2406 and corresponding plurality of mating pocket shaped features 2407 mediate, at least in part, the releasable retention of the material 2401 on the anvil 2402.

A second tissue reinforcement material 2411 is releasably retained on a staple cartridge 2412 portion of a surgical stapler end effector 2400 for delivery to tissue upon deployment of staples, to seal around a fastener component inserted therethrough. The second tissue reinforcement material 2411 includes a second top layer 2413, a second bottom layer 2414, and a second surgical adhesive 2415 disposed therebetween. The staple cartridge 2412 defines a plurality of pockets 2416, which correspond to a plurality of mating pocket shaped features 2417 defined by the second tissue reinforcement material 2411 and encapsulating the second surgical adhesive 2415. In various embodiments, the plurality of pockets 2416 and corresponding second plurality of mating pocket shaped features 2417 mediate, at least in part, the releasable retention of the material 2411 on the staple cartridge 2412. The staple cartridge 2412 has a plurality of staple cavities 2418 configured to seat staples 2419 therein.

FIG. 31B illustrates an exploded view of a portion of the anvil 2402 assembly and staple cartridge 2412, which provides additional detail on the various features of the portion of a surgical stapler end effector 2400, especially the pockets 2406, 2416, corresponding plurality of mating pocket shaped features 2407, 2417, and their relative positioning to the staples 2419.

FIG. 31C illustrates an isometric view of the first tissue reinforcement material 2401 and second tissue reinforcement material 2411 described above in connection with FIGS. 31A and 31B. This view focuses on the features of the first and second top layers 2401, 2413, namely the first and second plurality of mating pocket shaped features 2407, 2417. In FIG. 31C the second tissue reinforcement material 2411 is shown as being partially cutaway to illustrate the relative positioning of the second plurality of mating pocket shaped features 2417.

A person skilled in the art will appreciate that various additional embodiments in accordance with the disclosure can be provided by varying the number, location, composition, size, shape, etc. of the various components illustrated in FIGS. 31A-C. A number of representative compositions and configurations, which can be used with the embodiment in FIGS. 31A-C, are discussed in the detailed description and exemplary embodiments above.

FIGS. 31A-C show two film layers 2403, 2404 and 2413, 2414 with a captured material 2405, 2415 (e.g., surgical adhesive) that can be viscous and/or reactive with body fluids, to seal around staples 2419 like a needle in a rubber gasket. A viscous fluid can fill an imperfection and/or tear in a film layer 2403, 2404, 2413, 2414 created by a staple 2419 leg. Material 2405, 2415 can be a biologic such as fibrin, thrombin, calcium alginate, or cellulose (e.g., ORC, or oxidized regenerated cellulose, which is a fiber in its solid non-reacted form). Material 2405, 2415 can also be a absorbable synthetic like 50/50 PCL/PGA or 70/30 PCL/PGA, which remains a viscous fluid or semi-solid at body temperature.

In another aspect, the disclosure provides a method for implanting a tissue reinforcement material.

Figure 32A:
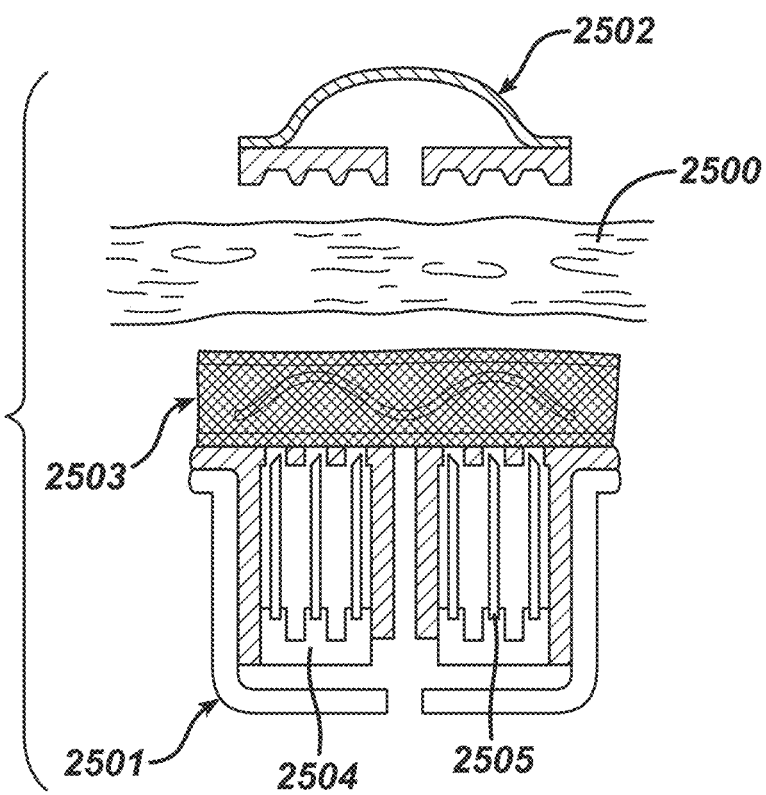
FIGS. 32A-C illustrate an exemplary method for implanting a tissue reinforcement material.
Figure 32B:
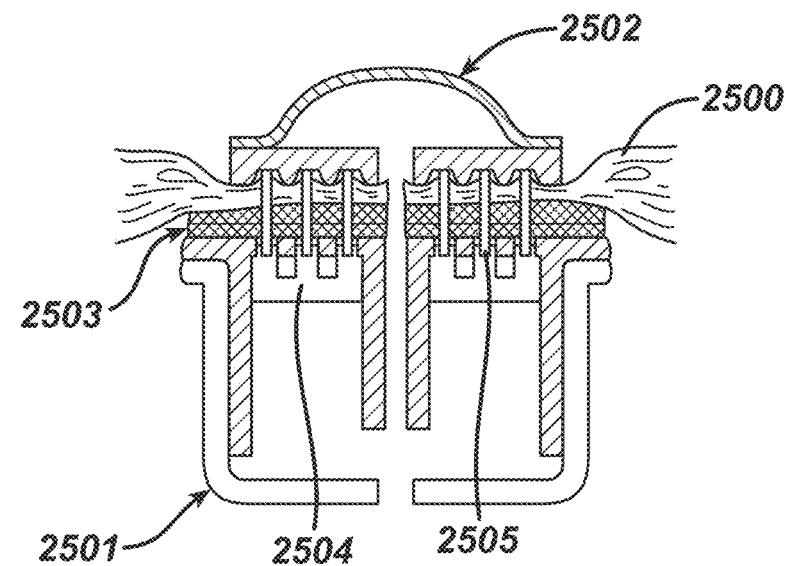
Figure 32C:
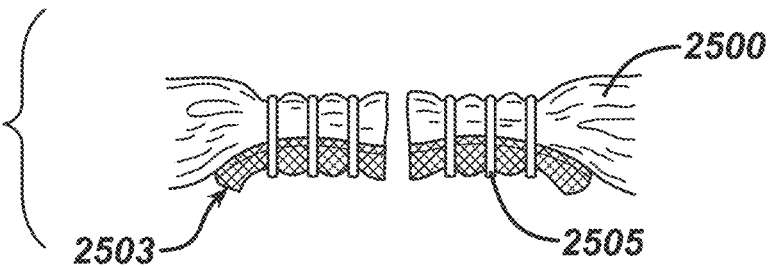

In another aspect, the disclosure provides methods for implanting a tissue reinforcement material. FIGS. 32A-C illustrate an example of one such method. However, it is understood that this and other methods provided by the present invention are applicable to the use of essentially any sealing tissue reinforcement materials in accordance with the present invention.

FIG. 32A illustrates the engagement of tissue 2500 between a lower jaw 2501 and an anvil or upper jaw 2502 of a surgical stapler at a surgical site. At least one of the lower jaw 2501 and upper jaw 2502 has a tissue reinforcement material 2503 releasably retained thereon. In this example, the lower jaw 2501 (e.g., through the cartridge assembly 2504) has a tissue reinforcement material 2503 releasably retained thereon. The material 2503 includes a plurality of fibers having an arrangement adapted to compress and seal around a fastener component inserted therethrough (see, e.g., FIGS. 23-25 and alternative embodiments in FIGS. 26-31). Here, the tissue 2503 is engaged between an anvil or upper jaw 2502 and the lower jaw 2501, which encases the cartridge assembly 2504 having staples 2505 disposed therein.

FIG. 32B illustrates an actuated surgical stapler that has ejected staples 2505 from the cartridge body 2504, and into the biological tissue 2500. The staples 2505 extend through the tissue reinforcement material 2503 to maintain the material 2503 at the surgical site. In this example, actuation of the surgical stapler also cuts the tissue 2503 at a surgical site between the staples 2505, as shown in FIG. 32B. Further embodiments and examples of such cutting embodiments are described above. However, the present disclosure also contemplates embodiments where tissue is not necessarily cut, or where tissue is not necessarily cut concurrently with actuation of the surgical stapler.

FIG. 32C illustrates the tissue 2500 following deployment of staples 2505 and tissue reinforcement material 2503. As shown, the staples 2505 extend through the tissue reinforcement material 2503 and the tissue 2500 to maintain the material 2503 at the surgical site. In this illustration, the tissue 2500 comprising the staples 2505 is sealed and reinforced by the material 2503, thereby preventing or mitigating tearing, fluid (e.g., blood), or other undesired damage to the surgical site. In various embodiments, it is only required that the material form a seal around the fastener component (e.g. staple leg). Avoiding undesired damage can decease surgical recovery time and mitigate surgical complications. Furthermore, the reinforcement can promote healing through the action of a biologic matrix in the material 2503 and/or biologically active compounds therein. Similarly, the reinforcement can prevent or mitigate irritation and inflammation from synthetic material because any such synthetic can be internal to a biologic tissue membrane or matrix and/or because the synthetic essentially does not contact the tissue 2500. In alternative embodiments, essentially all synthetic material can be encapsulated by biologic material, to prevent or mitigate irritation and inflammation from synthetic material.

Positively Charged Synthetic Matrix

The retention members provided for herein, or other retention members known to those skilled in the art, can be used in conjunction with a variety of adjunct materials, such as adjunct materials 200, 200', 200", 200'" shown in FIGS. 12-15. While in some instances adjunct materials 200, 200', 200", 200'" can be a synthetic material, a biologic material, or a combination thereof, in some exemplary embodiments the adjunct materials can include synthetic material(s) having an electrical (e.g., positive) charge.

Any adjunct material, or combination of adjunct materials, discussed herein can be configured to have such an electrical (e.g., positively) charge. In some embodiments, the adjunct material can be formed of a synthetic material that has positively charged polymers or copolymers and/or the adjunct material can be treated such that the polymer or copolymers forming the adjunct material are substantially permanently positively charged. A skilled in the art will understand that adjunct materials having at least a portion of material that is positively charged can be formed of and/or used in combination with any other type of adjunct material or matrix material—including but not limited to biologic materials, synthetic materials, hydrophilic materials, hydrophobic materials, bioabsorbable materials, biofragmentable materials, or combinations thereof.

The charged particles can be dispersed throughout the adjunct material in any known manner. As used herein, "disperse" and conjugates thereof is used in its broadest sense to include distributed or spread over an area, which can be uniform or not, as desired. By way of example, layers having a uniform charge, or portions thereof having a charge, are considered to be dispersed, as well as discrete particles embedded in a material are dispersed. In some embodiments, for example, the charged particles can be dispersed throughout the entirety of the adjunct material such as by treating the entirety of the adjunct material to have a permanent positive charge—as is discussed below—or can be just on an outer surface of the adjunct material. Alternatively, portions of the adjunct material can be positively charged and distributed within or on the adjunct material. For example, an adjunct material that is otherwise uncharged can have a plurality of charged spheres or beads embedded or otherwise incorporated therein. Alternatively, a layer of positively charged synthetic material can be laminated onto or adjacent an uncharged layer of adjunct material. Additional embodiments can include a bioscaffold with a positive charge on the surface of fibers that form the bioscaffold, and, alternatively, an extracellular matrix buttress material having positively charged microspheres implanted therein. As mentioned herein, adjunct material can include biologic materials, synthetic materials, hydrophilic materials, hydrophobic materials, or any other known material or combination of materials. In one embodiment, for example, a biologic layer is formed with positively-charged synthetic spheres embedded or implanted throughout the biologic layer. It is also appreciated that any support structures or other component of an adjunct material layer can have an electrical charge.

Figure 33A:
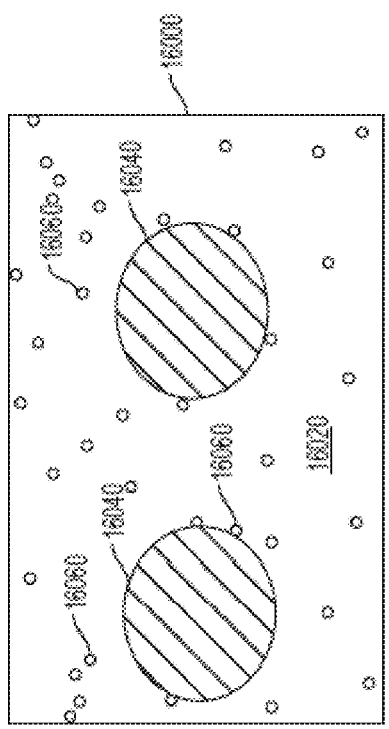
FIG. 33A is a perspective view of a cell dispersion having uncharged polymer spheres.
Figure 33B:
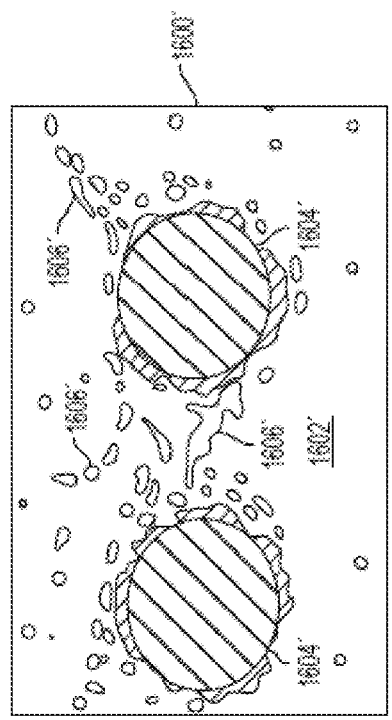
FIG. 33B is a perspective view of a cell dispersion having positively charged polymer spheres.

The electrical (e.g., positively) charge can attract additional cells and enhance healing in vivo. For example positively charged adjunct materials can help cells grow onto the material (i.e., increase cell mobility) and can attract additional cells to the wound site itself. To illustrate this, FIG. 33A depicts a standard cell dispersion 16000 of a healing area 16020 that contains uncharged polymer spheres 16040, for example as part of a polymer scaffold, and a plurality of cells 16060. It can be seen that some of the cells 16060 adhere to the uncharged polymer spheres 16040, however there is no appreciable accumulation of cells 16060 near the uncharged polymer spheres 16040. By contrast, FIG. 33B illustrates a cell dispersion 1600' of healing area 1602' having positively charged polymer spheres 1604' and cells 1606'. As can be seen cells 1606' are attracted into the area of the positively charged polymer sphere 1604' due to the positive charge of the polymer spheres 1604'. Because the spheres 1604' attract additional cells 1606' to the healing area 1602', the healing area 1602' (i.e., a wound site) can experience enhanced healing and cellular ingrowth.

Figure 34:
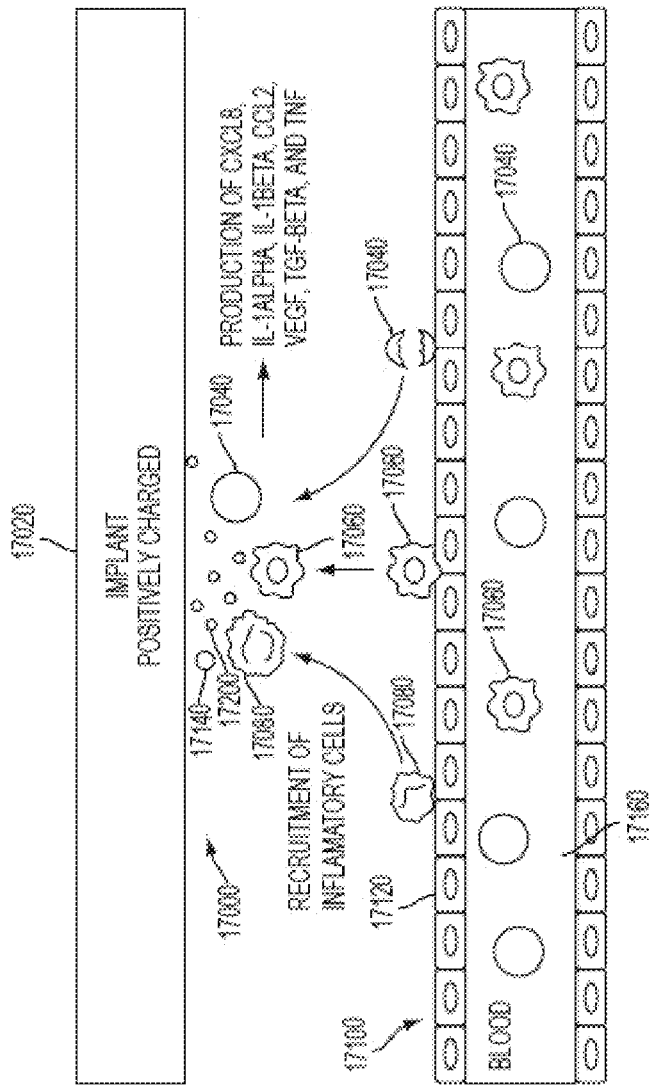
FIG. 34 is a schematic view of an embodiment of a mechanism of electrically charged implant material enhancing healing at a wound site.

By way of example only, FIG. 34 shows a mechanism by which an adjunct material ("implant") 17020 having positively charged particles can enhance healing at a wound site area 17000. As shown, various cells, including T-cells 17040, macrophages 17060, and neutrophils 17080, are present in the wound site area 17000 as these cells are typically found flowing through the circulatory system, such as in a blood vessel 17100. Blood vessels are typically lined with endothelial cells 17120 that allow blood components such as erythrocytes (not shown), fibroblasts (not shown), platelets 17140, platelet-derived growth factor ("PDGF") 17200, T-cells 17040, macrophages 17060, and neutrophils 17080 to pass from an interior 17160 of the blood vessel 17100 through the endothelial cell lining 17120 and into the wound area 17000. A person skilled in the art will understand that blood and blood components are negatively charged. Thus, because the implant 17020 has positively charged particles, inflammatory cells and blood components responsible for healing the wound site (which, as mentioned, can be negatively charged), including platelets 17140, PDGF 17200, T-cells 17040, macrophages 17060, and neutrophils 17080 are attracted to the implant surface 17020 and thus the wound site 17000 thereby enhancing healing relative to a system that does not have increased cell attraction. Additionally, the positively charged implant 17020 can activate tissue macrophages 17060. When activated, macrophages 17060 release growth factors and active cytokines into the wound, providing a stimulus for cell proliferation and collagen matrix deposition, thus further enhancing healing.

Materials that work using the positive charge mechanism described above can include a polysaccharide backbone (matrix) with attached functional groups, for example cellulose or dextrose gels. Additionally, a person skilled in the art will appreciate that the key to enabling desirable wound healing lies in the functional groups, which can include diethylaminoethyl and quarternay amine groups.

At least portions of adjunct material, or any other extra cellular matrix (ECM) materials, can have a charge induced or otherwise produced thereon. To produce an electrical (e.g., positive) charge on absorbable polymers, any suitable method and material can be used. In some embodiments, a permanent positive charge can be induced or otherwise formed on at least a portion of an adjunct material, preferably at least on an outer surface of the material. In some embodiments, for example, a positively charged initiator molecule can be used to induce a ring opening polymerization of cyclic monomers. Any known cyclic monomer can be used during synthesis of absorbable polymers and copolymers, such as glycolide, lactide, caprolactone, p-dioxanone, and combinations thereof.

The initiator molecules can be any positively charged molecule that initiates the ring opening polymerization of the cyclic monomer(s). Examples of initiator molecules that can be used to create permanent positive charge on absorbable polymers include 2,3-dihydroxyporpyldimethylalkylammonium chloride such as is represented by formula (I), choline such as is represented by formula (II), and choline functionalized dimethylolpropionic acid such as is represented by formula (III):

I where R is H or an alkyl chain, (II)

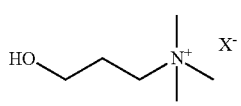

where X is Cl, Br, or I, and

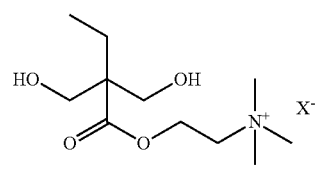

(III)

where X is Cl, Br, or I.

Use of these initiators during synthesis of various absorbable polymers and copolymers can result in absorbable polymers/copolymers with a positive charge either at the end of the polymer chains or as a pendant group attached to the polymer backbone. A positive charge produced using these initiators can be substantially permanent. Using these initiators and/or process, a positive charge can be created on any of the synthetic polymers or copolymers described herein, such as such as a polydioxanone film sold under the trademark PDS® or with a Polyglycerol sebacate (PGS) film or other biodegradable films formed from PGA (Polyglycolic acid, marketed under the trade mark Vicryl), PCL (Polycaprolactone), PLA or PLLA (Polylactic acid), PHA (polyhydroxyalkanoate), PGCL (poliglecaprone 25, sold under the trademark Monocryl), PANACRYL (Ethicon, Inc., Somerville, N.J.), Polyglactin910, Poly glyconate, PGA/TMC (polyglycolide-trimethylene carbonate sold under the trademark Biosyn), polyhydroxybutyrate (PHB), poly(vinylpyrrolidone) (PVP), poly(vinyl alcohol) (PVA), or a blend of copolymerization of the PGA, PCL, PLA, PDS monomers. For example, exemplary copolymers include copolymers of PGA/PCL and/or PLLA/PCL, such as various polymers having PGA/PCL ratios in the range of about 25:75 to 90:10, and/or PLLC/PCL in the range of about 70:30. Additionally, in some embodiments preparation of foams via lyophilization of solutions of these polymers and/or copolymers can result in a porous matrix having a positive charge throughout the matrix.

Hybrid Adjunct Material

The retention members provided for herein, or otherwise known to those skilled in the art, can be used in conjunction with a variety of adjunct materials. While in some instances the adjunct materials can be either a synthetic material or a biologic material, in some exemplary embodiments the adjunct material can include both synthetic material(s) and biologic material(s), referred to herein as a hybrid adjunct material. The resulting combination can advantageously have both permeable and non-permeable elements, and allows for the beneficial features of both types of adjunct materials to be incorporated into a single adjunct material. For example, synthetic material can provide structure and support for biologic material, and can add strength and shear resistance to fibrous biologic material, while still being configured to allow the biologic material to have direct access to a surgical site so the biologic material can provide improved healing and tissue growth at the stapled location. Depending on the type of material that is used, either or both synthetic and biologic material can help seal holes formed by staples as they are implanted into tissue, blood vessels, and various other objects or body parts. Further, either or both of the synthetic and biologic materials can be configured to help reduce inflammation, promote cell growth, and otherwise improve healing.

A hybrid adjunct material can be selectively attached to either or both jaws of an end effector. As shown in FIGS. 35A and 35B, a hybrid adjunct material 3400, 3400' is attached to both lower and upper jaws 31052, 31054 of an end effector 31050. The hybrid adjunct material 3400, 3400' of the illustrated embodiment includes a synthetic material, layer, or matrix 3402, 3402' in the form of a polymer mesh, and a biologic material, layer, or matrix 3404, 3404' in the form of a bioabsorbable membrane. The terms material, layer, and matrix are often used interchangeably herein, and to the extent any of these terms are used, the terms are not so limiting as to require a particular shape, thickness, or configuration. A person skilled in the art will recognize a variety of configurations that the synthetic and biologic materials can have that allow them to be used in conjunction with an end effector without departing from the spirit of the present disclosure. As described herein, the synthetic and biologic layers 3402, 3402' and 3404, 3404' can be coupled to the lower and upper jaws 31052, 31054 using a variety of techniques, but in the illustrated embodiment a pair of brackets 3406 is used to maintain a location of the hybrid adjunct material 3400 with respect to the cartridge assembly or lower jaw 31052. Likewise, a pair of brackets 3406' is used to maintain a location of the hybrid adjunct material 3400' with respect to the upper jaw 31054.

The lower jaw 31052 and associated hybrid adjunct material 3400 are illustrated in FIG. 35A. Similar to some of the embodiments described herein, the lower jaw 31052 can have a staple cartridge 31100 disposed therein. The staple cartridge 31100 can include staples for deployment at the surgical site, and as shown, can include support struts 31103. The support struts 31103 can help stabilize the cartridge 31100 within a support channel 31056 of the lower jaw 31052, and can also be engaged by the brackets 3406 to help temporarily secure the hybrid adjunct material 3400 to the lower jaw 31052.

The biologic layer 3404 can have many different configurations in terms of its size, shape, and the materials of which it is comprised, but in the illustrated embodiment the biologic layer 3404 is substantially planar and rectangular, and includes a bioabsorbable membrane. The biologic layer 3404 can be in the form of an extracellular matrix, and/or it can include patient-derived materials such as platelet enriched plasma, diced tissue fragments, fibrin, and stem cells. Other types of biologic materials that can be incorporated into the biologic layer 3404 are provided earlier in this disclosure. As shown in FIGS. 35A and 35B, a bottom surface 3404b of the biologic layer 3404 is facially opposed to a top surface 31100a of the staple cartridge 31100 and the two surfaces 3404b, 31100a are in contact with each other.

The synthetic layer 3402 can likewise have many different configurations in terms of its size, shape, and the materials of which it is comprised. In the illustrated embodiment the synthetic layer 3402 is substantially planer and rectangular and includes a plurality of openings 3408 formed therein to provide a lattice structure or mesh. This open configuration allows components of the biologic layer 3404 to pass through the synthetic layer 3402 and provide desired healing to tissue at the surgical site, while still providing a support structure for the biologic layer 3404. If the synthetic layer 3402 was not permeable and contained no openings, it could act as a barrier between the tissue and the biologic layer 3404. Thus, in instances in which there are no openings, typically the synthetic layer 3402 is permeable. Any number of materials can be used to form the synthetic layer 3402, including those described above, but in some embodiments a polymer is used. Further, healing agents and/or biologic materials can be incorporated into the synthetic layer 3402, for instance by painting a layer of the agents and/or biologic materials on a top surface 3402a of the synthetic layer 3402.

As shown in FIGS. 35A and 35B, a bottom surface 3402b of the synthetic layer 3402 is facially opposed to a top surface 3404a of the biologic layer 3404 and the two surfaces 3402b, 3404a are in contact with each other.

The one or more brackets 3406 can be used to maintain the location of the biologic and synthetic layers 3404, 3402 with respect to the staple cartridge 31100 and lower jaw 31052. In the illustrated embodiment, two opposed brackets 3406 are configured to engage a bottom surface 31103b of the strut 31103 and the top surface 3402a of the synthetic layer 3402 to maintain the location of the layers 3404, 3402. The brackets 3406 can have any number of shapes, sizes, and configurations, but in the illustrated embodiment of FIGS. 35A and 35B, a channel 3410 for engaging the top surface 3402a of the synthetic layer 3402 extends the length of a top portion 3406a of the bracket 3406, and a plurality of engagement tabs 3412 for engaging the bottom surface 31103b of the struts 31103 extend from the channel 3410. As also shown in FIG. 35B, the hybrid adjunct material 3400' that includes the biologic layer 3404' and the synthetic layer 3402' can also be associated with an anvil or upper jaw 31054 of the end effector 31050, for instance by using opposed brackets 3406'. As shown, top channels 3410' of the brackets 3406' engage a surface of a cover plate 31062 of the upper jaw 31054, and the bottom tabs 3412' engage a bottom surface 3402b' of the synthetic layer 3402'. The synthetic and biologic layers 3402', 3404' associated with the upper jaw 31054 can have the same size, shape, and composition as the synthetic and biologic layers 3402, 3404 associated with the lower jaw 31052, or the sizes, shapes, and compositions can be different. Additional details about associating a hybrid adjunct material with an anvil are provided further below.

FIG. 36 provides another configuration of hybrid adjunct materials 3500, 3500' associated with each of the lower and upper jaws 31052, 31054. As shown, a biologic layer 3504 associated with the lower jaw 31052 is disposed between two synthetic layers 3502, 3503, and a biologic layer 3504' associated with the upper jaw 31054 is disposed between two synthetic layers 3502', 3503'. The synthetic layers 3502, 3502' can be permeable so as to allow biologic materials from the respective biologic layers 3504, 3504' to pass through the synthetic layer 3502, 3502' and interact with surrounding tissue upon deployment. The synthetic layer 3503, 3503' can also be permeable. Optionally, either or both of the synthetic layers 3502, 3502' and 3503, 3503' can have one or more openings formed therein to allow biologic material to pass therethrough. In one exemplary embodiment, the synthetic layers 3502, 3502' and 3503, 3503' are an absorbable alginate membrane and the biologic layers 3504, 3504' include platelet rich plasma (PRP). The synthetic and biologic materials associated with the lower and upper jaws 31052, 31054 can be, but do not have to be, the same shape, size, and/or composition.

Opposed brackets 3506 can be used to maintain the location of the synthetic and biologic layers 3502, 3503, 3504 with respect to the lower jaw 31052, and opposed brackets 3506' can be used to maintain the location of the synthetic and biologic layers 3502', 3503', 3504' with respect to the upper jaw 31054. While any configuration of bracket can be used, in the illustrated embodiment the brackets 3506, 3506' include top and bottom channels 3510, 3512 and 3510', 3512' that extend a length of the brackets 3506, 3506' and an end wall 3514, 3514' that connects the two channels 3510, 3512 and 3510', 3512'. As shown, the bottom channel 3512 engages the bottom surface 31103b of the struts 31103 and the top channel 3510 engages a top surface 3502a of the synthetic layer 3502, while the bottom channel 3512' engages a bottom surface 3502b of the synthetic layer 3502 and the top channel 3510' engages a surface of the cover plate 31062 of the upper jaw 31054.

Optionally, one or more ports 3520, 3520' can be formed in the hybrid adjunct material 3500, 3500' and/or the brackets 3506, 3506' to allow materials, such as patient-derived materials, including fluids, to be injected into the hybrid adjunct material 3500, 3500'. The ports 3520, 3520' can be non-permeable and self-sealing. In the illustrated embodiment, the ports 3520, 3520' extend through the brackets 3506, 3506' and into the biologic layers 3504, 3504', however in other embodiments, such as those in FIGS. 35A and 35B in which the brackets 3406, 3406' do not cover a length-wise edge of the hybrid adjunct material 3400, 3400', the ports can be formed in one or both of the synthetic and biologic layers 3502, 3502' and 3504, 3504' without being formed in the brackets.

Figure 37:
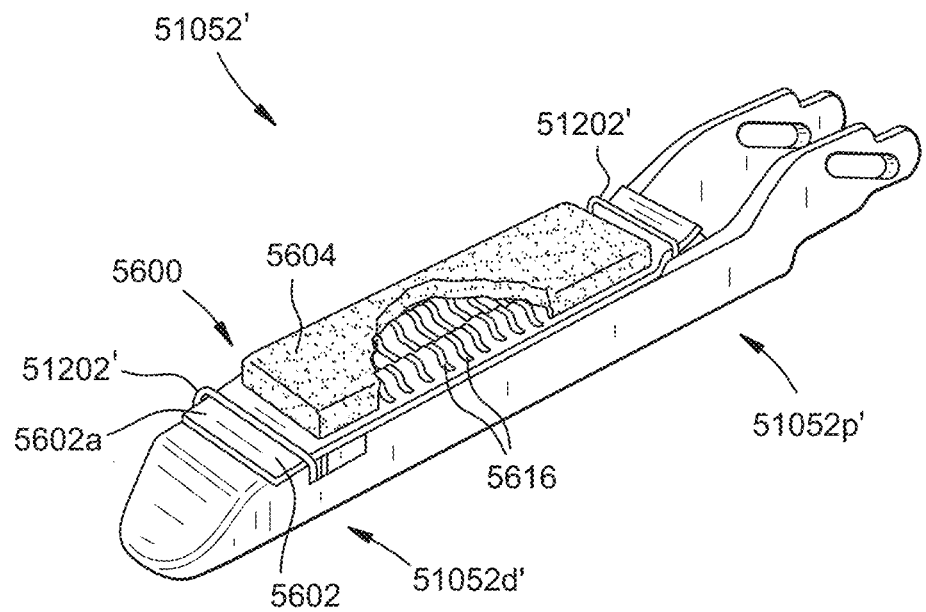
FIG. 37 is a perspective view of yet another exemplary embodiment of a hybrid adjunct material coupled to a lower jaw of an end effector, with a portion of a biologic layer of the hybrid adjunct material removed for illustrative purposes.

In other embodiments of a hybrid adjunct material, a synthetic layer can be coupled to a jaw of the end effector and can include one or more mating features for receiving and coupling to a biologic layer. For example, FIG. 37 illustrates a lower jaw 51052' having a hybrid adjunct material 5600 associated therewith. A synthetic material, layer, or matrix 5602 of the hybrid adjunct material 5600 can be coupled to the jaw 51052' using retention members 51202' extending across proximal and distal ends 51052p', 51052d' thereof. Further, the synthetic matrix 5602 can include one or more protrusions, as shown springs 5616, which are adapted to engage a biologic material, layer, or matrix 5604 to mate the biologic matrix 5604 to the synthetic matrix 5602, thereby substantially maintaining a location of the biologic matrix 5604 with respect to the synthetic matrix 5602 and the lower jaw 51052'. In the illustrated embodiment, the springs 5616 form a skeletal structure around which the biologic matrix 5604 can be formed. For example, when the biologic matrix 5604 is formed from collagen, which as discussed elsewhere in this disclosure can be melted into its aqueous state and then reformed into a hardened state, the synthetic matrix can be dipped in the collagen when the collagen is in its aqueous state. As the collagen reforms or hardens, it can form around the skeletal structure defined by the configuration of the springs 5616, thereby integrating the biologic matrix with the synthetic matrix during refinement. The resulting hybrid adjunct material can be a macro-composite adjunct that benefits from the strength and tear resistance of the internal synthetic frame and the simple parameter attachment features provided by the springs 5616, e.g., the shape and material of the springs, while still providing for the benefits of having biologic material at the implantation site. A person skilled in the art will recognize a variety of other protrusions that can extend from a top surface 5602a of the synthetic matrix 5602 in any number of configurations to provide an internal skeletal structure for forming a hybrid adjunct material.

Figure 38:
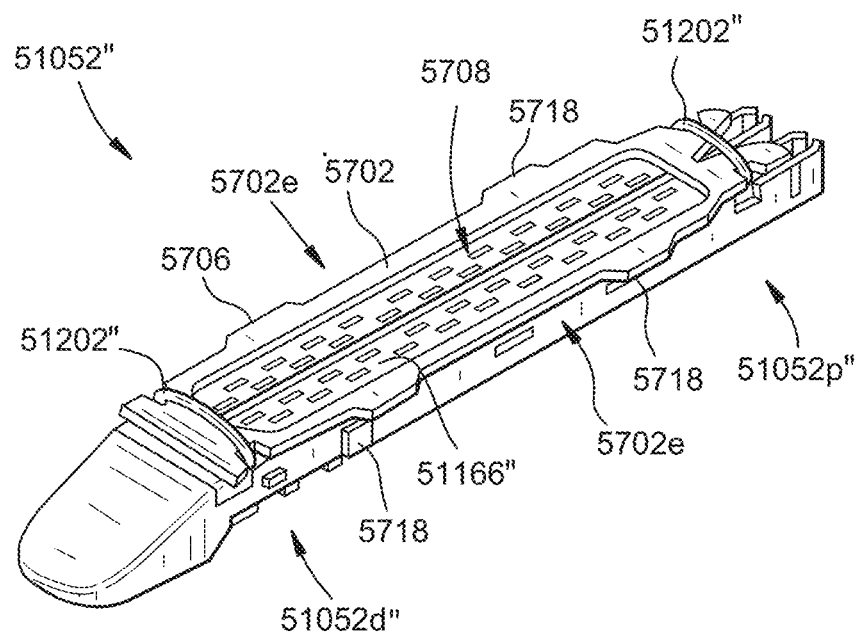
FIG. 38 is a perspective view of one exemplary embodiment of a synthetic layer of a hybrid adjunct material coupled to a lower jaw of an end effector.

Synthetic materials or layers can have a variety of other configurations that are conducive to both providing a support structure for the biologic materials or layers while permitting the biologic materials to pass therethrough so that they can interact with tissue engaged by the staple. Various configurations are illustrated herein. As shown in FIG. 38, a synthetic material, layer, or matrix 5702 is coupled to a lower jaw 51052" by retention members 51202", which as shown are sutures, disposed at proximal and distal ends 51052p", 51052d" thereof. The synthetic layer 5702 can include a large, central opening 5708 formed therein to permit biologic materials disposed above the synthetic layer 5702 to interact with the staples disposed in a staple cartridge 51100" below, as well as the tissue in which the staples are injected. Accordingly, the synthetic layer 5702 can serve as a frame for the hybrid adjunct material 5700, configured to only be disposed around a perimeter of a biologic layer disposed on top of the synthetic layer 5702. Shoulders 5718 formed on outer edges 5702e of the synthetic layer 5702 can provide structure that at least one of a biologic layer and a coupling mechanism like a bracket can engage to attach the biologic layer to the synthetic layer 5702, and thus the lower jaw 51052".

Figure 39:
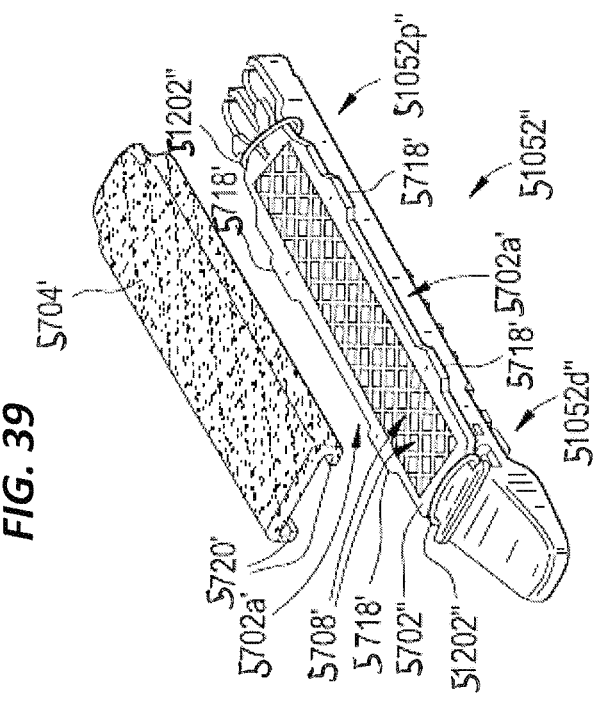
FIG. 39 is a perspective view of another exemplary embodiment of a synthetic layer of a hybrid adjunct material coupled to a lower jaw of an end effector, and further including a biologic layer configured to couple to the synthetic layer.

The lower jaw 51052" of FIG. 39 also provides for a synthetic material, layer, or matrix 5702' that permits biologic materials to pass therethrough. As shown, the synthetic layer 5702' is coupled to the lower jaw 51052" by retention members 51202", e.g., sutures, disposed at proximal and distal ends 51052p", 51052d" thereof. A plurality of openings 5708' can be formed therein such that the synthetic layer 5702' has a matrix or lattice structure, with the bars forming the lattice extending diagonally to a length of the layer 5702' and substantially perpendicular with respect to each other. Similar to openings in other synthetic materials, the openings 5708' can permit biologic materials to pass therethrough. The synthetic layer 5702' can include shoulders or tabs 5718' formed on its edges 5702e'. As a result, a biologic material such as the material, layer, or matrix 5704' illustrated in FIG. 39 can have channels 5720' formed therein that are configured to engage the shoulders 5718', as described in further detail below with respect to a related embodiment illustrated in FIGS. 40A-E.

Figure 40A:
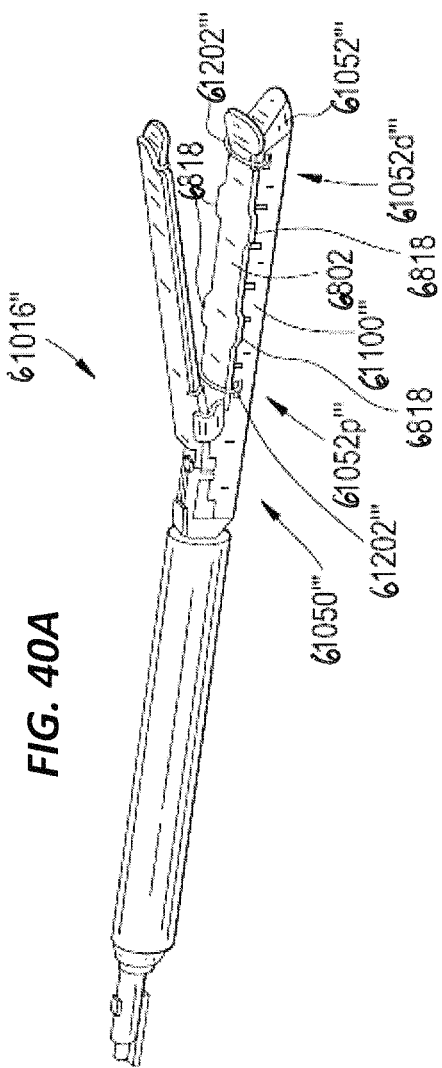
FIG. 40A is a perspective view of one exemplary embodiment of an attachment portion of a surgical instrument having a synthetic layer coupled to a lower jaw thereof.
Figure 40B:
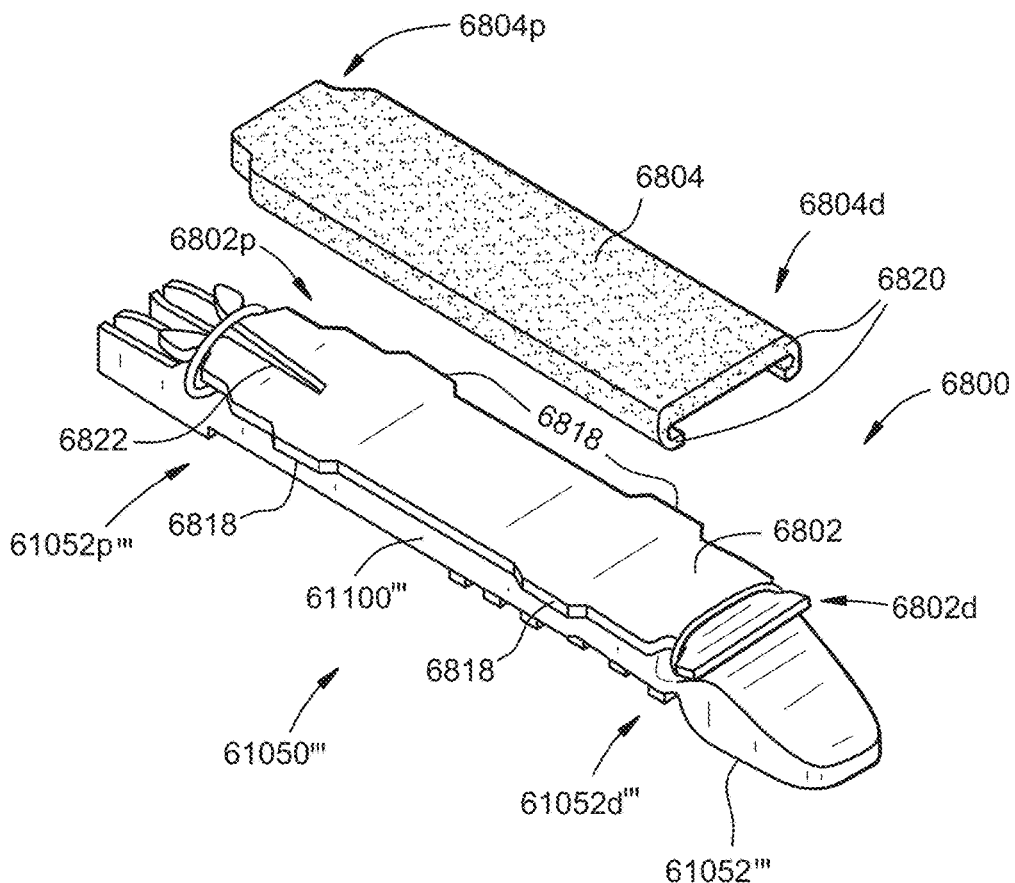
FIG. 40B is a perspective view of the lower jaw of FIG. 40A and a biologic layer configured to couple to the synthetic layer.

The biologic layer can be coupled to the synthetic layer using a number of techniques, such as the brackets discussed above. In another exemplary embodiment one of the synthetic and biologic layers can be configured to form a snap-fit with the other layer. As shown in FIG. 40A, a synthetic material layer 6802 is disposed over a staple cartridge 61100''' and coupled to a lower jaw 61052''' of an end effector 61050''' of an attachment portion 61016''' by retention members 61202''' disposed at proximal and distal ends 61052p''', 61052d''' thereof. The synthetic layer 6802 can be generally permeable, and can include shoulders 6818 for receiving a biologic material, layer, or matrix 6804 (FIG. 40B) to form a hybrid adjunct material 6800. Further, as shown in FIG. 40B, the synthetic layer 6802 can include a groove 6822 formed at a proximal end 6802p thereof for receiving a knife that passes through the end effector 61050'''. The groove 6822 enables the knife to cut the synthetic layer 6802 to release the synthetic and biologic layers 6802, 6804 from the end effector 61050''' and allows the layers 6802, 6804 to be secured at the treatment location by staples of the staple cartridge 61100'''.

The biologic layer 6804 can include opposed channels 6820 configured to form a snap-fit with the synthetic layer 6802. As shown in FIG. 40B, the channels 6820 extend along a substantial length of the biologic layer 6804. A proximal end 6804p of the biologic layer 6804 can include a portion that is sized to be complementary with a proximal end 6802p of the synthetic layer 6802. Accordingly, as shown, the proximal end 6804p of the biologic layer 6804 can have a smaller width than a distal end 6804d thereof, just as the proximal end 6802p of the synthetic layer 6802 also has a smaller width than a distal end 6802d thereof.

Figure 40C:
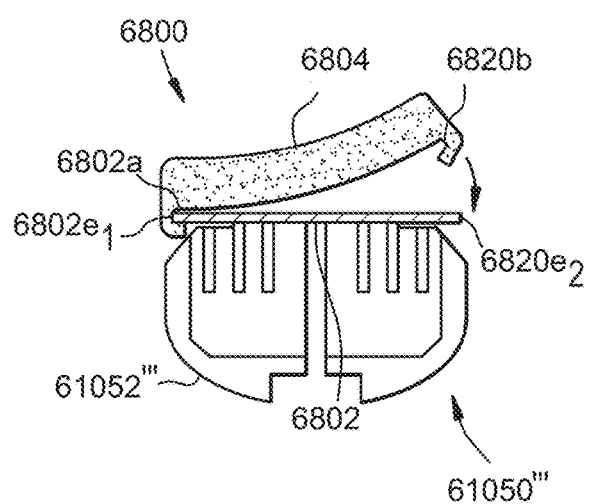
FIG. 40C is a front cross-sectional view illustrating the biologic layer of FIG. 40B partially coupled to the synthetic layer.
Figure 40D:
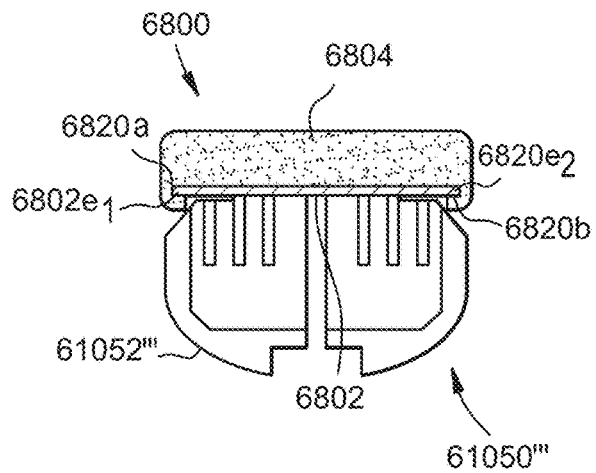
FIG. 40D is a front cross-sectional view illustrating the biologic layer of FIG. 40B fully coupled to the synthetic layer.

As shown in FIG. 40C, a first lengthwise outer edge 6802e1 of the synthetic layer 6802 can be disposed in a first channel 6820a of the biologic layer 6804. The biologic layer 6804, which can be pliable, can be flexed to allow a second lengthwise outer edge 6802e2 of the synthetic layer 6802 to be disposed in a second channel 6820*b* of the biologic layer 6804. The resulting configuration is illustrated in FIGS. 40D and 40E. The fit between the biologic layer 6804 and the synthetic layer 6802 can generally be of the nature that, once coupled along both lengthwise edges, leaves the biologic layer 6804 generally free of stress and tension. Further, the synthetic layer 6802 can provide support for the biologic layer 6804 to prevent it from easily falling apart. As discussed in greater detail below, as staples are ejected by a knife passing through the end effector 61050''', the hybrid adjunct material 6800 is maintained at the surgical site by the staple, and becomes disassociated with the end effector 61050''' when the knife cuts the retention members 61202'''. Even though a matrix or other openings are not overtly formed in the illustrated synthetic layer 6802, the synthetic layer 6802 can be permeable, thereby allowing materials from the biologic layer 6804 to pass therethrough before, during, and after staple delivery. In other embodiments the synthetic layer 6802 can include a matrix, lattice, or other structure containing one or more openings as described above to permit passage of biologic materials from the biologic layer to tissue being stapled.

As illustrated in FIGS. 35B and 36, a hybrid adjunct material 3400', 3500' can be associated with an anvil or upper jaw 31054 in addition to or in lieu of associating the hybrid adjunct material 3400, 3500 with the cartridge assembly or lower jaw 31052 of the end effector 1050. In those earlier described embodiments, brackets 3406, 3506 and 3406', 3506' are used to maintain a location of the hybrid adjunct materials 3400, 3500 and 3400', 3500' with respect to the lower and upper jaws 31052 and 31054. FIGS. 41A and 41B illustrate another embodiment in which a hybrid adjunct material 900 is associated with an anvil or upper jaw 1054'''' of an end effector 1050'''' of an attachment portion 1016''''. As shown, a synthetic material, layer, or matrix 902 is coupled to the anvil 1054'''' using retention members 1202'''' on proximal and distal ends 1054*p*'''', 1054*d*'''' of the anvil 1054''''. A biologic material, layer, or matrix 904 is coupled to the anvil 1054'''' in a manner similar to the manner described above with respect to the lower jaw 1052' of FIG. 37. Accordingly, one or more protrusions (not shown) can extend from the synthetic layer 902 and into the biologic layer 904 such that the two layers 902, 904 are coupled together.

Figure 42A:
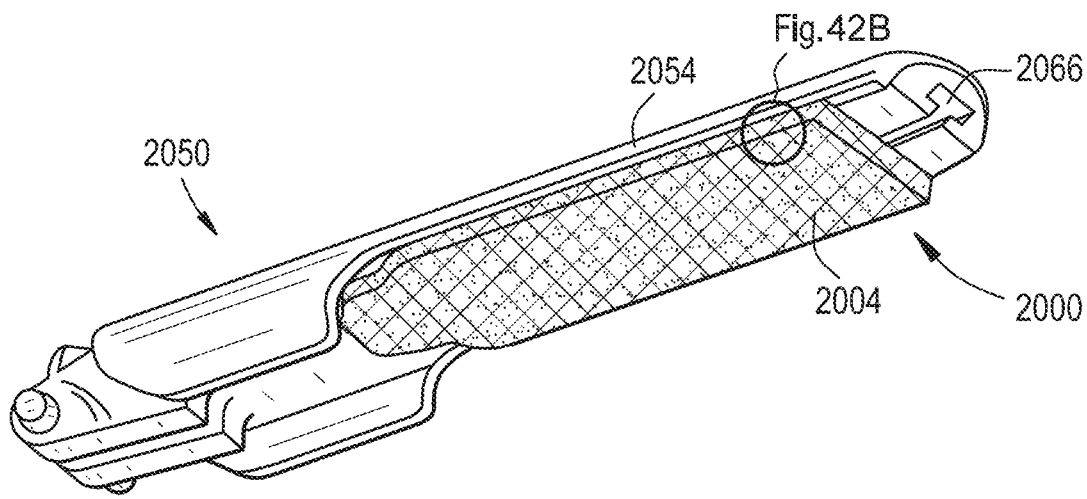
FIG. 42A is a perspective view of one exemplary embodiment of an upper jaw of an end effector having a biologic material coupled thereto.
Figure 42B:
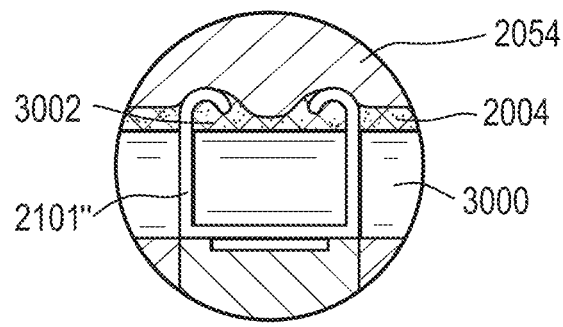
FIG. 42B is a detailed schematic view of a surgical site illustrating a staple disposed both in tissue and in the biologic material of FIG. 42A.
Figure 42C:
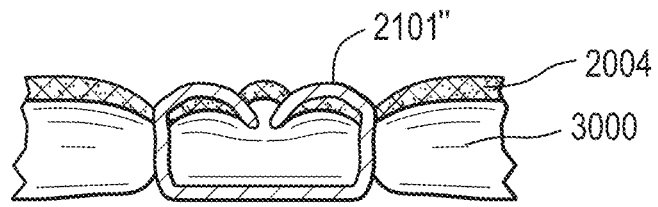
FIG. 42C is a detailed schematic view of the surgical site of FIG. 42B illustrating the staple after it is fully formed.

FIGS. 42A-42C provide for an embodiment of an adjunct material 2000 associated with an anvil or upper jaw 2054 that is completely biologic. Such a configuration can still be considered a hybrid adjunct material to the extent it incorporates multiple biologic materials. As shown, the biologic layer 2004 includes a collagen matrix configured to couple to the anvil 2054 of an end effector 2050. The formation of the biologic layer 2004 can be achieved by purifying and refining collagen. The collagen purification and refinement process can suspend the collagen in an aqueous state. While in this state, fats and other impurities of the collagen can be skimmed off. The aqueous collagen can then be formed into a desired biologic layer shape. For example, the aqueous collagen can be poured into a mold having inverse pockets formed therein that are complementary to the shape of an interior surface of the anvil 2054. Temperature and surface conditions of the mold can be controlled or otherwise tuned by the user to control parameters of the resulting layer, such as the density. In some embodiments an approximately uniform density can be achieved across the layer, while in other embodiments the temperature and surface conditions can be tuned such that the density of the biologic layer 2004 is not uniform across its body. For example, density variants can be formed around inverse pocket shapes formed in the biologic layer 2004. As a result, once the collagen solidifies, the biologic layer 2004 can be keyed into the anvil 2054 of the end effector 2050. In some embodiments, a protrusion (not shown) can be formed that is complementary to a longitudinal slot 2066 formed in the anvil 2054 such that protrusion on the biologic layer 2004 can help to maintain the location of the biologic layer 2044 with respect to the anvil 2054 before and during staple ejection.

In the illustrated embodiment, the biologic layer 2004 is made from biologic material that has adhesive or semi-adhesive properties. By way of non-limiting example, the biologic layer 2004 can be formed by using a thin film of polyglycolic acid (PGA)/poly (ε-caprolactone (PCL), which in a thin film acts as a semi-adhesive. In one exemplary embodiment the PGA/PCL balance is approximately 65/35, although other combinations can be used. A film having approximately this configuration can be such that after the staples are ejected, the remaining collagen would be minimal. More particularly, when compressed against tissue 3000 during clamping the main collagen body of the biologic layer 2004 and the pockets can be crushed, thus, as shown in FIG. 42B, creating a layer that would easily be penetrated by a staple 2101" but would prevent tissue from entering the staple forming area or staple pocket 3002. Still further, after the staple 2101" is fully formed, the collagen matrix of the biologic layer 2004 can be configured to swell and fill gaps, as shown in FIG. 42C. For example, liquids such as hydrogel, oxidized regenerated cellulose (ORC), or alginate can be included as part of the collagen matrix, which help to seal around the legs of the staple 2101" and minimize damage during stapling. As a result, both during and after staple firing, the potential for damage to the vessel, and the potential for bleeding at the surgical site, are reduced.

FIGS. 43A-D illustrate another embodiment of an adjunct material 2200' configured to couple to an anvil or upper jaw 2054' of an end effector 2050'. As shown the adjunct material 2200' includes two biologic layers—a first layer 2204' that includes ORC gel and a second layer 2205' that is formed, at least in part, from omentum and serves as a scaffold or support for the first layer 2204'. The first layer 2204' can create a viscous layer capable of damming up bleeding, thereby allowing the body to more readily clot. In alternative embodiments, as described above, a layer of ORC gel can be used in conjunction with a thin film like PGA/PCL. The film of PGA/PCL can help prevent the ORC gel from activating too quickly when in contact with body fluids, and can help provide shear, tear, and/or axial strength.

The second layer 2205' can also provide shear, tear, and axial strength for the adjunct material 2200'. Omentum is a biologically derived adjunct, and as shown can be formed into a scaffold to help support the ORC gel of the first layer 2204'. Further, omentum is generally compatible with tissue, is capable of mitigating bleeding, and can generally assist in the tissue healing process. The first layer 2204' can be coupled to the second layer 2205' using any techniques known to those skilled in the art and/or described herein. For example, they can be mechanically attached similar to the embodiment of FIG. 37. Alternatively, an adhesive or semi-adhesive collagen layer can be disposed therebetween to serve as a coupling agent. Likewise, the second layer 2205' can be coupled to the anvil 2054' using any techniques known to those skilled in the art and/or described herein. In the illustrated embodiment, an adhesive material such as collagen (not shown) can be applied to either or both of the second layer 2205' and the anvil 2054' to maintain the location of the second layer 2205', and thus the first layer 2204' coupled thereto, with respect to the anvil 2054'. In some embodiments, a third layer (not shown), which like the second layer 2205' can include omentum, can be provided and the first layer 2204' can be sandwiched between the two layers that include omentum. For example, the third layer can be is disposed more proximate to a staple cartridge disposed in a cartridge assembly or lower jaw than the second layer 2205', and thus can help shield the ORC gel of the first layer 2204' from premature activation by tissue disposed between the jaws of the end effector 2050'.

Figure 43A:
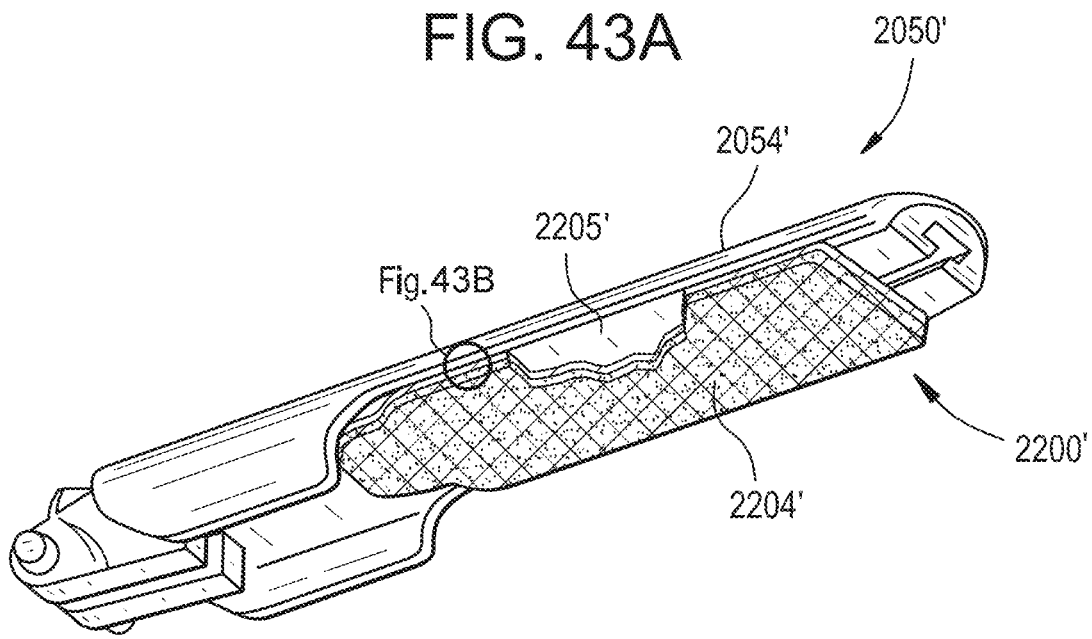
FIG. 43A is a perspective view of another exemplary embodiment of an upper jaw of an end effector having two biologic layers coupled thereto, with a portion of a first biologic layer removed for illustrative purposes.
Figure 43B:
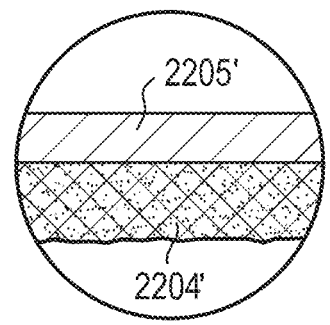
FIG. 43B is a detailed view of the two biologic layers of FIG. 43A.
Figure 43C:
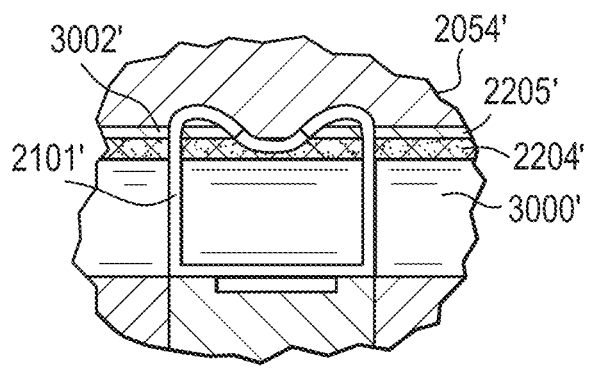
FIG. 43C is a detailed schematic view of a surgical site illustrating a staple disposed both in tissue and through the two biologic layers of FIG. 43B.
Figure 43D:
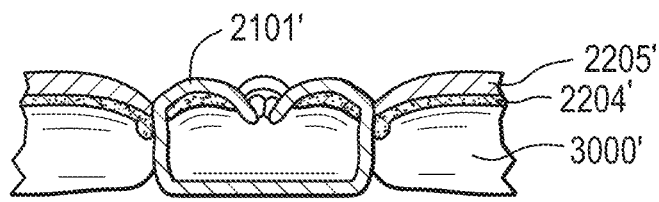
FIG. 43D is a detailed schematic view of the surgical site of FIG. 43C illustrating the staple after it is fully formed.

As a staple 2101' is ejected from the cartridge 2100' and into tissue 3000', the first layer 2204' helps prevent tissue from entering the staple forming area or staple pocket 3002', as shown in FIG. 43C. The tissue 3000' at the surgical site can activate the ORC gel of the first layer 2204'. Accordingly, the ORC gel of the first layer 2204' can begin to melt as it becomes wet. As the ORC melts, it can form a seal around the legs of the staple 2101'. As shown in FIG. 43D, a thickness of the first layer 2204' can be significantly reduced due to the melting, while the second layer 2205' can work in conjunction with the melting ORC to seal holes and gaps around the staple 2101'.

FIGS. 44A-44C provide additional, non-limiting techniques by which a hybrid adjunct material can be formed using both biologic material(s) and synthetic material(s). For example, as shown in FIG. 44A, a hybrid adjunct material 2300''' having a snap-fit configuration can be formed in which the synthetic material, layer, or matrix 2302''' is configured to have features for receiving the biologic material, layer, or matrix 2304'''. As shown, the synthetic layer 2302''' includes opposed channels 2324' formed in outer edges 2302e''' of the layer 2302''', and the biologic layer 2304''' can be pliable such that it can be snap-fit into the synthetic layer 2302'''. In an alternative embodiment of a hybrid adjunct material 2300', which is illustrated in FIG. 44B, a synthetic material, layer, or matrix 2302' can be configured to have a biologic layer 2304' placed on top of it and then the two layers 2302', 2304' can be laminated together. A person skilled in the art will understand various techniques that can be performed to laminate the two layers 2302', 2304' together. In a further alternative embodiment of a hybrid adjunct material 2300'', a synthetic material, layer, or matrix 2302'' can have biologic material 2304'' imbibed into the layer 2302'', as shown in FIG. 44C. Other techniques capable of being used to combine synthetic material(s) and biologic material(s) to form a hybrid adjunct material can also be used without departing from the spirit of the present disclosure.

A hybrid adjunct material that results from combining synthetic material(s) with biologic materials(s) as provided for herein can be associated with any and all of a cartridge assembly or lower jaw, a staple cartridge, and an anvil or upper jaw of an end effector using techniques known to those skilled in the art or otherwise provided for herein. For example, with respect to the hybrid adjunct materials 2300, 2300' of FIGS. 44A and 44B, the synthetic matrices 2302, 2302' can be pre-attached to any of a lower jaw, a staple cartridge, and an upper jaw and then the biologic layer 2304, 2304' can be attached thereto immediately prior to delivery. By way of further non-limiting example, such as for the embodiment of FIG. 44C, the hybrid adjunct material 2300'', which includes both synthetic and biologic materials in the same layer, can be attached to the any of a lower jaw, a staple cartridge, and an upper jaw just prior to delivery of staples to a surgical site.

The components of hybrid adjunct materials can be associated with each other at any desired time, however, it can be preferable to add the biologic material(s) on site if the materials has a limited shelf-life, which many biologic materials do, particularly if they are not dry. Accordingly, as shown in FIGS. 45A and 45B, an attachment portion 2016'' having an end effector 2050'' with a synthetic material, layer, or matrix 2402'' associated therewith can be packaged in a first container 4000, while a biologic material, layer, or matrix 2404'' can be packaged in a second container 4002, separate from a first container 4000. As shown, the synthetic layer 2402'' is pre-attached to the end effector 2050'' by retention members 2202''. Storing the biologic material 2404'' in a separate, closed environment can be conducive to preserving its shelf-life. For example, the biologic material 2404'' can be refrigerated prior to associating it with the synthetic material 2402'' for subsequent deployment. Alternatively, the biologic material can be completely dried, which can also improve its shelf-life. In other embodiments, the synthetic material, layer, or matrix can be initially detached from an end effector, and can be packaged with or separate from either of the end effector or the biologic material. Prior to delivery of the synthetic and biologic materials to the surgical site, the two materials can be combined to form a hybrid adjunct material and can then be attached to the end effector for subsequent use at the surgical site. A person skilled in the art will understand other techniques that can be used to package the tool and the components of the hybrid adjunct material to preserve the shelf-life of any biologic materials without departing from the spirit of the present disclosure.

Hybrid Adjunct Materials with Compressible Elastic Members

The compressible elastic members described herein, or otherwise known to those skilled in the art, can be used in conjunction with a variety of adjunct materials. While in some instances adjunct materials can be either a synthetic material or a biologic material, in various embodiments the adjunct material includes both synthetic material(s) and biologic material(s) (i.e., it is a hybrid adjunct material). The resulting combination can advantageously exhibit beneficial features from both types of materials in a single hybrid material. For example, a hybrid adjunct material can be designed to combine benefits of biologic material (such as improved healing and tissue growth at a surgical site) with desirable mechanical properties of synthetic material (such as springiness or elasticity). In various embodiments, a synthetic material can also provide structure and support for a biologic material (e.g., add strength and/or shear resistance to fibrous biologic material), while still allowing the biologic material to contact a surgical site and support and/or promote healing. Further, hybrid adjunct materials can be configured to help reduce inflammation, promote cell growth, and/or otherwise improve healing. The hybrid adjunct material can be bioimplantable and bioabsorbable.

FIG. 46 is a perspective view of an exemplary staple cartridge assembly that includes a cartridge body and a hybrid adjunct material. Here, the cartridge body and staples (not shown) are encased by lower jaw 71052 of an end effector of a surgical instrument (see, e.g., FIGS. 1 and 10). The cartridge body has a plurality of staple cavities configured to seat staples therein (see, e.g., FIGS. 4 and 10). The hybrid adjunct material 7600 is releasably retained on the cartridge body and the lower jaw 71052 and configured to be delivered to tissue by deployment of the staples from the cartridge body (as will be discussed in connection with the example of FIGS. 51-53 below). The material 7600 includes a biologic tissue membrane or matrix 7604 (shown as being partially cutaway to illustrate the compressible elastic members or spring members 7616), a synthetic substrate layer or matrix 7602, and at least one compressible elastic member or spring member 7616 configured to compress when a compressive force is applied thereto, and to provide a spring back force when the compressive force is removed. Because the compressible elastic member or spring member 7616 (also referred to as a "skeleton") is internal to the biologic tissue membrane or matrix 7604, irritation and inflammation from synthetic material can be minimized while the biologic tissue membrane or matrix 7604 is still provided with a compliant reinforcement.

In the illustrated embodiment of FIG. 46 (and similarly in FIGS. 47-49 and 51-53), the biologic tissue membrane 7604 is on a tissue contacting side of the hybrid adjunct material 7600 while the synthetic substrate layer 7602 is on the side of the material 7600 facing the cartridge body. A person skilled in the art will also appreciate that the relative positions of layers 7602 and 7604 can be reversed. A person skilled in the art will also appreciate that while the cartridge assembly of FIG. 46 includes a hybrid adjunct material, an adjunct material that includes one or more spring members and only one of a biologic layer and a synthetic layer may alternatively be used. In various embodiments, hybrid adjunct materials can include a number (and arrangement) of compressible spring members selected to achieve a desired mechanical property. For example, the number of spring members may be matched to the number (and location) of staples, or the number of spring members may be the number required to cover the biologic tissue membrane or synthetic substrate layer, or a predetermined region thereof (e.g., a function of the size of the spring member and membrane or layer).

Further, in the illustrated embodiment of FIG. 46 (and similarly in FIGS. 47-49 and 51-53), the hybrid adjunct material is assembled to an end effector for context and ease of description. A person skilled in the art will appreciate that that hybrid adjunct materials can be provided in alternatively configured assemblies with an end effector, and can be provided separately from an end effector (or other component of a surgical stapler) and subsequently affixed to a portion of the end effector.

The hybrid adjunct material can be coupled to a jaw of the end effector (in this example through the synthetic substrate layer) and can include one or more mating features for receiving and coupling to a biologic layer. For example, FIG. 46 illustrates a synthetic material, layer, or matrix 7602 of the hybrid adjunct material 7600 coupled to the jaw 71052 using retention members 71202 extending across proximal and distal ends 71052*p*, 71052*d* thereof. Further, the synthetic matrix 7602 can include one or more protrusions, shown here as springs 7616, which are configured to engage a biologic material, layer, or matrix 7604 to assist in mating the biologic matrix 7604 to the synthetic matrix 7602, thereby substantially maintaining a location of the biologic matrix 7604 with respect to the synthetic matrix 7602.

In this embodiment, the compressible elastic members or spring members 7616 form a skeletal structure around which the biologic matrix 7604 is formed. For example, when the biologic matrix 7604 is formed from collagen, which as discussed elsewhere in this disclosure can be melted into a liquid state and then reformed into a hardened state, the synthetic matrix can be dipped in liquid collagen. As the collagen reforms or hardens, it can form around the skeletal structure defined by the configuration of the springs 7616, thereby integrating the biologic matrix with the synthetic matrix. The resulting hybrid adjunct material can be a macro-composite adjunct that benefits from the strength and tear resistance of the internal synthetic frame and the simple parameter attachment features provided by the springs 7616, e.g., the shape and material of the springs, while still providing for the benefits of having biologic material. A person skilled in the art will recognize a variety of other protrusions that can extend from a top surface 7602*a* of the synthetic matrix 7602, to provide an internal skeletal structure for forming a hybrid adjunct material.

A person skilled in the art will appreciate that compressible elastic members having a variety of shapes, sizes, and configurations, and materials, can be used with the adjunct material disclosed herein. In one embodiment, shown in FIG. 46, the adjunct material includes spring members 7616 in the form of elongate members that extend along at least one dimension of the adjunct material. For example, in the illustrated embodiment, spring members 7616 can be elongate members that have raised segments 7618 separated by non-raised segments 7617. In one example, the elongate members 7616 can form a sinusoidal or wave-like pattern. Although FIG. 46 illustrates elongate members 7616 extending across a width (W) dimension, a person skilled in the act will recognize that the elongate members can alternatively, or in addition, extend along a length (L) dimension or another dimension (i.e., in FIG. 46, a dimension that is not parallel or perpendicular to the length dimension or width dimension). A person skilled in the art will also appreciate that spring members can take a variety of alternative forms. Virtually any shape can be utilized as long as it is able to provide a spring back force when a compressive force is removed. Further, the spring member can be disposed in or on either the biologic and/or synthetic layer, or disposed between layers.

FIGS. 47-50C illustrate additional exemplary attachments of biological tissue reinforcement membranes to cartridge bodies, and exemplary compressible elastic members. In FIG. 47, the hybrid adjunct material 82000 includes spherical, or orbit-like, elastic members 82016 disposed between a synthetic layer 82002 and biologic matrix 82004, and embedded within the biologic matrix 82004. In FIG. 48, the hybrid adjunct material 82100 includes radially projecting, atom-like, or jack-like elastic members 82116 embedded within the biologic matrix 82104. In FIG. 49, the hybrid adjunct material 82200 includes hemispherical, or domed, elastic members 82216 embedded within the biologic matrix 82204.

FIG. 50A is an exploded view of a variation of the compressible elastic member illustrated in FIG. 47. The spherical, or orbit-like, elastic member 82320 includes a plurality of circular, or elliptical components 82330 defining a three dimensional spherical, or orbit-like shape. A person skilled in the art will appreciate that such elastic members can include two or more circular or elliptical components, which can be arranged in a regular or irregular pattern. A person skilled in the art will also appreciate that the mechanical properties of such elastic members can be modulated, for example, by appropriate selection of the material, size, shape, position, and/or number of circular or elliptical components. These and other elastic members can include one or more surface features, or features of the three dimensional shape of the elastic member itself, configured to fix the membrane to the elastic member. In the example of FIG. 50A, a membrane or matrix can extend around a spherical, or orbit-like, elastic member 82320 and through the interstices defined by the plurality of circular, or elliptical components 82330, thereby embedding and fixing the elastic member 82320 to and/or within the membrane or matrix.

FIG. 50B is an exploded view of a variation of the compressible elastic member illustrated in FIG. 49. The hemispherical, or domed elastic member 82322 includes a plurality of curvilinear components 82332 affixed to a circular, or elliptical base 82342 and defining a three dimensional hemispherical, or domed shape. A person skilled in the art will appreciate that such elastic members can include two or more curvilinear components, which can be arranged in a regular or irregular pattern, fixed to a circular, elliptical, polygonal, or other two dimensional base. A person skilled in the art will also appreciate that the mechanical properties of such elastic members can be modulated, for example, by appropriate selection of the material, size, shape, position, and/or number of curvilinear components and base. These and other elastic members can include one or more surface features, or features of the three dimensional shape of the elastic member itself, configured to fix the membrane to the elastic member. In the example of FIG. 50A, a membrane or matrix can extend around a curvilinear elastic member 82332 and through the interstices defined by the plurality of curvilinear elastic members 82332 and/or base 82342, thereby embedding and fixing the elastic member 82322 to and/or within the membrane or matrix.

FIG. 50C is an exploded view of a variation of the compressible elastic member illustrated in FIG. 48. The radially projecting, atom-like, or jack-like elastic members 82321 includes a nucleus 82331 from which arms 82341 radiate and terminate in ball shaped end cap 82351. A person skilled in the art will appreciate that similar elastic members can include two or more arms, which are not necessarily straight or equal in length, radiating from a nucleus, which is not necessarily the geometric center of the elastic member. A person skilled in the art will also appreciate that the mechanical properties of such elastic members can be modulated, for example, by appropriate selection of the material, size, shape, position, and/or number of arms, end caps, and other features. These and other elastic members can include one or more surface features configured to fix the membrane to the elastic member (e.g., ball shaped end caps, shelves, barbs, and the like). Features such as ball shaped end caps may have addition advantageous features, such as blunting the tip of arm 82341, thereby preventing the arm from piercing or otherwise disrupting an adjacent region of membrane or matrix. In the non-limiting example of FIG. 50C, the elastic member 82321 has radially projecting arms 82341 and ball shaped end caps 82351 can be embedded in a membrane or matrix, thereby fixing the elastic member within the membrane or matrix and mitigating movement of the elastic member within the membrane or matrix. A person skilled in the art will appreciate that other surface features and configurations can be used in other embodiments.

A person skilled in the art will appreciate that shapes other than those illustrated in the examples of FIGS. 47-50C, e.g., spheroid, ovoid, three-dimensional radial, non-symmetrical form, and functionally similar two or three-dimensional elastic member shapes, can be used in alternative embodiments. Likewise, the elastic member need not necessarily assume a configuration of the illustrated embodiments (e.g., disposed between a synthetic layer and a biologic layer and/or embedded within a biologic layer—the spring member can be disposed in or on either the biologic and/or synthetic layer, or disposed between layers.). A person skilled in the art will also appreciate that the mechanical properties (e.g., compression and spring back behavior) of a hybrid adjunct material can be modulated by appropriate selection of the number, type, and/or arrangement of elastic members. For example, the type and/or arrangement of elastic members can be uniform (e.g., similar to FIG. 47), random (e.g., similar to FIG. 48), or patterned (e.g., similar to FIG. 49, to concentrate compression and spring back around the staples). Furthermore, in various embodiments, a hybrid adjunct material can include two or more different types of elastic members and/or two or more patterns (e.g., regular pattern of a first type of elastic member at staple sites and a random pattern of a second type of elastic member elsewhere).

Elastic members can be made from essentially any synthetic material having the desired mechanical (e.g., springiness, recoverable viscoelasticity, reinforcement and the like) and biologic (e.g., bioimplantable and bioabsorbable) properties. Representative examples are discussed in the IMPLANTABLE MATERIALS section above. Likewise, essentially any shape and configuration having spring-like properties can be used, assuming compatibility (e.g., shape, volume) with the hybrid adjunct material. A person skilled in the art will appreciate that the shape of hybrid adjunct materials (and layers thereof) are not limited to the parallelepiped/rhombohedron like forms shown in the illustrated examples. In various embodiments, hybrid adjunct materials (and layers thereof) are not necessarily symmetrical as shown in FIGS. 46-49 and can, for example, vary in thickness or have irregularly shaped portions.

In another aspect, the invention provides a method for stapling biological tissue. FIGS. 51-53 illustrate an example of one such method, through operation of the exemplary staple cartridge encased by lower jaw 91052 of an end effector shown in FIG. 46. While the example method is discussed with reference to FIG. 46, it is understood that this and other methods provided by the present invention are applicable to the use of adjunct materials with different types of spring members discussed herein.

FIG. 51 illustrates the engagement of tissue 93000 with a surgical stapler cartridge body 91100 at a surgical site. The cartridge body 91100 has a hybrid adjunct material 9600 releasably attached thereto. The material 9600 comprises a biologic tissue membrane 9604, a synthetic substrate layer 9602, and at least one compressible elastic member 9616 configured to compress when a compressive force is applied thereto, and to provide a spring back force when the compressive force is removed. Here, the tissue 93000 is engaged between an anvil or upper jaw 91054 and the lower jaw 91052, which encases the cartridge body 91100 having staples 91101 disposed therein, and which supports the hybrid adjunct material 9600.

FIG. 52 illustrates an actuated surgical stapler that has ejected staples 91101 from the cartridge body 91100, and into the biological tissue 93000. The staples 91101 extend through the hybrid adjunct material 9600 to maintain the material 9600 at the surgical site. In this example, actuation of the surgical stapler also cuts the tissue 93000 at a surgical site between the staples 91101, as shown in FIG. 52. Further embodiments and examples of such cutting embodiments are described above. However, the present invention also contemplates embodiments where tissue is not necessarily cut, or where tissue is not necessarily cut concurrently with actuation of the surgical stapler.

FIG. 53 illustrates the tissue 93000 following deployment of staples 91101 and adjunct material 9600. As shown, the staples 91101 extend through the hybrid adjunct material 9600 and the tissue 93000 to maintain the material 9600 at the surgical site. In this illustration, the tissue 93000 comprising the staples 91101 is reinforced by the hybrid adjunct material 9600, thereby preventing or mitigating tearing, fluid (e.g., blood), or other undesired damage to the surgical site. Avoiding undesired damage can decease surgical recovery time and mitigate surgical complications. Furthermore, the reinforcement can promote healing through the action of the biologic matrix 9604 and/or biologically active compounds therein. Similarly, the reinforcement can prevent or mitigate irritation and inflammation from synthetic material because the elastic member or spring 9616 is internal to the biologic tissue membrane or matrix 9604 and/or because the synthetic substrate layer 9602 essentially does not contact the tissue 93000. In alternative embodiments, essentially all synthetic material can be encapsulated by biologic material, to prevent or mitigate irritation and inflammation from synthetic materials.

Reuse

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., electrodes, a battery or other power source, an externally wearable sensor and/or housing therefor, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

In some embodiments, devices described herein can be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Additional exemplary structures and components are described in U.S. application Ser. No. 14/074,884 entitled "Sealing Materials For Use In Surgical Stapling," Ser. No. 14/074,810 entitled "Hybrid Adjunct Materials For Use In Surgical Stapling," Ser. No. 14/075,438 entitled "Positively Charged Implantable Materials And Method Of Forming The Same," and Ser. No. 14/074,902 entitled "Hybrid Adjunct Materials For Use In Surgical Stapling," which are filed on even date herewith and herein incorporated by reference in their entireties.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A surgical system comprising:
    an adjunct including a biologic material and a synthetic material; and
    a surgical staple cartridge;
    wherein the synthetic material has a plurality of openings therein configured to allow components of the biologic material to pass therethrough;
    the adjunct is configured to be mated to the surgical staple cartridge with the synthetic material directly contacting the surgical staple cartridge and with the biologic material facing away from the surgical staple cartridge; and
    the adjunct is configured to be implanted in a body of a patient with the biologic material in contact with a tissue of the patient and with the synthetic material facing away from and not in contact with the tissue of the patient.

2. The surgical system of claim 1, wherein the biologic material comprises a bioabsorbable membrane.

3. The surgical system of claim 1, wherein the biologic material comprises an extracellular matrix.

4. The surgical system of claim 1, wherein the biologic material comprises a patient-derived material including at least one of platelet enriched plasma, diced tissue fragments, fibrin, and stem cells.

5. The surgical system of claim 1, wherein the biologic layer comprises at least one of platelet poor plasma (PPP), platelet rich plasma (PRP), starch, chitosan, alginate, fibrin, thrombin, polysaccharide, cellulose, collagen, bovine collagen, bovine pericardium, gelatin-resorcin-formalin adhesive, oxidized cellulose, mussel-based adhesive, poly (amino acid), agarose, polyetheretherketones, amylose, hyaluronan, hyaluronic acid, whey protein, cellulose gum, starch, gelatin, and silk.

6. The surgical system of claim 1, wherein the synthetic layer comprises a polymer mesh.

7. The surgical system of claim 1, wherein the synthetic layer comprises at least one of polydioxanone, Polyglycerol sebacate (PGS), PGA (Polyglycolic acid), PCL (Polycaprolactone), PLA or PLLA (Polylactic acid), PHA (polyhydroxyalkanoate), PGCL (poliglecaprone 25), PANACRYL, Polyglactin910, Poly glyconate, PGA/TMC (polyglycolide-trimethylene carbonate), polyhydroxybutyrate (PHB), poly (vinylpyrrolidone) (PVP), poly(vinyl alcohol) (PVA), and a blend of copolymerization of the PGA, PCL, PLA, PDS monomers.

8. The surgical system of claim 1, wherein the surgical staple cartridge is configured to be coupled to a jaw of a surgical stapler.

9. The surgical system of claim 1, further comprising a surgical end effector;
    wherein the surgical staple cartridge is configured to be seated in the surgical end effector.

10. A surgical method comprising:
    implanting an adjunct in a body of the patient with a biologic material of the adjunct in contact with a tissue of the patient and with a synthetic material of the adjunct facing away from and not in contact with the tissue of the patient;
    wherein the synthetic material has a plurality of openings therein configured to allow components of the biologic material to pass therethrough;
    the adjunct is implanted using a surgical stapler with the adjunct mated to a surgical staple cartridge with the synthetic material directly contacting the surgical staple cartridge and with the biologic material facing away from the surgical staple cartridge.

11. The method of claim 10, wherein the synthetic material comprises at least one of polydioxanone, Polyglycerol sebacate (PGS), PGA (Polyglycolic acid), PCL (Polycaprolactone), PLA or PLLA (Polylactic acid), PHA (polyhydroxyalkanoate), PGCL (poliglecaprone 25), PANACRYL, Polyglactin910, Poly glyconate, PGA/TMC (polyglycolide-trimethylene carbonate), polyhydroxybutyrate (PHB), poly (vinylpyrrolidone) (PVP), poly(vinyl alcohol) (PVA), and a blend of copolymerization of the PGA, PCL, PLA, PDS monomers.

12. The method of claim 10, wherein the biologic material comprises a patient-derived material including at least one of platelet enriched plasma, diced tissue fragments, fibrin, and stem cells.

13. A method of manufacturing comprising:
    treating a surface of a hydrophobic synthetic material to form a hydrophilic portion including pockets formed in the surface;
    wherein the hydrophilic portion is configured to encourage cellular ingrowth; and
    the treated synthetic material is configured to be implanted in a body of a patient with a surface of the hydrophilic portion including the pockets formed therein in contact with a tissue of the patient and with an opposite, hydrophobic surface of the treated synthetic material facing away from and not in contact with the tissue of the patient.

14. The method of claim 13, wherein the surface of the hydrophobic synthetic material is treated with an acid or base.

15. The method of claim 14, further comprising removing the acid or base from the synthetic material after the pockets have been formed and before the treated synthetic material is implanted in the body of the patient.

16. The method of claim 13, further comprising mating the treated synthetic material to a surgical staple cartridge;
    wherein the treated synthetic material directly contacts the surgical staple cartridge with the hydrophilic portion facing away from the surgical staple cartridge.

17. The method of claim 13, further comprising mating the treated synthetic material to a jaw of an end effector of a surgical stapler;
    wherein the treated synthetic material directly contacts the jaw with the hydrophilic portion facing away from the jaw.

18. The method of claim 13, wherein the synthetic material includes an absorbable polymer.

19. The method of claim 13, wherein the synthetic material is a polylactic acid (PLA)/polycaprolactone (PCL) copolymer.

20. The method of claim 13, wherein the hydrophobic polymer is a polyglycolic acid (PGA)/polycaprolactone (PCL) copolymer having polyethylene glycol and/or poloxamer repeat units.

* * * * *